Figure 7A:
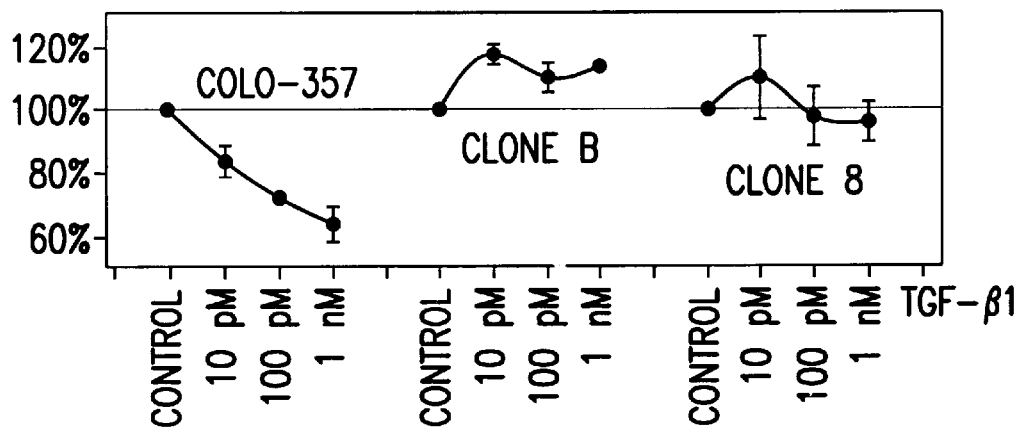

United States Patent [19]
Falb

[11] Patent Number: 6,099,823
[45] Date of Patent: Aug. 8, 2000

[54] COMPOSITIONS AND METHODS FOR THE TREATMENT AND DIAGNOSIS OF CARDIOVASCULAR DISEASE

[75] Inventor: Dean A. Falb, Wellesley, Mass.

[73] Assignee: Millennium Pharmaceuticals, Inc., Cambridge, Mass.

[21] Appl. No.: 09/126,640

[22] Filed: Jul. 30, 1998

Related U.S. Application Data

[63] Continuation-in-part of application No. 08/870,434, Jun. 6, 1997, which is a continuation-in-part of application No. 08/799,910, Feb. 13, 1997
[60] Provisional application No. 60/011,787, Feb. 16, 1996.
[51] Int. Cl.$^7$ .............................. C12Q 1/68; C12N 15/85; C12N 15/86; C07H 21/02; C07H 21/04; A61K 49/00
[52] U.S. Cl. ........................... 424/9.1; 536/23.1; 424/9.2; 435/6; 435/325
[58] Field of Search .................................. 435/70.1, 325, 435/69.1, 6, 91.1, 91.3, 320.1, 4; 536/23.1, 24.5; 424/9.1

[56] References Cited

U.S. PATENT DOCUMENTS

| | | | |
|---|---|---|---|
| 5,262,311 | 11/1993 | Liang et al. | 435/91.2 |
| 5,418,162 | 5/1995 | Blakely et al. | 435/348 |
| 5,424,187 | 6/1995 | Shor et al. | 435/6 |
| 5,545,569 | 8/1996 | Grainger et al. | 436/518 |

FOREIGN PATENT DOCUMENTS

| | | |
|---|---|---|
| 0 282 899 A2 | 9/1988 | European Pat. Off. . |
| 0 670 369 A2 | 9/1995 | European Pat. Off. . |
| WO 95/23858 | 9/1995 | WIPO . |
| PCT/US97/ 02291 | 7/1997 | WIPO . |

OTHER PUBLICATIONS

Barnes et al., 1994, "PCR amplification of up to 35–kb DNA with high fidelity and high yield from λ bacteriophage templates", *PNAS USA* 91:2216–2220.
Bartel et al., 1993, "Using the two–hybrid system to detect protein—protein interactions", *Cellular Interactions in Dev.* Chap. 7, pp. 153–159.
Bevilacqua et al., 1989, "Endothelial leukocyte adhesion molecule 1: an inducible receptor for neutrophils related to complement regulatory proteins and lectins", *Science* 243:1160–1165.
Bevilacqua et al., 1991, "Selectins: A family of adhesion receptors", *Cell* 67:233.
Bird et al., 1988, "Single–chain antigen–binding proteins", *Science* 242:423–426.
Blachly–Dyson et al., 1993, "Cloning and functional expression in ueast of two human isoforms of the outer mitochondrial membrane channel, the voltage–dependent anion channel", *J. Biol. Chem.* 268:1835–1841.
Black et al., 1994, "Raloxifene (LY139481 HCI) prevents bone loss and reduces serum cholesterol without causing uterine hypertrophy in ovariectomized rats", *J. Clin. Invest.* 93:63–69.
Boise et al., 1993, "bcl–x, a bcl–2 related gene that functions as a dominant regulator of apoptotic cell death", *Cell* 74:597–608.
Border & Noble, 1995, "Targeting TGF–β for treatment of disease", *Nature Med.* 1:1000–1001.
Cercek et al., 1990, "Induction of insulin–like growth factor I messenger RNA in rat aorta after balloon denudation", *Cir. Res.* 66:1755–1760.
Charles et al., 1993, "Genomic structure, cDNA sequence, and expression of gly96, a growth factor–inducible immediate–early genes encoding a short–lived glycosylated protein", *Oncogene* 8:797–801.
Chen et al., 1996, "A transcriptional partner for MAD proteins in TGF–β signaling", *Nature* 383:691–696.
Cheng et al., 1994, "Effective ampliciation of long targets from cloned inserts and human genomic DNA", *PNAS USA* 91:5695–5699.
Cleary et al., 1986, "Cloning and structural analysis of cDNAs for bcl–2 and a hybrid bcl–2/Immunoglobulin transcript resulting from the t(14;18) translocation", *Cell* 47:19–28.
A. Coghlan, 1995, "Gene dream fades away", *New Scientist* :14–15.
Coffman et al., 1990, "Xotch, the Xenopus homolog of Drosophila Notch", *Science* 249:1438–1441.
Cybulsky & Gimbrone, 1991, "Endothelial expression of a mononuclear leukocyte adhesion molecule during atherogenesis", *Science* 251:788–791.
Davies et al., 1986, "Turbulent fluid shear stress induces vascular endothelial cell turnover in vitro", *PNAS USA* 83:2114–2117.
Diamond et al., 1993, "Novel delayed–early and highly insulin–induced growth response genes", *J. Biol. Chem.* 268:15185–15192.

(List continued on next page.)

Primary Examiner—George C. Elliott
Assistant Examiner—Janet Epps
Attorney, Agent, or Firm—Pennie & Edmonds LLP

[57] ABSTRACT

The present invention relates to methods and compositions for the treatment and diagnosis of cardiovascular disease, including, but not limited to, atherosclerosis, ischemia/reperfusion, hypertension, restenosis, and arterial inflammation. Specifically, the present invention identifies and describes genes which are differentially expressed in cardiovascular disease states, relative to their expression in normal, or non-cardiovascular disease states, and/or in response to manipulations relevant to cardiovascular disease. Further, the present invention identifies and describes genes via the ability of their gene products to interact with gene products involved in cardiovascular disease. Still further, the present invention provides methods for the identification and therapeutic use of compounds as treatments of cardiovascular disease. Moreover, the present invention provides methods for the diagnostic monitoring of patients undergoing clinical evaluation for the treatment of cardiovascular disease, and for monitoring the efficacy of compounds in clinical trials. Additionally, the present invention describes methods for the diagnostic evaluation and prognosis of various cardiovascular diseases, and for the identification of subjects exhibiting a predisposition to such conditions.

22 Claims, 22 Drawing Sheets

OTHER PUBLICATIONS

Eppert et al., 1996, "MADR2 maps to 18q21 and encodes a TGFβ–regulated MAD–related protein that is functionally mutated in colorectal carcinoma", *Cell* 86:543–552.

Farrow et al., 1995, "Cloning of a bcl–2 homologue by interaction with adenovirus E1B 19K", *Nature* 374:731–733.

M.A. Gimbrone, 1976, "Culture of vascular endothelium", *Progress in Hemostasis and Thrombosis* Spaet (ed.), Grune & Stratton Inc., NY, 3:1–28.

Grainger et al., 1993, "Proliferation of human smooth muscle cells promoted by lipoprotein(a)", *Science* 260:1655–1658.

Grainger et al., 1995, "Tamoxifen elevates transforming growth factor–β and suppresses diet–induced formation of lipid lesions in mouse aorta", *Nature Med.* 1:1067–1073.

Gromadzinska & Sklodowska, 1990, "Erythrocyte glutathione peroxidase and myocardial infarction", *JAMA* 263:949–950.

Guidi et al., 1986, "Platelet glutathione peroxidase activity is impaired in patients with coronary heart disease", *Scand. J. Clin. Lab Invest.* 46:549–551.

T. Gura et al., 1995, "Estrogen: Key player in heart disease among women", *Science* 269:771–773.

Hakes & Berezney, 1991, "Molecular cloning of matrin F/G: A DNA binding protein of the nuclear matrix that contains putative zinc finger motifs", *PNAS USA* 88:6186–6190.

K. Heckl, 1988, "Isolation of cDNAs encoding human manganese superoxide dismutase", *Nuc. Acids Res.* 16:6224.

Hockenbery et al., 1993, "Bcl–2 functions in an antioxidant pathway to prevent apoptosis", *Cell* 75:241–251.

Hochman et al., 1995, "Dissociation of synchronization and excitability in furosemide blockage of epileptiform activity", *Science* 270:99–102.

Hoodless et al., 1996, "MADR1, a MAD–related protein that functions in BMP2 signaling pathways", *Cell* 85:489–500.

Jones et al., 1993, "Molecular cloning of human prostaglandin endoperoxide syntase type II and demonstration of expression in response to cytokines", *J. Biol. Chem.* 268:9049–9054.

Kanai et al., 1995, "Identification and characterization of a prostaglandin transporter", *Science* 268:866–869.

Kita et al., 1987, "Probucol prevents the progression of atherosclerosis in Watanabe heritable hyperlipidemic rabbit, and animal model for familial hypercholesterolemia", *PNAS USA* 84:5928–5931.

Kojima et al., 1991, "Lipoprotein (a) inhibits the generation of transforming growth factor β: An endogenous inhibitor of smooth muscle cell migration",*J. Cell Biol.* 113:1439–1445.

Kok et al., 1989, "Decreased selenium levels in acute myocardial infarction", *JAMA* 261:1161–1164.

Kumar & Chambon, 1988, "The estrogen receptor binds tightly to its responsive element as a ligand–induced homodimer", *Cell* 55:145–156.

Kume et al., 1992, "Lysophosphatidylcholine, a component of atherogenic lipoproteins, induces mononuclear leukocyte adhesion molecules in cultured human and rabbit arterial endothelial cells", *J. Clin. Invest.* 90:1138–1144.

F. Ledley, 1995, "Nonviral gene therapy: The promise of genes as pharmaceutical products", *Human Gene Therapy* 6:1129–1144.

Li et al., 1991, "Early induction of an atherosclerosis–associated endothelial–leukocyte adhesion molecule (athero–ELAM) by an atherogenic diet in rabbits", *Arterioscler. Thromb.* 11:1397a.

Luscinskas et al., 1989, "Endothelial–leukocyte adhesion molecule–1–dependent and leukocyte (CD11/CD18)–dependent mechanisms contribute to polymorphonuclear leukocyte adhesion to cytokine–activated human vascular endothelium", *J. Immunol.* 142:2257–2263.

Majesky et al., 1990, "PDGF ligand and receptor gene expression during repair of arterial injury", *J. Cell Biol.* 111:2149–2158.

Malden et al., 1991, "The influence of oxidatively modified low density lipoproteins on expression of platelet–derived growth factor by human monocyte–derived macrophages", *J. Biol. Chem.* 266:13901–13907.

E. Marshall, 1995, "Less hype, more biology needed for gene therapy", Science 270(5243), p. 1751.

E. Marshall, 1995, "Gene therapy's growing pains", *Science* 269:1050–1055.

Nagel et al., 1994, "Shear stress selectively upregulates intercellular adhesion molecule–1 expression in cultured human vascular endothelial cells", *J. Clin. Invest.* 94:885–891.

Navab et al., 1988, "Monocyte migration into the subendothelial space of a coculture of adult human aortic endothelial and smooth muscle cells", *J. Clin. Invest.* 82:1853–1863.

Nikol et al., 1992, "Expression of transforming growth factor–β1 is increased in human vascular restenosis lesions", *J. Clin. Invest.* 90:1582–1592.

Ohno et al., 1994, "Gene therapy for vascular smooth muscle cell proliferation after arterial injury", *Science* 265:781–784.

Oltvai et al., 1993, "Bcl–2 heterodimerizes in vivo with a conserved homology, Bax, that accelerates programmed cell death", *Cell* 74:609–619.

Orkin & Motulsky, 1995, "Report and recommendations of the panel to assess the NIH investment in research on gene therapy", *NIH Report*.

Osborn et al., 1989, "Direct expression cloning of vascular cell adhesion molecule 1, a cytokine–induced endothelial protein that binds to lymphocytes", *Cell* 59:1203–1211.

Plump et al., 1992, "Severe hypercholesterolemia and atherosclerosis in apolipoprotein e–deficient mice created by homologous recombination in ES cells", *Cell* 71:343–353.

Porter et al., 1992, "Plasma, platelet and erythrocyte glutathione peroxidases as risk factors in ischaemic heart disease in man", *Clinical Science* 83:343–345.

Poston et al., 1992, "Expression in intercellular adhesion molecule–1 in atherosclerotic plaques", *Am. J. Pathol.* 140:665–673.

Puolakkainen et al., 1993, "Serological response to *Chlamydia pneumoniae* in adults with coronary arterial fatty streaks and fibrolipid plaques", *J. of Clinical Microbiol.* 31:2212–2214.

Raftery et al., 1988, "Genetic screens to identify elements of the decapentaplegic signaling pathway in Drosophila", *Genetics* 139:241–254.

Rapacz et al., 1986, "Lipoprotein mutations in pigs are associated with elevated plasma cholesterol and atherosclerosis", *Science* 234:1573–1577.

Resnick et al., 1993, "Platelet–derived growth factor B chain promoter contains a cis–acting fluid shear–stress–responsive element", *PNAS USA* 90:4591–4595.

R. Ross, 1993, "The pathogenesis of atherosclerosis: A perspective for the 1990s" *Nature* 362:801–809.

Sambrook et al.(eds), 1989, "Estimating the Effects of Mismatches", *Molecular Cloning—A Laboratory Manual 2nd Edition*, pp. 11–47.

Sekelsky et al., 1995, "Genetic characterization and cloning of Mothers against dpp, a gene required for decapentaplegic function in *Drosophila melanogaster*", *Genetics* 139:1347–1358.

Serra & Moses, 1996, "Tumor suppressor genes in the TGF–β signaling pathway?", *Nature Med.* 2:390–391.

Shreeniwas et al., 1991, "Reoxygenation stimulates IL–1α production, increasing leukocyte adherence to endothelium via expression of ICAM–1 and ELAM–1", *Arterioscler. Council Abstracts* 11:1397a.

Simmons et al., 1988, "ICAM, an adhesion ligand of LFA–1, is homologous to the neural cell adhesion molecule NCAM", *Nature* 331:624–627.

Speir et al., 1994, "Potential role of human cytomegalovirus and p53 interaction in coronary restenosis", *Science* 265:391–394.

Takahashi et al., 1990, "Primary structure of human plasma glutathione peroxidase deduced from cDNA sequences", *J. Biochem.* 108:145–148.

Takayama et al., 1995, "Cloning and functional analysis of BAG–1: A novel bcl–2 binding protein with anti–cell death activity", *Cell* 80:279–284.

Tanaka et al., 1993, "Sustained activation of vascular cells and leukocytes in the rabbit aorta after balloon injury", *Circulation* 88:1788–1803.

Tsujmoto et al., 1984, "Cloning of the chromosome breakpoint of neoplastic α cells with the t(14;18) chromosome translocation", *Science* 226:1097–1099.

Wallace & Miyada, 1987, "Oligonucleotide probes for the screening of recombinant DNA libraries", *Methods in Enzymology* 152:432–443.

Wang et al., 1981, "Selenium and myocardial infarction: Glutathione peroxidase in platelets", *Klin. Wochenschr.* 59:817–818.

Wieser et al., 1995, "GS domain mutation that constitutively activate TβR–I, the downstream signaling component in the TGF–β receptor complex", *EMBO J.* 14:2199–2208.

Wilson et al., 1994, "2.2 Mb of contiguous nucleotide sequence from chromosome III of *C. elegans*", *Nature* 368:32–38.

Wrana et al., 1994, "Mechanism of activation of the TGF–β receptor", *Nature* 370:341–347.

Xu et al., 1994, "Molecular cloning and functional expression of the bumetanide–sensitive Na–K–Cl cotransporter", *PNAS USA* 91:2201–2205.

Yoshimura et al., 1994, "The human plasma glutathione peroxidase–encoding gene: Organization, sequence and localization of chromosome 5q32", *Gene* 145:293–297.

Patrick Jr., et al., 1995, "Shear stress and cyclic strain moduclation of gene expression in vascular endothelial cells", *Blood Purification* 13:112–124.

Shyy et al., 1995, "Multiple cis–elements mediate shear stress–induced gene expression", *J. Biomechanics* 28:1451–1457.

Weatherall, D.J., 1995, "Scope and limitations of gene therapy", *British Medical Bulletin* 51:1–11.

Fuller et al., 1996, "Genetic Engineering of Cardiac Muscle Cells: In Vitro and In Vivo", *Seminars in Oncology* 23:4–21.

Mastrangelo et al., 1994, "Gene Therapy for Human Cancer: An Essay for Clinicians", 16:17–25.

Ngo et al., 1994, "Computational Complexity, Protein Structure Prediction, and the Levinthal Paradox", The Protein Folding Problem and Tertiary Structire Prediction, Merz et al., (ed.), Birkhausre, Boston, MA pp. 433–495.

Papadaki et al., 1997, "Effects of Fluid Shear Stress on Gene Regulation of Vascular Cells", *Biotechnol. Prog.* 13:209–221.

Arai, T. et al., 1998, "Genomic structure of the human Smad3 gene and its infrequent alterations in colorectal cancers", *Cancer Lett.* 122(1–2):157–163.

Baldwin et al., 1993, "Growth Inhibition of Human Pancreatic Carcinoma Cells by Transforming Growth Factor Beta–1", *Growth Factors*, 8:23–34.

Baldwin et al., 1996, "Attenuated ALK5 Receptor Expression in Human Pancreatic Cancer: Correlation with Resistance to Grwoth Inhibition", *Int. J. Cancer* 67:283–288.

Boyer, J.C. et al., 1995, "Microsatellite Instability, Mismatch Repair Deficiency, and Genetic Defects in Human Cancer Cell Lines", *Cancer Res.* 55:6063–6070.

Dennler, S. et al., 1998, "Direct binding of Smad3 and Smad4 to critical TGF–β–inducible elements in the promoter of human plasminogen activator inhibitor type–1 gene", *EMBO J.* 17(1):3091–3100.

DeCoteau, J.F. et al., 1997, "Loss of functional cell surface transforming growth factor β (TGF–β) type 1 receptor correlates with insensitivity of TGF–β in chronic lymphocytic leukemia", *PNAS USA* 94:5877–5881.

Eppert, K. et al., 1996, "MADR2 Maps to 18q21 and Encodes a $TGF^{SM}$–Regulated MAD–Related Protein That is Functionally Mutated in Colorectal Carcinoma", *Cell* 86:543–552.

Friess, H. et al., 1993, "Enhanced Expression of Transforming Growth Factor β Isoforms in Pancreatic Cancer Correlates with Decreased Survival", *Gastroenterology* 105:1846–1856.

Freeman, J.W. et al., 1995, "Increased tumorigenicity in the human pancreatic cell line MIA PaCa–2 is associated with an aberrant regulation of an IGF–1 autocrine loop and lack of expression of the TGF–β type RII receptor", *J. Cell Physiol.* 165:155–163.

Grau, A.M. et al., 1997, "Induction of $p21^{waf1}$ Expression and Growth Inhibition by Transforming Growth Factor β Involve the Tumor Suppressor Gene DPC4 in Human Pancreatic Adenocarcinoma Cells", *Cancer Res.* 57:3929–3934.

Grondahl et al., 1997, "Prognostic significance of PAI–1 and uPA in cytosolic extracts obtained from node–positive breast cancer patients", *Breast Cancer Res. Treat.* 43:153–(?).

Hahn, S.A. et al., 1996, "DPC4, A Candidate Tumor Suppressor Gene at Human Chromosome 18q21.1", *Science* 271:350–353.

Hannon, G. & Beach, D., 1994, "$p15^{INK4B}$ is a potential effector of TGF–β–induced cell cycle arrest", *Nature* 371:257–261.

Hata, A. et al., 1998, "Smad6 inhibits BMP/Smad1 signaling by specifically competing with the Smad4 tumor suppressor", *Genes & Development* 12:186–197.

Hata, A. et al., 1997, "Mutations increasing autoinhibition inactivate tumour suppressors Smad2 and Smad4", *Nature* 388(6637):82–87.

Hayashi, H. et al., 1997, "The MAD–Related Protein Smad7 Associates with the TGFβ Receptor and Functions as an Antagonist of TGFβ Signaling", *Cell* 89:1165–1173.

Heldin, C.H. et al., 1997, "TGF–β signaling from cell membrane to nucleus through SMAD proteins", *Nature* 390(6659):465–471.

Hoffman, R. et al., 1996, "Clinical Relevance of Urokinase Plasminogen Activator, Its Receptor, and Its Inhibitor in Patients with Renal Cell Carcinoma", *Cancer* 78:487–492.

Imamura, T. et al., 1997, "Smad6 inhibits signaling by the TGF–β superfamily", *Nature* 389:622–666.

Kadin, M.E. et al., 1994, "Loss of receptors for transforming growth factor β in human T–cell malignancies", *PNAS USA* 91:6002–6006.

Kim, I.Y. et al., 1996, "Genetic Change in Transforming Growth Factor β (TGF–β) Receptor Type I Gene Correlates with Insensitivity to TGF–β1 in Human Prostate Cancer Cells", *Cancer Res.* 56:44–48.

Korc et al., 1992, "Overexpression of the Epidermal Growth Factor Receptor in Human Pancreatic Cancer is Associated with Concomitant Increases in the Levels of Epidermal Growth Factor and Transforming Growth Factor Alpha", *J. Clin. Invest* 90:1352–1360.

Kornmann et al., 1998, "Inhibition of basal and mitogen–stimulated pancreatic cancer cell growth by cyclin D1 antisense is associated with loss of tumorigenicity and potentiation of cytotoxicity to cisplatinum", J. Clin. Invest. 101:344–352.

Liu, X. et al., 1997, "Transforming growth factor β–induced phosphorylation of Smad3 is required for growth inhibition and transcriptional induction in epithelial cells", PNAS USA 94:10669–10674.

Liu, X. et al., 1995, "Gene disruption of a G4–DNA–dependent nuclease in yeast leads to cellular senescence and telomere shortening", PNAS USA 92:6002–6006.

MacGrogan, D. et al., 1997, "Comparative mutational analysis of DPC4 (Smad4) in prostatic and colorectal carcinomas", Oncogene 15:1111–1114.

Maesawa, C. et al., 1997, "MAD–related Genes on 18q21.1, Smad2 and Smad4, Are Altered Infrequently in Esophageal Squamous Cell Carcinoma", Jpn. J. Cancer Res. 88:340–343.

Massague, J., 1990, "The Transforming Growth Factor β Family", Ann. Rev. Cell. Biol. 6:597–641.

Markowitz, S. et al., 1995, "Inactivation of the TypeII TGF–β Receptors in Colon Cancer Cells with Microsatellite Instability", Science 268:1336–1338.

Meyerhoff, L.L. et al., 1995, "A Transforming Growth Factor β Receptor Type II Gene Mutation Common in Colon and Gastric but Rare in Endometrial Cancers with Microsatellite Instability", Cancer Res. 55:5545–5547.

Nagatake, M. et al., 1996, "Somatic in Vivo Alterations of the DPC4 Gene at 18q21 in Human Lung Cancers", Cancer Res. 56:2718–2720.

Newfeld et al., 1996, "Mothers against dpp encodes a conserved cytoplasmic protein required in DPP/TGF–β responsive cells", Development 122:2099–2108.

Padgett, R.W. et al., 1998, "Smads Are the Central Component in Transforming Growth Factor–β Signaling", Pharm. Ther., 78(1);47–52.

Park, K. et al., 1994, "Genetic changes in the transforming growth factor β (TGF–β) type II receptor gene in human gastric cancer cells: Correlation with sensitivity to growth inhibition by TGF–β", PNAS USA 91:8772–8776.

Picon, A. et al., 1998, "A Subset of Metastic Human Colon Cancers Expresses Elevated Levels of Transforming Growth Factor α1[1]", Cancer Epidemiol. Biomarkers Prev. 7(6):497–504.

Powell, S.M. et al., 1997, "Inactivation of Smad4 in Gastric Carcinomas", Cancer Res. 57:4221–4224.

Raitano et al., 1993, "Tumor Necrosis Factor Up–regulates T–Interferon Binding in a Human Carcinoma Cell Line", J. Biol. Chem. 265:10466–10472.

Reiss, M., 1997, "Transforming Growth Factor–β and Cancer: A Love–Hate Relationship?", Oncol. Res. 9:447–457.

Riggins, G.J. et al., 1997, "Frequency of Smad Gene Mutations in Human Cancers", Cancer Res. 57(13):2578–2580.

Saitoh, M. et al., 1996, "Identification of Important Regions in the Cytoplasmic Juxtamembrane Domain of Type I Receptor That Separate Signaling Pathways of Transforming Grwoth Factor–β*", J. Biol. Chem. 271:2769–2775.

Schutte, M. et al., 1996, "DPC4 Gene in Various Tumor Types", Cancer Res 56:2527–2530.

Schmitt, M. et al., 1997, "Time–varying prognostic impact of tumour biological factors urokinase (uPA), PAI–1 and steroid hormone receptor status in primary breast cancer", Br. J. Cancer 76:306–311.

Serra, R. & Moses, H.L., 1996, "Tumor suppressor genes in the TGF–β signaling pathway", Nature Med. 2(4):390–391.

Sporn, M.B. & Roberts, A.B., 1992, "Transforming Growth Factor–β Recent Progress and New Challenges", J. Cell. Biol. 119:1017–1021.

Topper, J. et al., 1996, "Identification of vascular endothelial genes differentially responsive to fluid mechanical stimuli. Cyclooxygenase–2 manganese superoxide dismutase, and endothelial cell nitric oxide synthase are selectively up–regulated by steady laminar shear stress", PNAS USA 93:10417–10422.

Topper, J. et al., 1997, "Vascular MADs: Two novel MAD–related genes selectively inducible by flow in human vascular endothelium", PNAS USA 94:9314–9319.

Wagner, S.N. et al., 1996, "Type–1 Plasminogen Activator Inhibitor in Human Renal Cell Carcinoma", J. Pathol. 179:95–99.

Warshaw, A.L. et al., 1992, "Pancreatic Carcinoma", N. Engl. J. Med. 326:455–465.

Wang, J. et al., 1996, "Reduced Expression of Transforming Grwoth Factor β Type I Receptor Contributes to the Malignancy of Human Colon Carcinoma Cells", J. Biol. Chem. 271:17366–17371.

Waltz, D.A. et al., 1997, "Plasmin and Plasminogen Activator Inhibitor Type 1 Promote Cellular Motility by Regulating the Interaction between the Urokinase Receptor and Vitronectin", J. Clin. Invest. 100:58–67.

White, R.L., 1998, "Tumor Suppressing Pathways", Cell 92:591–592.

Wiersdorff et al., 1996, "Mad acts downstream of DPP receptors, revealing a differential requirement for dpp signaling in initiation and propagation of morphogenesis in the Drosophila eye", Development 122:2153–2162.

Yamamoto, H. et al., 1996, "Adenovirus–mediated Transfer of a Truncated Transforming Growth Factor–β (TGF–β) Type II Receptor Completely and Specifically Abolishes Diverse Signaling by TGF–β in Vascular Wall Cells in Primary Culture", J. Biol. Chem. 271:16253–16259.

```
                                                             GGCACGAGTCGGGAGCGGG
CGGAGGGGGAGGGGGAAAGAGGAGCGCAGGGTGAGAGTGAGCCGCAGGCTTCGGGAGGCGGAGGGGCGGGGAGCAGC
GCCGAGGYCGCCGCCTCCGCCTCCGCGCCTAGGACTAGGGGGTGGGGACGGACAAGCCCCG                                        4
                                                     M   P   G   E              4
                                                     ATG CCG GGG GAG           12

T   E   P   R   P   P   E   Q   Q   D   Q   E   G   E   A   A   K   A          24
ACG GAA GAG CCG AGA CCC CCG GAG CAG CAG GAC CAG GAA GGG GCA GCG AAG GCG         72

A   P   E   E   P   Q   Q   P   P   E   A   V   A   A   P   A   G   T          44
GCT CCG GAG GAG CCC CAA CAA CGG CCC CCT GAG GCG GTC GCG GCG CCT GCA GGG ACC    132

T   S   S   R   V   L   R   G   G   R   D   R   G   R   A   A   A   A          64
ACT AGC AGC CGC GTG CTG AGG GGA GGT CGG GAC CGA GGC CGG GCG GCC GCC GCC        192

A   A   V   S   R   R   R   K   A   E   Y   P   R   R   R   S   S   P          84
GCC GCA GCT GTG TCC CGC CGG AGG AAG GCC GAG TAT CCC CGC CGG CGG AGC AGC CCC    252

S   A   R   P   P   D   V   P   G   Q   Q   Q   Q   A   K   S   P   P         104
AGC GCC AGG CCT CCC GAC GTC CCC GGG CAG CAG CAG CAG GCC AAG TCC CCG TCT CCA    312

V   Q   G   K   K   S   P   R   L   L   C   I   E   K   V   T   T   D   K   D  124
GTT CAG GGC AAG AAG AGT CCG CGA CTC CTA TGC ATA GAA AAA GTA ACA ACT GAT AAA GAT 372

P   K   E   E   E   D   D   S   A   L   P   Q   E   V   S   I   A             144
CCC AAG GAA GAA GAA GAC GAT TCT GCC CTC CCT CAG GAA GTT TCC ATT GCT            432
```

FIG. 1A

```
A   S   R   P   S   R   G   W   R   S   S   R   T   S   V   S   R   H   R   D           164
GCA TCT AGA CCT AGC CGG GGC TGG CGT AGT AGT AGG ACA TCT GTT TCT CGC CAT CGT GAT         492

T   E   N   T   R   S   S   R   S   K   T   G   S   L   Q   L   I   C   K   S           184
ACA GAG AAC ACC CGA AGC TCT CGG TCC AAG ACC GGT TCA TTG CAG CTC ATT TGC AAG TCA         552

E   P   N   T   D   Q   Q   L   D   Y   D   V   G   E   H   Q   S   P   G   G           204
GAA CCA AAT ACA GAC CAA CTT GAT TAT GAT GTT GGA GAA CAT CAG TCT CCA GGT GGC             612

I   S   G   E   E   E   E   E   E   M   L   I   S   E   E   E   I                       224
ATT AGT GGT GAA GAG GAA GAG GAA GAG ATG TTA ATC AGT GAA GAG GAG ATA                     672

P   F   K   D   D   P   R   D   E   T   Y   K   E   R   E   T   P                       244
CCA TTC AAA GAT GAT CCA AGA GAT GAG ACC TAC AAA GAA AGG GAA ACC CCA                     732

K   P   R   R   K   S   G   K   V   K   E   E   N   E   K   E   I   K   V               264
AAG CCA CGG AGA AAA TCA GGG AAG GTA AAA GAA GAG AAT GAA AAG GAA ATT AAA GTG             792

E   V   E   V   E   V   K   E   E   E   D   D   E   D   E   E   P   P                   284
GAA GTA GAG GTG GAG GTG AAA GAA GAG GAG GAT GAT GAG GAT GAG GAA CCT CCA                 852

R   K   R   G   R   R   R   K   D   D   K   S   P   R   L   P   K   R   R   K           304
AGG AAG AGA GGA AGA AGA CGA AAA GAT GAC AAA AGT CCA CGT TTA CCC AAA AGG AGA AAA         912

K   P   P   I   Q   Y   V   R   C   E   M   E   G   C   G   T   V   L   A   H           324
AAG CCT CCA ATC CAG TAT GTC CGT TGT GAG ATG GAA GGA TGT GGA ACT GTC CTT GCC CAT         972
```

FIG. 1B

```
P   R   L   Q   H   H   I   K   Y   Q   H   L   L   K   K   Y   V   C    344
CCT CGC TAT TTG CAG CAC CAC ATT AAA TAC CAG CAT TTG CTG AAG AAG TAT GTA TGT  1032

P   H   P   S   C   G   R   L   F   R   L   Q   K   Q   L   R   H   A   K    364
CCC CAT CCC TCC TGT GGA CGA CTC TTC AGG CTT CAG AAG CAA CTT CGA CAT GCC AAA  1092

H   H   T   D   Q   R   D   Y   I   C   E   Y   C   A   R   A   F   K   S   S    384
CAT CAT ACA GAT CAA AGG GAT TAT ATC TGT GAA TAT TGT GCT CGG GCC TTC AAG AGT TCC  1152

H   N   L   A   V   H   R   M   I   H   T   G   E   K   P   L   Q   C   E   I    404
CAC AAT CTG GCA GTG CAC CGG ATG ATT CAC ACT GGC GAG AAG CCA TTA CAA TGT GAG ATC  1212

C   G   F   T   C   R   Q   K   Q   N   W   H   M   K   K   F   E   K   D   A    424
TGT GGA TTT ACT TGT CGA CAA AAG CAA ATG TGG CAC ATG AAG AAA TTT GAG AAG GAC GCA  1272

D   S   F   Y   Q   F   S   C   N   I   C   G   K   K   F   E   K   D   A   S    444
GAC TCC TTC TAC CAG TTT TCT TGC AAT ATC TGT GGC AAA AAA TTT GAG AAG GAC AGC AGC  1332

V   A   H   K   A   L   I   T   S   T   D   I   L   G   T   N   P   E   S   L   T    464
GTA GCA CAC AAG GCA GCC CTC ATC ACC AGC ACA GAT ATC TTG GGC ACT AAC CCA GAG TCC CTG ACG  1392

N   A   G   A   L   I   P   L   L   P   E   P   L   G   N   T   S    484
AAT GCA GGC GCC CTC ATC ACC AGC ACA GAT ATC TTG CCT CTT CCT GAG CCC TTG GGA AAC TCA ACC  1452

Q   P   S   D   G   Q   G   L   P   L   L   P   E   P   L   G   N   T   S    504
CAG CCT TCA GAT GGT CAG GGT CTT CCT CTT CCT GAG CCC TTG GGA AAC TCA ACC TCT  1512
```

FIG.1C

```
     G   E   C   L   L   L   E   A   E   G   M   S   K   S   Y   C   S   G   T   E   524
    GGA GAG TGC CTA CTG TTA GAA GCT GAA GGG ATG TCA AAG TCA TAC TGC AGT GGG ACG GAA  1572

R   V   S   L   M   A   D   G   K   I   F   V   G   S   S   G   G   T          544
    CGG GTG AGC CTG ATG GCT GAT GGG AAG ATC TTT GTG GGA AGC AGT GGA GGC ACT          1632

E   G   L   V   M   N   S   D   I   L   G   A   T   T   E   V   L   I   E   D  564
    GAA GGG CTG GTT ATG AAC TCA GAT ATA CTC GGT GCT ACC ACA GAG GTT CTG ATT GAA GAT  1692

S   D   S   A   G   P   *                                                       570
    TCA GAC TCT GCC GGA CCT TAG TGGACAGGAAGACTTGGGGCATGGGACAGCTCAGACTTTGTATTTAAAAGT  1761

TAAAAAGGACAAAAAAAAAAAAAAAAAA                                                     1791
```

FIG.1D

GCACGAGCGGGAGAGCCGCGCAGGGGCGCCGCGGGGTGGGGCAGCCGGAGCGCA
GGCCCCGATCCCGGGGGCGCCCCGGGCGCCCCGGCCTCCGGGAGACTGGCGCATGCCACGGAGCG
CCCCTCGGGCCGCCGCCGCTCCTGCCGGGCCCCTGCTGCTGCTGTGCCTGCTGCCCTGCCCCAACTCGGCGCC

```
                                                                            M   F         2
CGACTCACAAAGAAACATCATGTTCGCTCCTTAGCAGGCAAACGACTTTTCTCCTGCCTCCTCGCCCGC ATG TTC         6

R   T   K   R   S   A   L   V   R   R   L   W   R   S   R   A   P   G   G   E        22
AGG ACC AAA CGA TCT GCG CTC GTC CGG CGT CTC TGG AGG AGC CGT GCG CCC GGC GGC GAG        66

D   E   E   G   A   G   G   A   G   G   G   G   G   P   G   R   A   G   C   L        42
GAC GAG GAG GGC GCA TCT GGG GGA GGT GGA GGC GGT GGC GGG CCG AGG GCT TGC CTG        126

T   D   S   R   A   H   G   A   K   G   H   H   H   P   H   P   P   A   G   A        62
ACG GAC AGC CGA GCG CAT GGG GCC AAA GGT CAC CAC CAT CCC CAC CCG CCA GCC GCG        186

G   K   A   V   R   G   A   E   A   D   L   K   A   L   T   H   S   V   L   K        82
GGC AAG GCG GTG CGA GGT GCC GAG GCG GAT CTG AAG GCG CTC ACG CAC TCG GTG CTC AAG        246

G   A   A   G   G   A   E   G   G   L   L   L   Q   A   V   E   S   R   G   T        102
GGC GCG GCC GGG GCC GAG GGC GGC CTG CTC CTG CAG GCC GTG GAG TCC CGC GGG ACG        306

L   K   E   R   Q   L   E   L   E   L   K                                              122
CTG AAG GAG CGG CAG CTG GAG CTG GAG CTG AAG                                             366
```

FIG.2A

```
T   A   C   L   L   P   G   R   L   D   C   R   L   G   P   G   A   P   A    142
ACC GCG TGC CTC CTG CCC GGC CGC CTG GAC TGC AGG CTG GGC CCG GCG GCC CCC GCC  426

G   A   Q   P   A   Q   P   P   S   S   Y   S   L   P   L   L   C   K   V    162
GGC GCG CAG CCT GCG CAG CCG CCC TCG TCC TAC TCG CTC CCC CTG CTG TGC AAA GTG  486

F   R   W   P   D   L   R   H   S   E   V   K   R   L   C   C   E   S   S    182
TTC AGG TGG CCG GAT CTC AGG CAT TCC GAA GTC AAG AGG CTG TGC TGT GAA TCT      546

Y   G   K   I   N   P   E   L   V   C   C   N   P   H   H   L   S   R   L    202
TAC GGG AAG ATC AAC CCC GAG CTG GTG TGC TGC AAC CCC CAT CAC CTT AGC CGA TGC  606

E   L   E   S   P   P   P   P   Y   S   R   Y   P   M   D   F   L   K   P    222
GAA CTA GAG TCT CCC CCT CCT TAC TCC AGA TAC CCG ATG GAT TTT CTC AAA CCA ACT  666

A   D   C   P   D   A   V   P   S   S   L   L   E   T   G   G   T   N   Y    242
GCA GAC TGT CCA GAT GCT GTG CCT TCC TCC CTT CTT GAA ACA GGG GGA ACG AAT TAT  726

L   A   P   G   G   L   S   D   S   Q   L   L   E   P   G   D   R   S   H    262
CTG GCC CCT GGG GGG CTT TCA GAT TCC CAA CTT CTT GAG CCT GGG GAT CGG TCA CAC  786

W   C   V   Q   E   P   P   G   V   A   Y   W   E   E   K   T   R   V   G    282
TGG TGC GTG CAG GAG CCC CCT GGA GTG GCA TAC TGG GAG GAG AAG ACG AGA GTG GGG  846

R   L   Y   C   L   G   Q   S   L   D   I   F   Y   D   L   P   Q   G   N    302
AGG CTC TAC TGT CTC GGA CAG TCT CTG GAT ATC TTC TAT GAT CTA CCT CAG GGG AAT  906

G   F   C   L   Q   P   N   906
GGC TTT TGC CTC CAG CCC AAT
```

FIG.2B

| | | | | | | | | | | | | | | | | | | | | |
|---|---|---|---|---|---|---|---|---|---|---|---|---|---|---|---|---|---|---|---|---|
| S | D | N | K | S | Q | L | V | Q | K | V | R | S | K | I | G | C | G | I | Q | 322 |
| TCG | GAC | AAC | AAG | AGT | CAG | CTG | GTG | CAG | AAG | GTG | CGG | AGC | AAA | ATC | GGC | TGC | GGC | ATC | CAG | 966 |
| L | T | R | E | V | D | G | V | W | V | Y | N | R | S | S | Y | P | I | F | I | 342 |
| CTG | ACG | CGG | GAG | GTG | GAT | GGT | GTG | TGG | GTG | TAC | AAC | CGC | AGC | AGT | TAC | CCC | ATC | TTC | ATC | 1026 |
| K | S | A | T | L | D | N | P | D | S | R | T | L | L | V | H | K | V | F | P | 362 |
| AAG | TCC | GCC | ACA | CTG | GAC | AAC | CCT | GAC | TCC | AGG | ACG | CTG | TTG | GTA | CAC | AAG | GTG | TTC | CCC | 1086 |
| G | F | S | I | K | A | F | D | Y | E | K | A | Y | S | L | Q | R | P | N | D | 382 |
| GGT | TTC | TCC | ATC | AAG | GCT | TTC | GAC | TAC | GAG | AAG | GCG | TAC | AGC | CTG | CAG | CGG | CCC | AAT | GAC | 1146 |
| H | E | F | M | Q | Q | P | W | T | G | F | T | V | Q | I | S | F | V | K | G | 402 |
| CAC | GAG | TTT | ATG | CAG | CAG | CCG | TGG | ACG | GGC | TTT | ACC | GTG | CAG | ATC | AGC | TTT | GTG | AAG | GGC | 1206 |
| W | G | Q | C | Y | T | R | Q | F | I | S | S | C | P | C | W | L | E | V | I | 422 |
| TGG | GGT | CAG | TGC | TAC | ACC | CGC | CAG | TTC | ATC | AGC | AGC | TGC | CCG | TGC | TGG | CTA | GAG | GTC | ATC | 1266 |
| F | N | S | R | * | | | | | | | | | | | | | | | | 426 |
| TTC | AAC | AGC | CGG | TAG | CCGCGTGCGGAGGGACAGAGCGTGAGCTGAGCAGGCCACACTTCAAACTACTTTGCT | | | | | | | | | | | | | | | | 1278 |

GCTAATATTTCCTCCTGAGTGCTTGCTTGTCTCTTTTTTTTTTTGTTTGTTGGTTGGTTTTCT

TCTTCTCGTCCTCGTTTGTGTTCTGTTTGCTCTGTTTGCTCTGTTTGAGAAATAGCTTATGAAAGAATTGTTGGGGTTTTTT

TGGAAGAAGGGGCAGGTATGATCGGCAGGACACCCTGATAGGAAGAGAGGGGAAGCAGAAATCCAAGCACCACCAAACACA

FIG. 2C

```
GTGTATGAAGGGGGGGGGTCATCATTTCACTTGTCAGGAGTGTGTGAGTGTGAGTGTGCGGCTGTGTGCACGCGT
GTGCAGGAGCGGCAGATGGGGAGACAACGTGCTCTTTGTTTGTGTCTCTTATGGATGTCCCAGCAGAGAGGTTTGCA
GTCCCAAGCGGTGTCTCTCCTGCCCCTTGGACACGCTCAGTGGGGCAGAGGCAGTACCTGGGCAAGCTGGGCTGGGG
TCCCAGCAGCTGCCAGGAGCACGGCTCTGTCCCCAGCCTGGGAAAGCCCCTGCCCTCCTCTCCCTCATCAAGGACACG
GGCCTGTCCACAGGCTTCTGAGCAGCGAGCCTGCTAGTGGCCGAACCAGAACCAATTATTTTCATCCTTGTCTTATTCC
CTTCCTGCCAGCCCCTGCCATTGTAGCGTCTTTCTTTTTTGGCCATCTGCTCCTGGATCTCCCTGAGATGGGCTTCCCA
AGGGCTGCCGGGGCAGCCCCTCACAGTATTGCTCACCCAGTGCCCTCTCCCCTCAGCCTCTCCCCTGCCCTGCCCTGGT
GACATCAGGTTTTTCCCGGACTTAGAAAACCAGCTCAGCACTGCCTGCTCCCATCCTGTGTGTTAAGCTCTGCTATTAG
GCCAGCAAGCGGGGATGTCCCTGGGAGGGACATGCTTAGCAGTCCCCTTCCCTCCAAGAAGGATTTGGTCCGTCATAAC
CCAAGGTACCACCATCCTAGGCTGACACCTAACTCTTCTTTCATTTCTTCTACAACTCATACACTGTATGATACTTCGACA
CTGTTCTTAGCTCAATGAGCATGTTTAGACTTAACATAAGCTATTTTCTAACTACAAAGGTTTAAATGAACAGAGA
AGCATTCTCATTGGAAATTTAGCATTGTAGTGCTTTGAGAGAGAAAGGACTCCTGAAAAAAAACCTGAGATTTATTAAA
GAAAAAAATGTATTTTATGTTATATATAAATATATTATTACTGTAAATATAAAGACGTTTTATAAGCATCATTATTTA
```

FIG.2D

TGTATTGTGCAATGTGTATAAACAAGAAAATAAGAAAAGATGCACTTTGCTTTAATATAAATGCAAATAACAAATGC

CAAATTAAAAAGATAAACACAAGATTGGTGTGTTTTTCCTATGGGTGTTATCACCTAGCTGAATGTTTTCTAAAGGAG

TTTATGTTCCATTAAACGATTTTTAAAATGTACACTTGAAAAAAAAAAAAAAAAAA

FIG.2E

```
                    GGCACGAGGTTGCCCTGGCGGAGCAGAGACAGGCCCTGGGGTGGAGGTC

M   C   N   T   P   T   Y   C   D   L                          10
TTTGGTTTCATAAGAGCCTGAGAGAGATTTTTCTAAGAT ATG TGT AAC ACA CCA ACG TAC TGT GAC CTA    30

G   K   A   A   K   D   V   F   N   K   G   Y   G   F   G   M   V   K   I   D     30
GGA AAG GCT GCT AAG GAT GTC TTC AAC AAA GGA TAT GGC TTT GGC ATG GTC AAG ATA GAC    90

L   K   T   K   S   C   S   G   V   E   F   S   T   S   G   H   A   Y   T   D     50
CTG AAA ACC AAG TCT TGT AGT GGA GTG GAA TTT TCT ACT TCT GGT CAT GCT TAC ACT GAT   150

T   G   K   A   S   G   N   L   E   T   K   Y   K   V   C   N   Y   G   L   T     70
ACA GGG AAA GCA TCA GGC AAC CTA GAA ACC AAA TAT AAG GTC TGT AAC TAT GGA CTT ACC   210

F   T   Q   K   W   N   T   D   N   T   L   G   T   E   I   S   W   E   N   K     90
TTC ACC CAG AAA TGG AAC ACA GAC AAT ACT CTA GGG ACA GAA ATC TCT TGG GAG AAT AAG   270

L   A   E   G   L   K   L   T   D   T   I   F   V   P   N   T   G   K   K   D    110
TTG GCT GAA GGG TTG AAA CTG ACT GAT ACC ATA TTT GTA CCG AAC ACA GGA AAG AAG GAT   330

S   G   K   L   K   A   S   Y   K   R   D   C   F   S   V   G   S   N   V   D    130
AGT GGG AAA TTG AAG GCC TCC TAT AAA CGG GAT TGT TTT AGT GTT GGC AGT AAT GTT GAT   390

I   D   F   S   G   P   T   I   Y   G   W   A   V   L   A   F   E   G   W   L    150
ATA GAT TTT TCT GGA CCA ACC ATC TAT GGC TGG GCT GTG TTG GCC TTC GAA GGG TGG CTT   450
```

FIG.3A

```
A   G   Y   Q   M   S   F   D   T   A   K   S   K   L   S   Q   N   N   F   A    170
GCT GGC TAT CAG ATG AGT TTT GAC ACA GCC AAA TCC AAA CTG TCA CAG AAT AAT TTC GCC   510

L   G   Y   K   A   A   D   F   Q   L   H   T   H   V   N   D   G   T   E   F    190
CTG GGT TAC AAG GCT GCG GAC TTC CAG CTG CAC ACA CAT GTG AAC GAT GGC ACT GAA TTT   570

G   G   S   I   Y   Q   K   V   N   E   K   I   E   T   S   I   N   L   A   W    210
GGA GGT TCT ATC TAC CAG AAG GTG AAT GAG AAG ATT GAA ACA TCC ATA AAC CTT GCT TGG   630

T   A   G   S   N   N   T   R   F   G   I   A   K   Y   M   L   D   C   R        230
ACA GCT GGG AGT AAC AAC ACC CGT TTT GGC ATT GCT GCT AAG TAC ATG CTG GAT TGT AGA   690

T   S   L   S   A   K   V   N   A   S   L   I   G   L   G   Y   T   Q   T        250
ACT TCT CTC TCT GCT AAA GTA AAT AAT GCC AGC CTG ATT GGA CTG GGT TAT ACT CAG ACC   750

L   R   P   G   V   K   L   T   L   S   A   L   I   D   G   K   N   F   S   A    270
CTT CGA CCA GGA GTC AAA TTG ACT TTA TCA GCT TTA ATC GAT GGG AAG AAC TTC AGT GCA   810

G   G   H   K   V   G   L   G   F   E   L   E   A   *                             283
GGA GGT CAC AAG GTT GGC TTG GGA TTT GAA CTG GAA GCT TAA TGTGGTTTGAGGAAAGCATCAGA   849

TTTGTCCCTGAAGTGAAGAGAAATGAACCCACTATGTTTGGCCTTAAAATTCTTCTGTGAAATTCAAAAGTGTGAA

CTTTTTATTCTTCCAAAGAATTGTAATCCTCCCCACACTGAAGTCTAGGGGTTGCGAATCCCTCCTGAGGGAGACGCTT

GAAGGCATGCCTGGAAGTTGTCATGTTTGTGCCACGTTTCAGTTCTCAGTTCTGAAGTGTTATTAAATGTGTTCCTCAGCG
```

FIG.3B

ACAGTGTAGCGTCATGTTTAGAGGAGACGATCTGACCCACCAGTTTGTACATCACGTCCTGCATGTCCCACACCATTTTT

TCATGACCTTGTAATATACTGGTCTCTGTGCTATAGTGGAATCTTTGGTTTTGCATCATAGTAAATAAAATAAACCCA

TCACATTTGGAACATAAAAAAAAAAAAAAAAAA

FIG. 3C

| T | S | L | A | L | V | L | N | L | L | Q | I | Q | R | N | V | T | L | F | P | 20 |
|---|---|---|---|---|---|---|---|---|---|---|---|---|---|---|---|---|---|---|---|---|
| ACG | AGC | CTA | GCC | CTG | GTG | CTC | AAC | CTG | CTG | CAG | ATC | CAG | AGG | AAT | GTC | ACT | CTC | TTC | CCC | 60 |

| E | E | V | I | A | T | I | F | S | S | A | W | V | P | P | C | G | T |  |  | 40 |
|---|---|---|---|---|---|---|---|---|---|---|---|---|---|---|---|---|---|---|---|---|
| GAG | GAG | GTG | ATC | GCC | ACC | ATC | TTT | TCC | TCC | GCC | TGG | GTC | CCC | CCT | TGC | TGC | GGG | ACA |  | 120 |

| A | A | V | V | G | L | L | Y | P | C | I | D | S | H | L | G | E | P | H |  | 60 |
|---|---|---|---|---|---|---|---|---|---|---|---|---|---|---|---|---|---|---|---|---|
| GCA | GCT | GCT | GTT | GGC | CTA | CTG | TAC | CCC | TGT | ATC | GAC | AGT | CAC | CTC | GGA | GAA | CCC | CAC |  | 180 |

| K | F | K | R | E | W | A | S | V | M | R | C | I | A | V | F | V | G | I | N | 80 |
|---|---|---|---|---|---|---|---|---|---|---|---|---|---|---|---|---|---|---|---|---|
| AAA | TTT | AAG | AGA | GAA | TGG | GCC | AGT | GTC | ATG | CGC | TGC | ATA | GCA | GTT | TTT | GTT | GGC | ATT | AAC | 240 |

| H | A | S | A | K | L | D | F | A | N | N | F | D | R | S | L | T | L | A | A | 100 |
|---|---|---|---|---|---|---|---|---|---|---|---|---|---|---|---|---|---|---|---|---|
| CAC | GCC | AGT | GCT | AAA | TTG | GAT | TTT | GCC | AAT | AAT | GTC | CAG | CGT | TCC | TTG | ACT | TTA | GCA | GCC | 300 |

| L | S | L | G | L | W | T | L | A | T | L | I | T | Q | S | R | S | G | L | G | I | 120 |
|---|---|---|---|---|---|---|---|---|---|---|---|---|---|---|---|---|---|---|---|---|---|
| CTA | TCT | TTG | GGC | CTT | TGG | ACA | CTG | GCT | ACG | CTG | ATC | ACG | CAG | CAG | AGT | CGT | TCC | AGA | GGC | CTT | GGG | ATC | 360 |

| T | I | A | F | L | Y | I | R | S | W | L | P | C | I | F | F | N | G | V | Y | Q | 140 |
|---|---|---|---|---|---|---|---|---|---|---|---|---|---|---|---|---|---|---|---|---|---|
| ACC | ATA | GCT | TTT | CTA | TAT | ATT | CGT | TCT | TGG | CTC | CCT | TGT | ATA | TTT | TTC | AAT | GGT | GTG | TAT | CAG | 420 |

| Y | T | S | P | D | F | L | Y | L | R | Q | L | A | M | G | V | P | E | K | P | H | 160 |
|---|---|---|---|---|---|---|---|---|---|---|---|---|---|---|---|---|---|---|---|---|---|
| TAT | ACA | TCC | CCA | GAT | TTC | CTC | TAT | ATT | CGT | CAG | CAG | TTA | GCT | ATG | GGT | GTT | CCT | GAA | AAG | CCC | CAT | 480 |

| G | V | T | V | G | N | I | G | R | Q |  |  |  |  |  |  |  |  |  |  | 180 |
|---|---|---|---|---|---|---|---|---|---|---|---|---|---|---|---|---|---|---|---|---|
| GGC | GTC | ACG | GTG | GGG | AAC | ATA | GGA | CGA | CAG |  |  |  |  |  |  |  |  |  |  | 540 |

FIG.4A

```
                                                          182
                                                          546
  S   D   *
  AGT GAT TGA GTCTTCAAAACCACCGATTCTGAGAGCAAGGAAGATTTTGGAAGAAAATCTGACTGTGGATTATGAC

AAAGATTATCTTTTTCTTAAGTAATCTATTTAGATCGGGCTGACTGTACAAATGACTCCTGAAAAAACTCTTCACCT

AGTCTAGAATAGGGAGGTGGAGAATGATGACTTACCCTGAAGTCTTCCCTTGACTGCCCGCACTGGCGCCTGTCTGTGC

CCTGGAGCATTCTGCCCAGGCTACGTGGGTTCAGGCAGGTGGCAGCTTCCCAAGTATTCGATTTCATTCATGTGATTAA

AACAAGTTGCCATATATTTCAAAAAAAAAAAAAAMCTCGAGACCAACCCGCAGTTTTGTGTCAGTGCCCAAGGAGGT

AGGTTGATGGTGCTTAACAAACATGAAGTATGGTGTAATAGGAATAATATTTATCCNAAAGATTTTAAAAATAGGGCT

GTGTTTAAAAAAAAAAAAAAAAAAAA
```

FIG. 4B

```
M   C   H   S   R   S   C   H   P   T   M   T   I   L   Q   A   P   T   P   A              20
ATG TGT CAC TCT CGC AGC TGC CAC CCG ACC ATG ACC ATC CTG CAG GCC CCG ACC CCG GCC             60

P   S   T   I   P   G   P   R   R   G   S   G   P   E   I   F   T   F   D   P              40
CCC TCC ACC ATC CCG GGA CCC CGG CGG GGC TCC GGT CCT GAG ATC TTC ACC TTC GAC CCT            120

L   P   E   P   A   A   A   P   A   G   R   P   S   A   S   R   G   H   R   K              60
CTC CCG GAG CCC GCA GCG GCC CCT GCC GGG CGC CCC AGC GCC TCT CGC GGG CAC CGA AAG            180

R   S   R   R   V   L   Y   P   R   V   V   R   Q   L   P   V   E   E   P                  80
CGC AGC CGC AGG GTT CTC TAC CCT CGA GTG GTC CGG CAG CTG CCA GTC GAG GAA CCG                240

N   P   A   K   R   L   L   F   L   L   T   I   V   F   C   Q   I   L   M                 100
AAC CCA GCC AAA AGG CTT CTC TTT CTG CTC ACC ATC GTC TTC TGC CAG ATC CTG ATG                300

A   E   G   V   P   A   P   L   P   P   E   D   A   P   N   A   A   S   L                 120
GCT GAA GAG GGT GTG CCG GCG CCC CTG CCT CCA GAG GAC GCC CCT AAC GCC GCA TCC CTG            360

A   P   T   P   V   S   P   V   L   E   P   F   N   L   T   S   E   P   S   D             140
GCG CCC ACC CCT GTG TCC CCC GTC CTC GAG CCC TTT AAT CTG ACT TCG GAG CCC TCG GAC            420

Y   A   L   D   L   S   T   F   L   Q   Q   H   P   A   A   F   *                         157
TAC GCT CTG GAC CTC AGC ACT TTC CTC CAG CAA CAC CCG GCC GCC TTC TAA                        471

CTGTGACTCCCCGCACTCCCCAAAAGAATCCGAAAAGAAGACCACCACAAGAAAACCAGGCGTACCTGGTGCGGAGAGCGTA         550
```

FIG.5A

```
TCCCCAACTGGGACTTCCGAGGCAACTTGAACTCAGAGACACTACAGCGGAGACGCCACCCGGTGCTTGAGGCGGGACCG    629
AGGGCGCACAGAGACCGAGGCGCATAGAGACCGAGGCACAGCCCAGCTGGGGCTAGGCCCGGTGGGAAGGAGAGCGTCGT    708
TAATTTATTTCTTATTGCTCCTAATTAATATATTTATGTATTTATGTACGTCCTCCTAGGTGATGGAGATGTGTACGTA    787
ATATTTATTTTAACTTATGCAAGGGTGTGAGATGTTCCCTCTGCTGTAAATGCAGGTCTCTTGGTATTTATTGAGCTTT    866
GTGGGACTGGTGGAAGCAGGAGACACCTGGAACTGCGGCAAAGTAGGAGAAGAAATGGGGAGGACTCGGGTGGGGAGGAC    945
GTCCCGGCTGGGATGAAGTCTGGTGGTCGTAAGTTTAGGAGGTGACTGCATCCTCCAGCATCTCAACTCCGTCTG      1024
TCTACTGTGTGAGACTTCGGCGGACCATTAGGAATGAGATCCGTGAGATCCTTCCATCTTCTTGAAGTCGCCTTTAGGG    1103
TGGCTGCGAGGTAGAGGGTTGGGGGTTGGTGGGCTGTCACGGAGCGACTGTCGAGATCGCCTAGTATGTTCTGTGAACA    1182
CAAATAAAAATTGATTTACTGTCAAAAAAAAAAAAAACTCGAG    1228
```

FIG.5B

```
GAATTCGGCACGAGGMCAGGAGCTCCTTTWCTGGCTCTCCCATCATGGGGCTTAGGGTTGAGTCTTCA          68
GGTTCTGGGGGCAGGAAGGACGGGCACTCAGGAGGCCCCCTCCCATCCACAGCCCCTCTTTGGGAGGGGGAAACTTG  147
GCAACCCGGGGAGGCATGTGGATCTTTTCCTAAGCAAGATGCTGAGCTGGAAAGATGGGGGTGTAAGGTAATGTCCCAAA  226
CTGAAACTTTGCCAGGCACTGGGAGGAGGCTGTGAACTCTTTTCTGGCTTTAGAATTTAGGTCTAGATCCCAAAGGCTA  305
AGTACCCCCTGGGGCTAACCAGAGGCATGCCTGGGCTGAGCTGAACCTTCTGGTGCACTGGCCCCTGGCTGACTGCTC  384
TTCTGCAGGAAGTTGGAGGAGATTCCTGAAGTTGATTCCTCAGGCTGGATGTCCAAGGGGGTTGGAGTTTCTGATGTCT  463
TTCTGTCTCCCTCTCTTTCTTTCTCCCTACCAGGTCCACTCTTCTTCAGAGGGGCCTGCGGTGCTCTAAAAGTTCTC    542
CTGTTAAAAGTTTAGAGCAAATTGGTTATTATTTTAAAATCAATAAAACTTTAAAAGTACTAAGACAACTTCTAAGAGG  621
GGAGTGGACAGAGGGCCTGGTGGCAGCTCACAGTTTCTTTTTCTGACCTTTGGTCTCACCCAAGTGTCCCACCTGAG    700
TGCCCACCTTGCCCACCTGAGGTAATGCCCTGGGCTCCACCAGTCCAGATCCACAGGGCGCAGCCATGTGGGAGTGGC  779
GGCTGATTGTTACCCAGTAGTGTTGATAGCACATTATTCATAACAGCCAAGAGAGGAAGCAACCCAAATGTCCATTAG   858
CTGATAAAATGGATAAATGAAATATGGTACGTCCGAAGAATGGAATATCATTCACCCTGAAAAAGAACGAAGTCCAGCA  937
CCAAAACGTGCTACAACATGGATGAACTTCGATGACTTTGTGCCACACTGAAAAGAAGAAGCCAGCCACAAAAGGCCATAT 1016
```

FIG.6A

```
                  M   S   R   M   G   K   P   I   E   T   Q   K   S   P   P   P    16
ATTGTATGAAATGAA ATG TCC AGA ATG GGC AAA CCC ATA GAG ACA CAA AAA TCT CCG CCA CCT  1079

P   Y   S   R   L   S   P   R   D   E   Y   K   P   L   D   S   D   S   T        36
CCC TAC TCT CGG CTG TCT CCT CGC GAC GAG TAC AAG CCA CTG GAT TCC GAT TCC ACA     1139

L   S   Y   T   E   T   E   A   T   N   S   L   I   I   T   A   P   G   E   F   S    56
TTG TCT TAC ACT GAA ACG GAG GCT ACC AAC TCC CTC ATC ACT GCT CCG GGT GAA TTC TCA  1199

D   A   S   M   S   P   D   A   T   K   P   K   S   H   W   C   S   V   A   Y   W    76
GAC GCC AGC ATG TCT CCG GAC GCC ACC AAG CCG AGC CAC TGG TGC AGC GTG GCG TAC TGG  1259

E   H   R   T   R   V   G   G   S   G   R   L   Y   A   V   D   Q   A   V   S   I   F    96
GAG CAC CGG ACG CGG GTG GGC GGC AGC GGC CGC CTC TAT GCG GTG GAC CAG GCC GTC AGC ATC TTC  1319

Y   D   L   P   Q   P   Q   G   L   G   Q   L   N   L   L   S   E   Q   R   S   116
TAC GAC CTA CCT CAG CCT CAG GGC CTG GGC CAG CTC AAC CTG CTC AGC GAG CAG CGC AGC  1379

E   S   V   R   R   T   R   S   K   I   G   F   G   I   L   L   V   K   E   P   136
GAG TCG GTG CGG CGA ACG CGC AGC AAG ATC GGC TTC GGC ATC CTC CTG GTC AAG GAG CCC  1439

D   G   V   W   A   Y   N   R   G   E   H   P   I   F   V   N   S   P   T   L   156
GAC GGC GTG TGG GCC TAC AAC CGC GGC GAG CAC CCC ATC TTC GTC AAC TCC CCG ACG CTG  1499

D   A   P   G   R   A   L   V   V   R   K   V   P   P   G   Y   S   I   K        176
GAC GCG CCC GGC CGC GCC CTG GTC GTC CGC AAG GTG CCC CCC GGC TAC TCC ATC AAG     1559
```

FIG.6B

```
    V   F   D   F   E   R   S   G   L   Q   H   A   P   E   P   D   A   A   D   G        196
   GTG TTC GAC TTC GAG CGC TCG GGC CTG CAG CAC GCG CCC GAG CCC GAC GCC GCC GAC GGC       1619

P   Y   D   P   N   S   V   R   I   S   F   A   K   G   W   G   P   C   Y   S        216
   CCC TAC GAC CCC AAC AGC GTC CGC ATC AGC TTC GCC AAG GGC TGG GGG CCC TGC TAC TCC       1679

R   Q   F   I   T   S   C   P   C   W   L   E   I   L   L   N   N   P   R   *        236
   CGG CAG TTC ATC ACC TCC CCC TGC TGC TGG CTG GAG ATC CTC CTC AAC AAC CCC AGA TAG       1739

TGGGGGCCCCGGCGGGAGGGGCGGGTGGGAGGCCGGCGGGCCACCGCCACCTGCCGGCCTCGAGAGGGGCGATGCCCAGA      1818

GACACAGCCCCCACGGACACAAACCCCCAGATATCATCTACCTAGATTTAATATAAAGTTTTATATATTATATGGAAAT      1897

ATATATTATACTTGTAATTATGGAGTCATTTTTACAATGTAATTATTTATGTATGGTGCAATGTGTGTATATGGACAAA      1976

ACAAGAAAGACGCACTTTGGCTTATAATTCTTTCAATACAGATATATTTCTTTCTCCTCCTTCCTCCTTACT             2055

TTTTATATATATATAAAGAAAATGATACAGAGAGCTAGGTGGAAAAGCCTGGGTTGGTGTATGGTTTTTGAGATA          2134

TTAATGCCCAGACAAAAAGCTAATACCAGTCACTCGATAATAAAGTATTCGCATTATAGTTTTTTTAAACTGTCTTCT       2213

TTTTACAAAGAGGGGCAGGTAGGGCTTCAGGCGGATTTCTGACCCATCSTGTACCTTGAAACTTGACCTCAGTTTTCAAG     2292

TTTTACTTTTTATTGGATAAAGACAGAACAAATTGAAAAGGGAGGAAAGTCACATTTACTCTTAAGTAAACCAGAGAAAG     2371
```

FIG.6C

```
TTCTGTTGTTCCTTCCTGCCCATGGCTATGGGGTGTCCAGTGGATGGCGGTGGGGAAAAGGAGAATACACTGG        2450

CCATTTATCCTGGACAAGCTCTTCCAGTCTCTGATGCGAGGAGGTTCATGCCCTAGAAAGGCCCAGTTCCATGACCC    2529

CCATCTTTGAGTTATGAGCAAGCTAAAAGAGAAGACACTATTTCTCACCATTTGTGGAAATGGCCTGGGGAACAAAGACT 2608

GAAATGGGCCTTGAGCCCACCTGCTACCTTGCAGAGAACCATCTCGAGCCCCGTAGATCTTTTAGGACCTCCACAGGC   2687

TATTTCCCACCCCCCAGCCAAAAATAGCTCAGAATCTGCCATCCAGGGCTGTATTAATGATTTATGTAAAGGCAGATG   2766

GTTTATTTCTACTTTGTAAAGGGAAAAGTTGAGGTTCTGAAGGATAAATGATTTGCTCATGAGACAAAATCAAGGTT    2845

AGAAGTTACATGGAATTGTAGGACCAGAGCCATATCATTAGATATCTTTTCTGAAGAATATTCMAAAAGAAAGTC      2924

TCCTTGGCCAGATAACTAAGAGGAATGTTCATTGTATATCTTTTTCTTGGAGATTTATATTAACATATTAAGTGCTC    3003

TGAGAAGTCCTGTGTATTATCTCTTGCTGCATAATAAATTATCCCCAAACTTAAAAAAAAAAAAAAAAAACTCGA      3082

G                                                                                3083
```

FIG.6D

SEQUENCE LISTING

<160> NUMBER OF SEQ ID NOS: 44

<210> SEQ ID NO 1
<211> LENGTH: 1953
<212> TYPE: DNA
<213> ORGANISM: Homo sapiens

<400> SEQUENCE: 1
ggcacgagtc ggagccgggc ggaggggagg ggggaaagag gagcgcaggg tgagagtgag    60

-continued

```
ccgcaggctt cggaggcga gggggcgggg ggagcagcgc cgaggycgcc gcctccgcct      120
ccgccgccta ggactagggg gtggggacg gacaagcccc gatgccgggg gagacggaag      180
agccgagacc cccggagcag caggaccagg aaggggaga ggcggccaag gcggctccgg      240
aggagcccca caacggcccc cctgaggcgg tcgcggcggc gcctgcaggg accactagca      300
gccgcgtgct gagggaggt cgggaccgag gccggccgc tgcggccgcc gccgccgcag       360
ctgtgtcccg ccgaggaag gccgagtatc cccgccggcg gaggagcagc cccagcgcca      420
ggcctcccga cgtccccggg cagcagcccc aggccgcgaa gtccccgtct ccagttcagg     480
gcaagaagag tccgcgactc ctatgcatag aaaaagtaac aactgataaa gatcccaagg    540
aagaaaaaga ggaagaagac gattctgccc tccctcagga agtttccatt gctgcatcta    600
gacctagccg gggctggcgt agtagtagga catctgtttc tcgccatcgt gatacagaga    660
acacccgaag ctctcggtcc aagaccggtt cattgcagct catttgcaag tcagaaccaa    720
atacagacca acttgattat gatgttggag aagagcatca gtctccaggt ggcattagtg    780
gtgaagagga agaggaggag gaagaagaga tgttaatcag tgaagaggag ataccattca    840 agatgatcc aagagatgag acctacaaac cccacttaga aagggaaacc ccaaagccac     900
ggagaaaatc agggaaggta aagaagaga aggagaagaa ggaaattaaa gtggaagtag     960
aggtggaggt gaaagaagag gagaatgaaa ttagagagga tgaggaacct ccaaggaaga   1020
gaggaagaag acgaaaagat gacaaaagtc cacgtttacc caaaggaga aaaaagcctc    1080 caatccagta tgtccgttgt gagatggaag gatgtggaac tgtccttgcc catcctcgct   1140
atttgcagca ccacattaaa taccagcatt tgctgaagaa gaaatatgta tgtccccatc   1200
cctcctgtgg acgactcttc aggcttcaga agcaacttct gcgacatgcc aaacatcata   1260
cagatcaaag ggattatatc tgtgaatatt gtgctcgggc cttcaagagt tcccacaatc   1320
tggcagtgca ccgatgatt cacactggcg agaagccatt acaatgtgag atctgtggat    1380
ttacttgtcg acaaaaggca tctcttaatt ggcacatgaa gaaacatgat gcagactcct   1440
tctaccagtt ttcttgcaat atctgtggca aaaaatttga gaagaaggac agcgtagtgg   1500
cacacaaggc aaaaagccac cctgaggtgc tgattgcaga agctctggct gccaatgcag   1560
gcgccctcat caccagcaca gatatcttgg gcactaaccc agagtccctg acgcagcctt   1620
cagatggtca gggtcttcct cttcttcctg agcccttggg aaaactcaacc tctggagagt  1680 gcctactgtt agaagctgaa gggatgtcaa agtcatactg cagtgggacg gaacgggtga   1740
gcctgatggc tgatgggaag atctttgtgg gaagcggcag cagtggaggc actgaagggc   1800
tggttatgaa ctcagatata ctcggtgcta ccacagaggt tctgattgaa gattcagact   1860
ctgccggacc ttagtggaca ggaagacttg gggcatggga cagctcagac tttgtattta   1920
aaagttaaaa aggacaaaaa aaaaaaaaa aaa                                  1953
```

<210> SEQ ID NO 2
<211> LENGTH: 3103
<212> TYPE: DNA
<213> ORGANISM: Homo sapiens

<400> SEQUENCE: 2

```
gcacgagcgg agagccgcgc agggcgcggg ccgcgcgggg tggggcagcc ggagcgcagg      60
cccccgatcc ccggcgggcg cccccggcc cccgcgcgcg cccggcctc cgggagactg      120 gcgcatgcca cggagcgccc ctcgggccgc cgccgctcct gcccgggccc ctgctgctgc     180
```

```
tgctgtcgcc tgcgcctgct gccccaactc ggcgcccgac tcacaaagaa acatcatgtt    240
cgctccttag caggcaaacg acttttctcc tcgcctcctc gccccgcatg ttcaggacca    300
aacgatctgc gctcgtccgg cgtctctgga ggagccgtgc gcccggcggc gaggacgagg    360
aggagggcgc aggggaggt ggaggaggag gcgagctgcg gggagaaggg gcgacggaca    420
gccgagcgca tggggccggt ggcggcggcc cgggcagggc tggatgctgc ctgggcaagg    480
cggtgcgagg tgccaaaggt caccaccatc cccacccgcc agccgcgggc gccggcgcgg    540 ccggggggcgc cgaggcggat ctgaaggcgc tcacgcactc ggtgctcaag aaactgaagg    600
agcggcagct ggagctgctg ctccaggccg tggagtcccg cggcgggacg cgcaccgcgt    660
gcctcctgct gccccggccgc ctggactgca ggctgggccc gggggcgccc gccggcgcgc    720
agcctgcgca gccgccctcg tcctactcgc tcccctcct gctgtgcaaa gtgttcaggt    780
ggccggatct caggcattcc tcggaagtca agaggctgtg ttgctgtgaa tcttacggga    840
agatcaaccc cgagctggtg tgctgcaacc cccatcacct tagccgactc tgcgaactag    900
agtctccccc ccctccttac tccagatacc cgatggattt tctcaaacca actgcagact    960
gtccagatgc tgtgccttcc tccgctgaaa caggggaac gaattatctg ccccctgggg   1020
ggctttcaga ttcccaactt cttctggagc ctggggatcg gtcacactgg tgcgtggtgg   1080
catactggga ggagaagacg agagtgggga ggctctactg tgtccaggag ccctctctgg   1140
atatcttcta tgatctacct caggggaatg gcttttgcct cggacagctc aattcggaca   1200
acaagagtca gctggtgcag aaggtgcgga gcaaaatcgg ctgcggcatc cagctgacgc   1260
gggaggtgga tggtgtgtgg gtgtacaacc gcagcagtta ccccatcttc atcaagtccg   1320
ccacactgga caacccggac tccaggacgc tgttggtaca caaggtgttc cccggtttct   1380
ccatcaaggc tttcgactac gagaaggcgt acagcctgca gcggcccaat gaccacgagt   1440
ttatgcagca gccgtggacg ggctttaccg tgcagatcag ctttgtgaag gctggggtc   1500 agtgctacac ccgccagttc atcagcagct gcccgtgctg gctagaggtc atcttcaaca   1560
gccggtagcc gcgtgcggag gggacagagc gtgagctgag caggccacac ttcaaactac   1620
tttgctgcta atattttcct cctgagtgct tgcttttcat gcaaactctt tggtcgtttt   1680
ttttttgttt gttggttggt tttcttcttc tcgtcctcgt ttgtgttctg ttttgtttcg   1740
ctctttgaga aatagcttat gaaaagaatt gttgggggtt tttttggaag aagggcagg   1800 tatgatcggc aggacaccct gataggaaga ggggaagcag aaatccaagc accaccaaac   1860
acagtgtatg aagggggggcg gtcatcattt cacttgtcag gagtgtgtgt gagtgtgagt   1920
gtgcggctgt gtgtgcacgc gtgtgcagga gcggcagatg gggagacaac gtgctctttg   1980
ttttgtgtct cttatggatg tccccagcag agaggtttgc agtcccaagc ggtgtctctc   2040
ctgccccttg gacacgctca gtggggcaga ggcagtacct gggcaagctg gcggctgggg   2100
tcccagcagc tgccaggagc acggctctgt ccccagcctg gaaagccccc tgccctcct   2160 ctccctcatc aaggacacgg gcctgtccac aggcttctga gcagcgagcc tgctagtggc   2220
cgaaccagaa ccaattattt tcatccttgt cttattccct tcctgccagc cctgccatt   2280 gtagcgtctt tcttttttgg ccatctgctc ctggatctcc ctgagatggg cttcccaagg   2340
gctgccgggg cagccccctc acagtattgc tcacccagtg ccctctcccc tcagcctctc   2400
ccctgcctgc cctggtgaca tcaggttttt cccggactta gaaaccagc tcagcactgc   2460 ctgctcccat cctgtgtgtt aagctctgct attaggccag caagcgggga tgtccctggg   2520
agggacatgc ttagcagtcc ccttccctcc aagaaggatt tggtccgtca taacccaagg   2580
```

```
taccatccta ggctgacacc taactcttct ttcatttctt ctacaactca tacactcgta    2640
tgatacttcg acactgttct tagctcaatg agcatgttta gactttaaca taagctattt    2700
ttctaactac aaaggtttaa atgaacaaga gaagcattct cattggaaat ttagcattgt    2760
agtgctttga gagagaaagg actcctgaaa aaaaacctga gatttattaa agaaaaaaat    2820
gtattttatg ttatatataa atatattatt acttgtaaat ataagacgt tttataagca    2880 tcattattta tgtattgtgc aatgtgtata acaagaaaa ataagaaaa gatgcacttt    2940 gctttaatat aaatgcaaat aacaaatgcc aaattaaaaa agataaacac aagattggtg    3000
ttttttccta tgggtgttat cacctagctg aatgtttttc taaaggagtt tatgttccat    3060
taaacgattt ttaaaatgta cacttgaaaa aaaaaaaaa aaa                       3103

<210> SEQ ID NO 3
<211> LENGTH: 1393
<212> TYPE: DNA
<213> ORGANISM: Homo sapiens

<400> SEQUENCE: 3
ggcacgaggt tgccctggcg gagcagagac aggccctcgg ggtggaggtc tttggtttca      60
taagagcctg agagagattt ttctaagata tgtgtaacac accaacgtac tgtgacctag     120
gaaaggctgc taaggatgtc ttcaacaaag gatatggctt tggcatggtc aagatagacc     180
tgaaaaccaa gtcttgtagt ggagtggaat tttctacttc tggtcatgct tacactgata     240
cagggaaagc atcaggcaac ctagaaacca atataaggt ctgtaactat ggacttacct     300
tcacccagaa atgaacaca gacaatactc tagggacaga aatctcttgg gagaataagt     360
tggctgaagg gttgaaactg actcttgata ccatatttgt accgaacaca ggaaagaaga     420
gtgggaaatt gaaggcctcc tataaacggg attgttttag tgttggcagt aatgttgata     480 tagattttc tggaccaacc atctatggct gggctgtgtt ggccttcgaa gggtggcttg     540
ctggctatca gatgagtttt gacacagcca atccaaact gtcacagaat aatttcgccc     600
tgggttacaa ggctgcggac ttccagctgc acacacatgt gaacgatggc actgaatttg     660
gaggttctat ctaccagaag gtgaatgaga agattgaaac atccataaac cttgcttgga     720
cagctgggag taacaacacc cgttttggca ttgctgctaa gtacatgctg gattgtagaa     780
cttctctctc tgctaaagta aataatgcca gcctgattgg actgggttat actcagaccc     840
ttcgaccagg agtcaaattg actttatcag ctttaatcga tgggaagaac ttcagtgcag     900
gaggtcacaa ggttggcttg ggatttgaac tggaagctta atgtggtttg aggaaagcat     960
cagatttgtc cctggaagtg aagagaaatg aacccactat gttttggcct taaaattctt    1020
ctgtgaaatt tcaaaagtgt gaactttta ttcttccaaa gaattgtaat cctccccaca    1080
ctgaagtcta ggggttgcga atccctcctg agggagacgc ttgaaggcat gcctggaagt    1140
tgtcatgttt gtgccacgtt tcagttcagt tctgaagtgt tattaaatgt gttcctcagc    1200
gacagtgtag cgtcatgtta gaggagacga tctgacccac cagtttgtac atcacgtcct    1260
gcatgtccca caccattttt tcatgacctt gtaatatact ggtctctgtg ctatagtgga    1320
atctttggtt ttgcatcata gtaaaataaa ataaacccat cacatttgga acataaaaaa    1380 aaaaaaaaa aaa                                                        1393

<210> SEQ ID NO 4
<211> LENGTH: 1036
<212> TYPE: DNA
```

```
<213> ORGANISM: Homo sapiens
<220> FEATURE:
<221> NAME/KEY: misc_feature
<222> LOCATION: (1)...(1036)
<223> OTHER INFORMATION: n = A,T,C or G

<400> SEQUENCE: 4
acgagcctag ccctggtgct caacctgctg cagatccaga ggaatgtcac tctcttcccc      60
gaggaggtga tcgccaccat ctttttcctcc gcctggtggg tccctccctg ctgcgggaca    120
gcagctgctg ttgttggcct actgtacccc tgtatcgaca gtcacctcgg agaaccccac    180
aaatttaaga gagaatgggc cagtgtcatg cgctgcatag cagttttttgt tggcattaac   240
cacgccagtg ctaaattgga ttttgccaat aatgtccagc tgtccttgac tttagcagcc    300
ctatctttgg gcctttggtg gacatttgat cgttccagaa gtggccttgg gctggggatc    360
accatagctt ttctagctac gctgatcacg cagtttctcg tgtataatgg tgtctatcag    420
tatacatccc cagatttcct ctatattcgt tcttggctcc cttgtatatt tttctcagga    480
ggcgtcacgg tggggaacat aggacgacag ttagctatgg gtgttcctga aaagccccat    540
agtgattgag tcttcaaaac caccgattct gagagcaagg aagattttgg aagaaaatct    600
gactgtggat tatgacaaag attatctttt ttcttaagta atctatttag atcgggctga    660
ctgtacaaat gactcctgga aaaaactctt cacctagtct agaataggga ggtggagaat    720
gatgacttac cctgaagtct tcccttgact gcccgcactg gcgcctgtct gtgccctgga    780
gcattctgcc caggctacgt gggttcaggc aggtggcagc ttcccaagta ttcgatttca    840
ttcatgtgat taaacaagt tgccatattt caaaaaaaaa aaaaaaaamc tcgagaccaa    900
cccgcagttt tgtgtcagtg cccaaaggag gtaggttgat ggtgcttaac aaacatgaag    960
tatggtgtaa taggaataat atttatccna aagattttta aaataggcc tgtgtttaaa    1020
aaaaaaaaa aaaaaa                                                    1036

<210> SEQ ID NO 5
<211> LENGTH: 1228
<212> TYPE: DNA
<213> ORGANISM: Homo sapiens

<400> SEQUENCE: 5
atgtgtcact ctcgcagctg ccacccgacc atgaccatcc tgcaggcccc gaccccggcc      60
ccctccacca tcccgggacc ccggcggggc tccggtcctg agatcttcac cttcgaccct    120
ctcccggagc ccgcagcggc ccctgccggg cgcccagcg cctctcgcgg gcaccgaaag    180
cgcagccgca gggttctcta ccctcgagtg gtccggcgcc agctgccagt cgaggaaccg    240
aacccagcca aaaggcttct cttttctgctg ctcaccatcg tcttctgcca gatcctgatg    300
gctgaagagg gtgtgccggc gccctgcct ccagaggacg cccctaacgc cgcatccctg    360
gcgcccaccc ctgtgtcccc cgtcctcgag cccttttaatc tgacttcgga gccctcggac    420
tacgctctgg acctcagcac tttcctccag caacacccgg ccgccttcta actgtgactc    480
cccgcactcc ccaaaaagaa tccgaaaaac cacaaagaaa caccaggcgt acctggtgcg    540
cgagagcgta tccccaactg ggacttccga ggcaacttga actcagaaca ctacagcgga    600
gacgccaccc ggtgcttgag gcgggaccga ggcgcacaga gaccgaggcg catagagacc    660
gaggcacagc ccagctgggg ctaggccggg tgggaaggag agcgtcgtta atttatttct    720
tattgctcct aattaatatt tatatgtatt tatgtacgtc ctcctaggtg atggagatgt    780
gtacgtaata tttatttttaa cttatgcaag ggtgtgagat gttccctctg ctgtaaatgc    840
```

```
aggtctcttg gtatttattg agctttgtgg gactggtgga agcaggacac ctggaactgc      900
ggcaaagtag gagaagaaat ggggaggact cgggtggggg aggacgtccc ggctgggatg      960
aagtctggtg gtgggtcgta agtttaggag gtgactgcat cctccagcat ctcaactccg     1020
tctgtctact gtgtgagact tcggcggacc attaggaatg agatccgtga gatccttcca     1080
tcttcttgaa gtcgccttta gggtggctgc gaggtagagg gttgggggtt ggtgggctgt     1140
cacggagcga ctgtcgagat cgcctagtat gttctgtgaa cacaaataaa attgatttac     1200
tgtcaaaaaa aaaaaaaaaa aactcgag                                        1228

<210> SEQ ID NO 6
<211> LENGTH: 3084
<212> TYPE: DNA
<213> ORGANISM: Homo sapiens

<400> SEQUENCE: 6
gaattcggca cgaggmcagg agctcctttw ctgcgtctcc catcatgggg cttagggttg       60
agtcttcagg ttctgggggc aggaaggacg ggcactcagg aggcccctc cccatccaca      120 gcccctcttt gggagggggg aaacttggca acccggagg catgtggatc ttttcctaag      180
caagatgctg agctggaaag atgggggtgt aaggtaatgt cccaaactga aactttgcca      240
ggcactggga gaggctgtga actctttct ggctttagaa tttaggtcta gatcccaaaa      300
ggctaagtac cccctggggg ctaaccagag gcatgcctgg gctgagctga accttctggt      360
gcactggccc ctggctgact gctcttctgc aggaagttgg aggagattcc tgaagttgat      420
tcctcaggct ggatgtccaa gggggttgga gtttctgatg tctttctgtc tccctctctt      480
ttctttctct ccctaccagg tccacttctt tcagagggc ctgcggtgct ctaaaagttc      540
tcctgttaaa gttagagca aattggttat tattttaaaa tcaataaaac ttttaaaagt      600
actaagacaa cttctaagag gggagtggac agagggcctg gtggcagctc acagtttctt      660
ttctgacctt tggtctcacc caccaagtgt cccacctgag tgcccacctt gcccacctga      720
ggtaatgccc tggggctcca ccagtccaga tccacagggc gcarccatgt gggagtggcg      780
gctgattgtt acccagtagt gttgatagca cattattcat aacagccaaa gagaggaagc      840
aacccaaatg tccattagct gataaatgga taatgaaat atggtacgtc cgaagaatgg       900
aatatcattc acccatgaaa aagaacgaag tccagcacca aaacgtgcta acatggat      960 gaacttcgat gactttgtgc acatgaaag aagaagccag ccacaaaagg ccatatattg     1020
tatgaaatga aatgtccaga atgggcaaac ccatagagac acaaaaatct ccgccacctc     1080
cctactctcg gctgtctcct cgcgacgagt acaagccact ggatctgtcc gattccacat     1140
tgtcttacac tgaaacggag gctaccaact ccctcatcac tgctccgggt gaattctcag     1200
acgccagcat gtctccggac gccaccagc cgagccactg tgcagcgtg gcgtactggg     1260 agcaccggac gcgcgtgggc cgcctctatg cggtgtacga ccaggccgtc agcatcttct     1320
acgacctacc tcagggcagc ggcttctgcc tgggccagct caacctggag cagcgcagcg     1380
agtcggtgcg gcgaacgcgc agcaagatcg gcttcggcat cctgctcagc aaggagcccg     1440
acggcgtgtg ggcctacaac cgcggcgagc acccccatctt cgtcaactcc ccgacgctgg     1500
acgcgcccgg cggccgcgcc ctggtcgtgc gcaaggtgcc cccggctac tccatcaagg     1560 tgttcgactt cgagcgctcg ggcctgcagc acgcgcccga gccgacgcc gccgacggcc     1620 cctacgaccc caacagcgtc cgcatcagct tcgccaaggg ctgggggccc tgctactccc     1680
```

-continued

```
ggcagttcat cacctcctgc ccctgctggc tggagatcct cctcaacaac cccagatagt    1740
ggcggccccg gcgggagggg cgggtgggag gccgcggcca ccgccacctg ccggcctcga    1800
gaggggccga tgcccagaga cacagccccc acggacaaaa cccccagat  atcatctacc    1860 tagatttaat ataaagtttt atatattata tggaaatata tattatactt gtaattatgg    1920 agtcatttt  acaatgtaat tatttatgta tggtgcaatg tgtgtatatg acaaaacaa     1980 gaaagacgca ctttggctta taattctttc aatacagata tattttcttt ctcttcctcc    2040
ttcctcttcc ttacttttta tatatatata taaagaaaat gatacagcag agctaggtgg    2100
aaaagcctgg gtttggtgta tggttttga  gatattaatg cccagacaaa aagctaatac    2160
cagtcactcg ataataaagt attcgcatta  tagttttttt taaactgtct tcttttaca    2220 aagagggcaa ggtagggctt cagcggattt ctgacccatc atgtaccttg aaacttgacc    2280
tcagttttca agtttactt  ttattggata agacagaac  aaattgaaaa gggaggaaag    2340
tcacatttac tcttaagtaa accagagaaa gttctgttgt tccttcctgc ccatggctat    2400
ggggtgtcca gtggataggg atggcggtgg ggaaaggag  aatacactgg ccatttatcc    2460
tggacaagct cttccagtct gatggaggag gttcatgccc tagcctagaa aggcccaggt    2520
ccatgacccc catctttgag ttatgagcaa gctaaaagaa gacactattt ctcaccattt    2580
tgtggaaatg gcctggggaa caaagactga aatgggcctt gagcccacct gctaccttgc    2640
agagaaccat ctcgagcccc gtagatcttt ttaggacctc cacaggstat ttcccacccc    2700
ccagccaaaa atagctcaga atctgcccat ccagggcttg tattaatgat ttatgtaaag    2760
gcagatggtt tatttctact ttgtaaaagg gaaaagttga ggttctgaa  ggataaatga    2820 tttgctcatg agacaaaatc aaggttagaa gttacatgga attgtaggac cagagccata    2880
tcattagatc agctttctga agaatattct ccamaaaaga aagtctcctt ggccagataa    2940
ctaagaggaa tgtttcattg tatatctttt ttcttggaga tttatattaa catattaagt    3000
gctctgagaa gtcctgtgta ttatctcttg ctgcataata aattatcccc amacttaaaa    3060
aaaaaaaaaa aaaaaaaact cgag                                          3084
```

<210> SEQ ID NO 7
<211> LENGTH: 570
<212> TYPE: PRT
<213> ORGANISM: Homo sapiens

<400> SEQUENCE: 7

```
Met Pro Gly Glu Thr Glu Glu Pro Arg Pro Glu Gln Gln Asp Gln
 1               5                  10                  15

Glu Gly Gly Glu Ala Ala Lys Ala Ala Pro Glu Pro Gln Gln Arg
                20                  25                  30

Pro Pro Glu Ala Val Ala Ala Pro Ala Gly Thr Thr Ser Ser Arg
                35                  40                  45

Val Leu Arg Gly Gly Arg Asp Arg Gly Arg Ala Ala Ala Ala Ala
            50                  55                  60

Ala Ala Ala Val Ser Arg Arg Lys Ala Glu Tyr Pro Arg Arg Arg
65                  70                  75                  80

Arg Ser Ser Pro Ser Ala Arg Pro Pro Asp Val Pro Gly Gln Gln Pro
                85                  90                  95

Gln Ala Ala Lys Ser Pro Ser Pro Val Gln Gly Lys Lys Ser Pro Arg
                100                 105                 110

Leu Leu Cys Ile Glu Lys Val Thr Thr Asp Lys Asp Pro Lys Glu Glu
            115                 120                 125
```

```
Lys Glu Glu Asp Asp Ser Ala Leu Pro Gln Glu Val Ser Ile Ala
    130                 135                 140

Ala Ser Arg Pro Ser Arg Gly Trp Arg Ser Ser Arg Thr Ser Val Ser
145                 150                 155                 160

Arg His Arg Asp Thr Glu Asn Thr Arg Ser Ser Arg Ser Lys Thr Gly
                    165                 170                 175

Ser Leu Gln Leu Ile Cys Lys Ser Glu Pro Asn Thr Asp Gln Leu Asp
                180                 185                 190

Tyr Asp Val Gly Glu Glu His Gln Ser Pro Gly Gly Ile Ser Gly Glu
            195                 200                 205

Glu Glu Glu Glu Glu Glu Glu Met Leu Ile Ser Glu Glu Glu Ile
        210                 215                 220

Pro Phe Lys Asp Asp Pro Arg Asp Glu Thr Tyr Lys Pro His Leu Glu
225                 230                 235                 240

Arg Glu Thr Pro Lys Pro Arg Arg Lys Ser Gly Lys Val Lys Glu Glu
                245                 250                 255

Lys Glu Lys Lys Glu Ile Lys Val Glu Val Glu Val Glu Val Lys Glu
            260                 265                 270

Glu Glu Asn Glu Ile Arg Glu Asp Glu Glu Pro Pro Arg Lys Arg Gly
        275                 280                 285

Arg Arg Arg Lys Asp Asp Lys Ser Pro Arg Leu Pro Lys Arg Arg Lys
290                 295                 300

Lys Pro Pro Ile Gln Tyr Val Arg Cys Glu Met Glu Gly Cys Gly Thr
305                 310                 315                 320

Val Leu Ala His Pro Arg Tyr Leu Gln His His Ile Lys Tyr Gln His
                325                 330                 335

Leu Leu Lys Lys Lys Tyr Val Cys Pro His Pro Ser Cys Gly Arg Leu
            340                 345                 350

Phe Arg Leu Gln Lys Gln Leu Leu Arg His Ala Lys His His Thr Asp
        355                 360                 365

Gln Arg Asp Tyr Ile Cys Glu Tyr Cys Ala Arg Ala Phe Lys Ser Ser
    370                 375                 380

His Asn Leu Ala Val His Arg Met Ile His Thr Gly Glu Lys Pro Leu
385                 390                 395                 400

Gln Cys Glu Ile Cys Gly Phe Thr Cys Arg Gln Lys Ala Ser Leu Asn
                405                 410                 415

Trp His Met Lys Lys His Asp Ala Asp Ser Phe Tyr Gln Phe Ser Cys
            420                 425                 430

Asn Ile Cys Gly Lys Lys Phe Glu Lys Lys Asp Ser Val Val Ala His
        435                 440                 445

Lys Ala Lys Ser His Pro Glu Val Leu Ile Ala Glu Ala Leu Ala Ala
    450                 455                 460

Asn Ala Gly Ala Leu Ile Thr Ser Thr Asp Ile Leu Gly Thr Asn Pro
465                 470                 475                 480

Glu Ser Leu Thr Gln Pro Ser Asp Gly Gln Gly Leu Pro Leu Leu Pro
                485                 490                 495

Glu Pro Leu Gly Asn Ser Thr Ser Gly Glu Cys Leu Leu Leu Glu Ala
            500                 505                 510

Glu Gly Met Ser Lys Ser Tyr Cys Ser Gly Thr Glu Arg Val Ser Leu
        515                 520                 525

Met Ala Asp Gly Lys Ile Phe Val Gly Ser Gly Ser Ser Gly Gly Thr
530                 535                 540
```

```
Glu Gly Leu Val Met Asn Ser Asp Ile Leu Gly Ala Thr Thr Glu Val
545                 550                 555                 560

Leu Ile Glu Asp Ser Asp Ser Ala Gly Pro
            565                 570
```

<210> SEQ ID NO 8
<211> LENGTH: 426
<212> TYPE: PRT
<213> ORGANISM: Homo sapiens

<400> SEQUENCE: 8

```
Met Phe Arg Thr Lys Arg Ser Ala Leu Val Arg Arg Leu Trp Arg Ser
 1               5                  10                  15

Arg Ala Pro Gly Gly Glu Asp Glu Glu Gly Ala Gly Gly Gly
            20                  25                  30

Gly Gly Gly Glu Leu Arg Gly Glu Gly Ala Thr Asp Ser Arg Ala His
            35                  40                  45

Gly Ala Gly Gly Gly Pro Gly Arg Ala Gly Cys Cys Leu Gly Lys
        50                  55                  60

Ala Val Arg Gly Ala Lys Gly His His His Pro His Pro Pro Ala Ala
65                  70                  75                  80

Gly Ala Gly Ala Ala Gly Gly Ala Glu Ala Asp Leu Lys Ala Leu Thr
                85                  90                  95

His Ser Val Leu Lys Lys Leu Lys Glu Arg Gln Leu Glu Leu Leu Leu
                100                 105                 110

Gln Ala Val Glu Ser Arg Gly Gly Thr Arg Thr Ala Cys Leu Leu Leu
                115                 120                 125

Pro Gly Arg Leu Asp Cys Arg Leu Gly Pro Gly Ala Pro Ala Gly Ala
            130                 135                 140

Gln Pro Ala Gln Pro Pro Ser Ser Tyr Ser Leu Pro Leu Leu Leu Cys
145                 150                 155                 160

Lys Val Phe Arg Trp Pro Asp Leu Arg His Ser Ser Glu Val Lys Arg
                165                 170                 175

Leu Cys Cys Cys Glu Ser Tyr Gly Lys Ile Asn Pro Glu Leu Val Cys
                180                 185                 190

Cys Asn Pro His His Leu Ser Arg Leu Cys Glu Leu Glu Ser Pro Pro
            195                 200                 205

Pro Pro Tyr Ser Arg Tyr Pro Met Asp Phe Leu Lys Pro Thr Ala Asp
        210                 215                 220

Cys Pro Asp Ala Val Pro Ser Ser Ala Glu Thr Gly Gly Thr Asn Tyr
225                 230                 235                 240

Leu Ala Pro Gly Gly Leu Ser Asp Ser Gln Leu Leu Leu Glu Pro Gly
                245                 250                 255

Asp Arg Ser His Trp Cys Val Val Ala Tyr Trp Glu Glu Lys Thr Arg
            260                 265                 270

Val Gly Arg Leu Tyr Cys Val Gln Glu Pro Ser Leu Asp Ile Phe Tyr
        275                 280                 285

Asp Leu Pro Gln Gly Asn Gly Phe Cys Leu Gly Gln Leu Asn Ser Asp
    290                 295                 300

Asn Lys Ser Gln Leu Val Gln Lys Val Arg Ser Lys Ile Gly Cys Gly
305                 310                 315                 320

Ile Gln Leu Thr Arg Glu Val Asp Gly Val Trp Val Tyr Asn Arg Ser
                325                 330                 335

Ser Tyr Pro Ile Phe Ile Lys Ser Ala Thr Leu Asp Asn Pro Asp Ser
            340                 345                 350
```

```
Arg Thr Leu Leu Val His Lys Val Phe Pro Gly Phe Ser Ile Lys Ala
            355                 360                 365

Phe Asp Tyr Glu Lys Ala Tyr Ser Leu Gln Arg Pro Asn Asp His Glu
    370                 375                 380

Phe Met Gln Gln Pro Trp Thr Gly Phe Thr Val Gln Ile Ser Phe Val
385                 390                 395                 400

Lys Gly Trp Gly Gln Cys Tyr Thr Arg Gln Phe Ile Ser Ser Cys Pro
                405                 410                 415

Cys Trp Leu Glu Val Ile Phe Asn Ser Arg
            420                 425

<210> SEQ ID NO 9
<211> LENGTH: 283
<212> TYPE: PRT
<213> ORGANISM: Homo sapiens

<400> SEQUENCE: 9

Met Cys Asn Thr Pro Thr Tyr Cys Asp Leu Gly Lys Ala Ala Lys Asp
  1               5                  10                  15

Val Phe Asn Lys Gly Tyr Gly Phe Gly Met Val Lys Ile Asp Leu Lys
             20                  25                  30

Thr Lys Ser Cys Ser Gly Val Glu Phe Ser Thr Ser Gly His Ala Tyr
         35                  40                  45

Thr Asp Thr Gly Lys Ala Ser Gly Asn Leu Glu Thr Lys Tyr Lys Val
     50                  55                  60

Cys Asn Tyr Gly Leu Thr Phe Thr Gln Lys Trp Asn Thr Asp Asn Thr
 65                  70                  75                  80

Leu Gly Thr Glu Ile Ser Trp Glu Asn Lys Leu Ala Glu Gly Leu Lys
                 85                  90                  95

Leu Thr Leu Asp Thr Ile Phe Val Pro Asn Thr Gly Lys Lys Ser Gly
            100                 105                 110

Lys Leu Lys Ala Ser Tyr Lys Arg Asp Cys Phe Ser Val Gly Ser Asn
        115                 120                 125

Val Asp Ile Asp Phe Ser Gly Pro Thr Ile Tyr Gly Trp Ala Val Leu
    130                 135                 140

Ala Phe Glu Gly Trp Leu Ala Gly Tyr Gln Met Ser Phe Asp Thr Ala
145                 150                 155                 160

Lys Ser Lys Leu Ser Gln Asn Asn Phe Ala Leu Gly Tyr Lys Ala Ala
                165                 170                 175

Asp Phe Gln Leu His Thr His Val Asn Asp Gly Thr Glu Phe Gly Gly
            180                 185                 190

Ser Ile Tyr Gln Lys Val Asn Glu Lys Ile Glu Thr Ser Ile Asn Leu
        195                 200                 205

Ala Trp Thr Ala Gly Ser Asn Asn Thr Arg Phe Gly Ile Ala Ala Lys
    210                 215                 220

Tyr Met Leu Asp Cys Arg Thr Ser Leu Ser Ala Lys Val Asn Asn Ala
225                 230                 235                 240

Ser Leu Ile Gly Leu Gly Tyr Thr Gln Thr Leu Arg Pro Gly Val Lys
                245                 250                 255

Leu Thr Leu Ser Ala Leu Ile Asp Gly Lys Asn Phe Ser Ala Gly Gly
            260                 265                 270

His Lys Val Gly Leu Gly Phe Glu Leu Glu Ala
        275                 280
```

-continued

```
<210> SEQ ID NO 10
<211> LENGTH: 181
<212> TYPE: PRT
<213> ORGANISM: Homo sapiens

<400> SEQUENCE: 10

Thr Ser Leu Ala Leu Val Leu Asn Leu Leu Gln Ile Gln Arg Asn Val
 1               5                  10                  15

Thr Leu Phe Pro Glu Val Ile Ala Thr Ile Phe Ser Ser Ala Trp
             20                  25                  30

Trp Val Pro Pro Cys Cys Gly Thr Ala Ala Val Val Gly Leu Leu
             35                  40                  45

Tyr Pro Cys Ile Asp Ser His Leu Gly Glu Pro His Lys Phe Lys Arg
 50                  55                  60

Glu Trp Ala Ser Val Met Arg Cys Ile Ala Val Phe Val Gly Ile Asn
65                  70                  75                  80

His Ala Ser Ala Lys Leu Asp Phe Ala Asn Asn Val Gln Leu Ser Leu
                 85                  90                  95

Thr Leu Ala Ala Leu Ser Leu Gly Leu Trp Trp Thr Phe Asp Arg Ser
            100                 105                 110

Arg Ser Gly Leu Gly Leu Gly Ile Thr Ile Ala Phe Leu Ala Thr Leu
            115                 120                 125

Ile Thr Gln Phe Leu Val Tyr Asn Gly Val Tyr Gln Tyr Thr Ser Pro
130                 135                 140

Asp Phe Leu Tyr Ile Arg Ser Trp Leu Pro Cys Ile Phe Phe Ser Gly
145                 150                 155                 160

Gly Val Thr Val Gly Asn Ile Gly Arg Gln Leu Ala Met Gly Val Pro
                165                 170                 175

Glu Lys Pro His Ser
            180

<210> SEQ ID NO 11
<211> LENGTH: 156
<212> TYPE: PRT
<213> ORGANISM: Homo sapiens

<400> SEQUENCE: 11

Met Cys His Ser Arg Ser Cys Pro Thr Met Thr Ile Leu Gln Ala
 1               5                  10                  15

Pro Thr Pro Ala Pro Ser Thr Ile Pro Gly Pro Arg Arg Gly Ser Gly
             20                  25                  30

Pro Glu Ile Phe Thr Phe Asp Pro Leu Pro Glu Pro Ala Ala Ala Pro
             35                  40                  45

Ala Gly Arg Pro Ser Ala Ser Arg Gly His Arg Lys Arg Ser Arg Arg
 50                  55                  60

Val Leu Tyr Pro Arg Val Val Arg Arg Gln Leu Pro Val Glu Glu Pro
65                  70                  75                  80

Asn Pro Ala Lys Arg Leu Leu Phe Leu Leu Leu Thr Ile Val Phe Cys
                 85                  90                  95

Gln Ile Leu Met Ala Glu Glu Gly Val Pro Ala Pro Leu Pro Pro Glu
            100                 105                 110

Asp Ala Pro Asn Ala Ala Ser Leu Ala Pro Thr Pro Val Ser Pro Val
            115                 120                 125

Leu Glu Pro Phe Asn Leu Thr Ser Glu Pro Ser Asp Tyr Ala Leu Asp
130                 135                 140

Leu Ser Thr Phe Leu Gln Gln His Pro Ala Ala Phe
```

```
145                 150                 155

<210> SEQ ID NO 12
<211> LENGTH: 235
<212> TYPE: PRT
<213> ORGANISM: Homo sapiens

<400> SEQUENCE: 12

Met Ser Arg Met Gly Lys Pro Ile Glu Thr Gln Lys Ser Pro Pro Pro
 1               5                  10                  15

Pro Tyr Ser Arg Leu Ser Pro Arg Asp Glu Tyr Lys Pro Leu Asp Leu
            20                  25                  30

Ser Asp Ser Thr Leu Ser Tyr Thr Glu Thr Ala Thr Asn Ser Leu
        35                  40                  45

Ile Thr Ala Pro Gly Glu Phe Ser Asp Ala Ser Met Ser Pro Asp Ala
 50                  55                  60

Thr Lys Pro Ser His Trp Cys Ser Val Ala Tyr Trp Glu His Arg Thr
 65                  70                  75                  80

Arg Val Gly Arg Leu Tyr Ala Val Tyr Asp Gln Ala Val Ser Ile Phe
            85                  90                  95

Tyr Asp Leu Pro Gln Gly Ser Gly Phe Cys Leu Gly Gln Leu Asn Leu
            100                 105                 110

Glu Gln Arg Ser Glu Ser Val Arg Arg Thr Arg Ser Lys Ile Gly Phe
        115                 120                 125

Gly Ile Leu Leu Ser Lys Glu Pro Asp Gly Val Trp Ala Tyr Asn Arg
130                 135                 140

Gly Glu His Pro Ile Phe Val Asn Ser Pro Thr Leu Asp Ala Pro Gly
145                 150                 155                 160

Gly Arg Ala Leu Val Val Arg Lys Val Pro Pro Gly Tyr Ser Ile Lys
                165                 170                 175

Val Phe Asp Phe Glu Arg Ser Gly Leu Gln His Ala Pro Glu Pro Asp
            180                 185                 190

Ala Ala Asp Gly Pro Tyr Asp Pro Asn Ser Val Arg Ile Ser Phe Ala
        195                 200                 205

Lys Gly Trp Gly Pro Cys Tyr Ser Arg Gln Phe Ile Thr Ser Cys Pro
    210                 215                 220

Cys Trp Leu Glu Ile Leu Leu Asn Asn Pro Arg
225                 230                 235

<210> SEQ ID NO 13
<211> LENGTH: 12
<212> TYPE: DNA
<213> ORGANISM: Artificial Sequence
<220> FEATURE:
<223> OTHER INFORMATION: Primer

<400> SEQUENCE: 13 ttttttttttt tc                                                              12

<210> SEQ ID NO 14
<211> LENGTH: 10
<212> TYPE: DNA
<213> ORGANISM: Artificial Sequence
<220> FEATURE:
<223> OTHER INFORMATION: Primer

<400> SEQUENCE: 14
gtgaggcgtc                                                                  10
```

<210> SEQ ID NO 15
<211> LENGTH: 10
<212> TYPE: DNA
<213> ORGANISM: Artificial Sequence
<220> FEATURE:
<223> OTHER INFORMATION: Primer

<400> SEQUENCE: 15
tggaccggtg                                                          10

<210> SEQ ID NO 16
<211> LENGTH: 12
<212> TYPE: DNA
<213> ORGANISM: Artificial Sequence
<220> FEATURE:
<223> OTHER INFORMATION: Primer

<400> SEQUENCE: 16
tttttttttt ta                                                       12

<210> SEQ ID NO 17
<211> LENGTH: 10
<212> TYPE: DNA
<213> ORGANISM: Artificial Sequence
<220> FEATURE:
<223> OTHER INFORMATION: Primer

<400> SEQUENCE: 17
agacgtccac                                                          10

<210> SEQ ID NO 18
<211> LENGTH: 10
<212> TYPE: DNA
<213> ORGANISM: Artificial Sequence
<220> FEATURE:
<223> OTHER INFORMATION: Primer

<400> SEQUENCE: 18
acttcgccac                                                          10

<210> SEQ ID NO 19
<211> LENGTH: 10
<212> TYPE: DNA
<213> ORGANISM: Artificial Sequence
<220> FEATURE:
<223> OTHER INFORMATION: Primer

<400> SEQUENCE: 19
tcggacgtga                                                          10

<210> SEQ ID NO 20
<211> LENGTH: 17
<212> TYPE: DNA
<213> ORGANISM: Artificial Sequence
<220> FEATURE:
<223> OTHER INFORMATION: Antisense molecule

<400> SEQUENCE: 20
catttcattt catacaa                                                  17

<210> SEQ ID NO 21
<211> LENGTH: 23
<212> TYPE: DNA
<213> ORGANISM: Artificial Sequence
<220> FEATURE:
<223> OTHER INFORMATION: Antisense molecule

```
<400> SEQUENCE: 21
catttcattt catacaatat atg                                          23

<210> SEQ ID NO 22
<211> LENGTH: 29
<212> TYPE: DNA
<213> ORGANISM: Artificial Sequence
<220> FEATURE:
<223> OTHER INFORMATION: Antisense molecule

<400> SEQUENCE: 22
catttcattt catacaatat atggccttt                                    29

<210> SEQ ID NO 23
<211> LENGTH: 35
<212> TYPE: DNA
<213> ORGANISM: Artificial Sequence
<220> FEATURE:
<223> OTHER INFORMATION: Antisense molecule

<400> SEQUENCE: 23
catttcattt catacaatat atggcctttt gtggc                             35

<210> SEQ ID NO 24
<211> LENGTH: 35
<212> TYPE: DNA
<213> ORGANISM: Artificial Sequence
<220> FEATURE:
<223> OTHER INFORMATION: Antisense molecule

<400> SEQUENCE: 24
ggacatttca tttcatacaa tatatggcct tttgt                             35

<210> SEQ ID NO 25
<211> LENGTH: 29
<212> TYPE: DNA
<213> ORGANISM: Artificial Sequence
<220> FEATURE:
<223> OTHER INFORMATION: Antisense molecule

<400> SEQUENCE: 25
ttcatttcat acaatatatg gccttttgt                                    29

<210> SEQ ID NO 26
<211> LENGTH: 23
<212> TYPE: DNA
<213> ORGANISM: Artificial Sequence
<220> FEATURE:
<223> OTHER INFORMATION: Antisense molecule

<400> SEQUENCE: 26
tcatacaata tatggccttt tgt                                          23

<210> SEQ ID NO 27
<211> LENGTH: 17
<212> TYPE: DNA
<213> ORGANISM: Artificial Sequence
<220> FEATURE:
<223> OTHER INFORMATION: Antisense molecule

<400> SEQUENCE: 27
aatatatggc cttttgt                                                 17

<210> SEQ ID NO 28
```

```
<211> LENGTH: 17
<212> TYPE: DNA
<213> ORGANISM: Artificial Sequence
<220> FEATURE:
<223> OTHER INFORMATION: Antisense molecule

<400> SEQUENCE: 28
catgcggggc gaggagg                                                17

<210> SEQ ID NO 29
<211> LENGTH: 23
<212> TYPE: DNA
<213> ORGANISM: Artificial Sequence
<220> FEATURE:
<223> OTHER INFORMATION: Antisense molecule

<400> SEQUENCE: 29
catgcggggc gaggaggcga gga                                         23

<210> SEQ ID NO 30
<211> LENGTH: 29
<212> TYPE: DNA
<213> ORGANISM: Artificial Sequence
<220> FEATURE:
<223> OTHER INFORMATION: Antisense molecule

<400> SEQUENCE: 30
catgcggggc gaggaggcga ggagaaaag                                   29

<210> SEQ ID NO 31
<211> LENGTH: 35
<212> TYPE: DNA
<213> ORGANISM: Artificial Sequence
<220> FEATURE:
<223> OTHER INFORMATION: Antisense molecule

<400> SEQUENCE: 31
catgcggggc gaggaggcga ggagaaaagt cgttt                            35

<210> SEQ ID NO 32
<211> LENGTH: 35
<212> TYPE: DNA
<213> ORGANISM: Artificial Sequence
<220> FEATURE:
<223> OTHER INFORMATION: Antisense molecule

<400> SEQUENCE: 32
gaacatgcgg ggcgaggagg cgaggagaaa agtcg                            35

<210> SEQ ID NO 33
<211> LENGTH: 29
<212> TYPE: DNA
<213> ORGANISM: Artificial Sequence
<220> FEATURE:
<223> OTHER INFORMATION: Antisense molecule

<400> SEQUENCE: 33
gcggggcgag gaggcgagga gaaaagtcg                                   29

<210> SEQ ID NO 34
<211> LENGTH: 23
<212> TYPE: DNA
<213> ORGANISM: Artificial Sequence
<220> FEATURE:
<223> OTHER INFORMATION: Antisense molecule

<400> SEQUENCE: 34
```

```
cgaggaggcg aggagaaaag tcg                                           23

<210> SEQ ID NO 35
<211> LENGTH: 17
<212> TYPE: DNA
<213> ORGANISM: Artificial Sequence
<220> FEATURE:
<223> OTHER INFORMATION: Antisense molecule

<400> SEQUENCE: 35
ggcgaggaga aaagtcg                                                  17

<210> SEQ ID NO 36
<211> LENGTH: 20
<212> TYPE: RNA
<213> ORGANISM: Artificial Sequence
<220> FEATURE:
<223> OTHER INFORMATION: Ribozyme molecule
<220> FEATURE:
<221> NAME/KEY: misc_feature
<222> LOCATION: (1)...(20)
<223> OTHER INFORMATION: n = A,T,C or G

<400> SEQUENCE: 36
caaagcngnn cngagnaguc                                               20

<210> SEQ ID NO 37
<211> LENGTH: 69
<212> TYPE: RNA
<213> ORGANISM: Artificial Sequence
<220> FEATURE:
<223> OTHER INFORMATION: Ribozyme molecule
<220> FEATURE:
<221> NAME/KEY: misc_feature
<222> LOCATION: (1)...(69)
<223> OTHER INFORMATION: n = A,T,C or G

<400> SEQUENCE: 37
gguggagccc cagggcauua ccucaaagcn gnncngagna gucgugggca aggugggcac   60
ucagguggg                                                           69

<210> SEQ ID NO 38
<211> LENGTH: 60
<212> TYPE: RNA
<213> ORGANISM: Artificial Sequence
<220> FEATURE:
<223> OTHER INFORMATION: Ribozyme molecule
<220> FEATURE:
<221> NAME/KEY: misc_feature
<222> LOCATION: (1)...(60)
<223> OTHER INFORMATION: n = A,T,C or G

<400> SEQUENCE: 38
gugucucuau ggguuugccc aaagcngnnc ngagnagucu cuggacauuu cauuucauac   60

<210> SEQ ID NO 39
<211> LENGTH: 76
<212> TYPE: RNA
<213> ORGANISM: Artificial Sequence
<220> FEATURE:
<223> OTHER INFORMATION: Ribozyme molecule
<220> FEATURE:
<221> NAME/KEY: misc_feature
<222> LOCATION: (1)...(76)
<223> OTHER INFORMATION: n = A,T,C or G

<400> SEQUENCE: 39
```

```
ggcccucucg ccgucgggcu ccuugcugag caaagcngnn cngagnaguc gaugccgaag      60
ccgaucuugc ugcgcg                                                     76

<210> SEQ ID NO 40
<211> LENGTH: 68
<212> TYPE: RNA
<213> ORGANISM: Artificial Sequence
<220> FEATURE:
<223> OTHER INFORMATION: Ribozyme molecule
<220> FEATURE:
<221> NAME/KEY: misc_feature
<222> LOCATION: (1)...(68)
<223> OTHER INFORMATION: n = A,T,C or G

<400> SEQUENCE: 40
cguuugccug cuaaggagcg aacaaagcng nncngagnag ucgauguuuc uuugugaguc      60
gggcgccg                                                              68

<210> SEQ ID NO 41
<211> LENGTH: 80
<212> TYPE: RNA
<213> ORGANISM: Artificial Sequence
<220> FEATURE:
<223> OTHER INFORMATION: Ribozyme molecule
<220> FEATURE:
<221> NAME/KEY: misc_feature
<222> LOCATION: (1)...(80)
<223> OTHER INFORMATION: n = A,T,C or G

<400> SEQUENCE: 41
cgccggacga gcgcagaucg uuugguccug aacaaagcng nncngagnag uccggggcga      60
ggaggcgagg agaaaagucg                                                 80

<210> SEQ ID NO 42
<211> LENGTH: 84
<212> TYPE: RNA
<213> ORGANISM: Artificial Sequence
<220> FEATURE:
<223> OTHER INFORMATION: Ribozyme molecule
<220> FEATURE:
<221> NAME/KEY: misc_feature
<222> LOCATION: (1)...(84)
<223> OTHER INFORMATION: n = A,T,C or G

<400> SEQUENCE: 42
ggaguaagga gggggggag acucuaguuc gcaaagcngn ncngagnagu cagucggcua       60
aggugauggg gguugcagca cacc                                            84

<210> SEQ ID NO 43
<211> LENGTH: 16
<212> TYPE: PRT
<213> ORGANISM: Artificial Sequence
<220> FEATURE:
<223> OTHER INFORMATION: Peptide antigen

<400> SEQUENCE: 43

Tyr Thr Asp Thr Gly Lys Ala Ser Gly Asn Leu Glu Thr Lys Tyr Lys
 1               5                  10                  15

<210> SEQ ID NO 44
<211> LENGTH: 15
<212> TYPE: PRT
<213> ORGANISM: Artificial Sequence
<220> FEATURE:
<223> OTHER INFORMATION: Peptide antigen
```

-continued

```
<400> SEQUENCE: 44

Thr Gly Lys Lys Ser Gly Lys Leu Lys Ala Ser Tyr Lys Arg Asp
1               5                   10                  15
```

COMPOSITIONS AND METHODS FOR THE TREATMENT AND DIAGNOSIS OF CARDIOVASCULAR DISEASE

This application is a continuation-in-part of application Ser. No. 08/870,434 filed Jun. 6, 1997, which is a continuation-in-part of application Ser. No. 08/799,910, filed Feb. 13, 1997, which claims the benefit under 35 U.S.C. §119(e) of co-pending provisional Application No. 60/011,787 filed Feb. 16, 1996, each of which is incorporated herein by reference in its entirty.

1. INTRODUCTION

The present invention relates to methods and compositions for the treatment and diagnosis of cardiovascular disease, including, but not limited to, atherosclerosis, ischemia/reperfusion, hypertension, restenosis, and arterial inflammation. The present invention further relates to methods and compositions for the treatment and diagnosis of fibroproliferative and oncogenic disorders, especially TGF-β-related disorders, including diabetic retinopathy, artherosclerosis, angiogenesis, inflammation, fibrosis, tumor growth and vascularization. The present invention still further relates to screening methods to identify compositions for such therapeutic and diagnostic uses. Genes which are differentially expressed in cardiovascular or oncogenic disease states, relative to their expression in normal, or non-disease states are identified. Genes are also identified via the ability of their gene products to interact with other gene products involved in cardiovascular or oncogenic disease. The genes identified may be used diagnostically or as targets for therapeutic intervention. Additionally, methods are provided for the diagnostic monitoring of patients undergoing clinical evaluation for the treatment of cardiovascular, fibroproliferative or oncogenic related disorders, for monitoring the efficacy of compounds in clinical trials, and for identifying subjects who may be predisposed to such disorders.

2. BACKGROUND OF THE INVENTION

Cardiovascular disease is a major health risk throughout the industrialized world. Atherosclerosis, the most prevalent of cardiovascular diseases, is the principal cause of heart attack, stroke, and gangrene of the extremities, and thereby the principal cause of death in the United States. theroscle-rosis is a complex disease involving many cell types and molecular factors (for a detailed review, see Ross, 1993, Nature 362: 801–809). The process, in normal circumstances a protective response to insults to the endothelium and smooth muscle cells (SMCs) of the wall of the artery, consists of the formation of fibrofatty and fibrous lesions or plaques, preceded and accompanied by inflammation. The advanced lesions of atherosclerosis may occlude the artery concerned, and result from an excessive inflammatory-fibroproliferative response to numerous different forms of insult. For example, shear stresses are thought to be responsible for the frequent occurrence of atherosclerotic plaques in regions of the circulatory system where turbulent blood flow occurs, such as branch points and irregular structures.

The first observable event in the formation of an atherosclerotic plaque occurs when blood-borne monocytes adhere to the vascular endothelial layer and transmigrate through to the sub-endothelial space. Adjacent endothelial cells at the same time produce oxidized low density lipoprotein (LDL). These oxidized LDL's are then taken up in large amounts by the monocytes through scavenger receptors expressed on their surfaces. In contrast to the regulated pathway by which native LDL (nLDL) is taken up by nLDL specific receptors, the scavenger pathway of uptake is not regulated by the monocytes.

These lipid-filled monocytes are called foam cells, and are the major constituent of the fatty streak. Interactions between foam cells and the endothelial and SMCs which surround them lead to a state of chronic local inflammation which can eventually lead to smooth muscle cell proliferation and migration, and the formation of a fibrous plaque. Such plaques occlude the blood vessel concerned and thus restrict the flow of blood, resulting in ischemia.

Ischemia is a condition characterized by a lack of oxygen supply in tissues of organs due to inadequate perfusion. Such inadequate perfusion can have number of natural causes, including atherosclerotic or restenotic lesions, anemia, or stroke, to name a few. Many medical interventions, such as the interruption of the flow of blood during bypass surgery, for example, also lead to ischemia. In addition to sometimes being caused by diseased cardiovascular tissue, ischemia may sometimes affect cardiovascular tissue, such as in ischemic heart disease. Ischemia may occur in any organ, however, that is suffering a lack of oxygen supply.

The most common cause of ischemia in the heart is atherosclerotic disease of epicardial coronary arteries. By reducing the lumen of these vessels, atherosclerosis causes an absolute decrease in myocardial perfusion in the basal state or limits appropriate increases in perfusion when the demand for flow is augmented. Coronary blood flow can also be limited by arterial thrombi, spasm, and, rarely, coronary emboli, as well as by ostial narrowing due to luetic aortitis. Congenital abnormalities, such as anomalous origin of the left anterior descending coronary artery from the pulmonary artery, may cause myocardial ischemia and infarction in infancy, but this cause is very rare in adults. Myocardial ischemia can also occur if myocardial oxygen demands are abnormally increased, as in severe ventricular hypertrophy due to hypertension or aortic stenosis. The latter can be present with angina that is indistinguishable from that caused by coronary atherosclerosis. A reduction in the oxygen-carrying capacity of the blood, as in extremely severe anemia or in the presence of carboxy-hemoglobin, is a rare cause of myocardial ischemia. Not infrequently, two or more causes of ischemia will coexist, such as an increase in oxygen demand due to left ventricular hypertrophy and a reduction in oxygen supply secondary to coronary atherosclerosis.

The principal surgical approaches to the treatment of ischemic atherosclerosis are bypass grafting, endarterectomy, and percutaneous translumenal angioplasty (PCTA). The failure rate after these approaches due to restenosis, in which the occlusions recur and often become even worse, is extraordinarily high (30–50%). It appears that much of the restenosis is due to further inflammation, smooth muscle accumulation, and thrombosis.

A modified balloon angioplasty approach was used to treat arterial restenosis in pigs by gene therapy (Ohno et al., 1994, Science 265: 781–784). A specialized catheter was used to introduce a recombinant adenovirus carrying the gene encoding thymidine kinase (tk) into the cells at the site of arterial blockage. Subsequently, the pigs were treated with ganciclovir, a nucleoside analog which is converted by tk into a toxic form which kills cells when incorporated into DNA. Treated animals had a 50% to 90% reduction in arterial wall thickening without any observed local or systemic toxicities.

Because of the presumed role of the excessive inflammatory-fibroproliferative response in atherosclerosis and ischemia, a number of researchers have investigated, in the context of arterial injury, the expression of certain factors involved in inflammation, cell recruitment and proliferation. These factors include growth factors, cytokines, and other chemicals, including lipids involved in cell recruitment and migration, cell proliferation and the control of lipid and protein synthesis.

For example, the expression of PDGF (platelet derived growth factor) or its receptor was studied: in rats during repair of arterial injury (Majesky et al., 1990, J. Cell Biol. 111: 2149); in adherent cultures of human monocyte-derived macrophages treated with oxidized LDL (Malden et al., 1991, J. Biol. Chem. 266: 13901); and in bovine aortic endothelial cells subjected to fluid shear stress (Resnick et al., 1993, Proc. Natl. Acad. Sci. USA 90: 4591–4595). Expression of IGF-I (insulin-like growth factor-I) was studied after balloon deendothelialization of rat aorta (Cercek et al., 1990, Circulation Research 66: 1755–1760).

Other studies have focused on the expression of adhesion-molecules on the surface of activated endothelial cells which mediate monocyte adhesion. These adhesion molecules include intracellular adhesion molecule-1, ICAM-1 (Simmons et al., 1988, Nature, 331: 624–627), ELAM (Bevilacqua et al., 1989, Science 243: 1160–1165; Bevilacqua et al., 1991, Cell 67: 233), and vascular cell adhesion molecule, VCAM-1 (Osborn et al., 1989, Cell 59: 1203–1211); all of these surface molecules are induced transcriptionally in the presence of IL-1. Histological studies reveal that ICAM-1, ELAM and VCAM-1 are expressed on endothelial cells in areas of lesion formation in vivo (Cybulsky et al., 1991, Science 251: 788–791; 1991, Arterioscler. Thromb. 11: 1397a; Poston et al., 1992, Am. J. Pathol. 140: 665–673). VCAM-1 and ICAM-1 were shown to be induced in cultured rabbit arterial endothelium, as well as in cultured human iliac artery endothelial cells by lysophophatidylcholine, a major phospholipid component of atherogenic lipoproteins. (Kume et al., 1992, J. Clin. Invest. 90: 1138–1144). VCAM-I, ICAM-1, and class II major histocompatibility antigens were reported to be induced in response to injury to rabbit aorta (Tanaka, et al., 1993, Circulation 88: 1788–1803).

Cytomegalovirus (CMV) has been implicated in restenosis as well as atherosclerosis in general (Speir, et al., 1994, Science 265: 391–394). It was observed that the CMV protein IE84 apparently predisposes smooth muscle cells to increased growth at the site of restenosis by combining with and inactivating p53 protein, which is known to suppress tumors in its active form.

The foregoing studies are aimed at defining the role of particular gene products presumed to be involved in the excessive inflammatory-fibroproliferative response leading to atherosclerotic plaque formation. However, such approaches cannot identify the full panoply of gene products that are involved in the disease process, much less identify those which may serve as therapeutic targets for the diagnosis and treatment of various forms of cardiovascular disease.

3. SUMMARY OF THE INVENTION

The present invention relates to methods and compositions for the treatment and diagnosis of cardiovascular disease, including but not limited to, atherosclerosis, ischemia/reperfusion, hypertension, restenosis, and arterial inflammation. Specifically, genes are identified and described which are differentially expressed in cardiovascular disease states, relative to their expression in normal, or non-cardiovascular disease states. The present invention further relates to screening methods to identify compositions which can be utilized as part of such diagnostic therapeutic uses.

The present invention further relates to methods and compositions for the treatment and diagnosis of fibroproliferative and oncogenic disorders, especially TGF-β-related disorders, including diabetic retinopathy, artherosclerosis, angiogenesis, inflammation, fibrosis, tumor growth and vascularization. Specifically, genes are identified and described which are differentially expressed in oncogenic disease states, relative to their expression in normal, or non-oncogenic disease states. The present invention still further relates to screening methods to identify compositions involved in activation or enhancement of the TGF-β signaling pathway and their diagnostic and therapeutic uses for such disorders.

The term "activation" as used herein shall represent any alteration of a signaling pathway or biological response including, for example, increases above basal levels, restoration to basal levels from an inhibited state, and stimulation of the pathway above basal levels.

"Differential expression", as used herein, refers to both quantitative as well as qualitative differences in the genes' temporal and/or tissue expression patterns. Differentially expressed genes may represent "fingerprint genes," and/or "target genes." "Fingerprint gene," as used herein, refers to a differentially expressed gene whose expression pattern may be utilized as part of a prognostic or diagnostic cardiovascular disease evaluation, or which, alternatively, may be used in methods for identifying compounds useful for the treatment of cardiovascular disease. "Target gene", as used herein, refers to a differentially expressed gene involved in cardiovascular disease such that modulation of the level of target gene expression or of target gene product activity may act to ameliorate a cardiovascular disease condition. Compounds that modulate target gene expression or activity of the target gene product can be used in the treatment of cardiovascular disease.

Further, "pathway genes" are defined via the ability of their products to interact with other gene products involved in cardiovascular disease. Pathway genes may also exhibit target gene and/or fingerprint gene characteristics. Although the genes described herein may be differentially expressed with respect to cardiovascular disease, and/or their products may interact with gene products important to cardiovascular disease, the genes may also be involved in mechanisms important to additional cardiovascular processes.

The invention includes the products of such fingerprint, target, and pathway genes, as well as antibodies to such gene products. Furthermore, the engineering and use of cell- and animal-based models of cardiovascular disease to which such gene products may contribute are also described.

The present invention encompasses methods for prognostic and diagnostic evaluation of cardiovascular, fibroproliferative and oncogenic related disease conditions, and for the identification of subjects exhibiting a predisposition to such conditions. Furthermore, the invention provides methods for evaluating the efficacy of drugs, and monitoring the progress of patients, involved in clinical trials for the treatment of cardiovascular, fibroproliferative and oncogenic related diseases.

The invention also provides methods for the identification of compounds that modulate the expression of genes or the activity of gene products involved in cardiovascular disease, as well as methods for the treatment of cardiovascular disease which may involve the administration of such compounds to individuals exhibiting cardiovascular disease symptoms or tendencies.

The invention also provides methods for the identification of compounds that modulate the expression of genes or the activity of gene products involved in fibroproliferative or oncogenic disorders, including tumorigenesis and the vascularization of tumors.

The invention is based, in part, on systematic search strategies involving in vivo and in vitro cardiovascular disease paradigms coupled with sensitive and high throughput gene expression assays. In contrast to approaches that merely evaluate the expression of a given gene product presumed to play a role in a disease process, the search strategies and assays used herein permit the identification of all genes, whether known or novel, that are expressed or repressed in the disease condition, as well as the evaluation of their temporal regulation and function during disease progression. This comprehensive approach and evaluation permits the discovery of novel genes and gene products, as well as the identification of an array of genes and gene products (whether novel or known) involved in novel pathways that play a major role in the disease pathology. Thus, the invention allows one to define targets useful for diagnosis, monitoring, rational drug screening and design, and/or other therapeutic intervention.

In the working examples described herein, five novel human genes are identified that are demonstrated to be differentially expressed in different cardiovascular disease states. The identification of these genes and the characterization of their expression in particular disease states provide newly identified roles in cardiovascular disease for these genes.

Specifically, fchd531, fchd540, and fchd545 are novel genes that are each differentially regulated in endothelial cells subjected to shear stress. fchd531 and fchd545 are each down-regulated, whereas fchd540 is up-regulated by shear stress. fchd602 and fchd605 are novel genes that are each up-regulated in monocytes treated with oxidized LDL. Accordingly, methods are provided for the diagnosis, monitoring in clinical trials, screening for therapeutically effective compounds, and treatment of cardiovascular disease based upon the discoveries herein regarding the expression patterns of fchd531, fchd540, fchd545, fchd602, and fchd605.

Both fchd540 and rchd534 are up-regulated in response to laminar shear stress and are specifically expressed in vascular tissue. fchd540 is also shown herein to be upregulated in oncogenic related disorders, such as pancreatic cancers. Further, overexpression of fchd540 expression constructs in pancreatic cells results in complete loss of the TGF-β response in such cells. These findings combined with the observations that both fchd540 and rchd534 specifically inhibit TGF-β signalling and that these genes are located in an area of the human genome implicated in the pathogenesis of several human malignancies indicates that they are excellent and specific targets for therapeutic intervention in the treatment of fibroproliferative and oncogenic disorders including tumorigenesis and vascularization.

The characteristic up-regulation of genes fchd540, fchd602, and fchd605 can be used to design cardiovascular disease treatment strategies. For those up-regulated genes that have a causative effect on the disease conditions, treatment methods can be designed to reduce or eliminate their expression, particularly in endothelial cells or monocytes. Alternatively, treatment methods include inhibiting the activity of the protein products of these genes. For those up-regulated genes that have a protective effect, treatment methods can be designed for enhancing the activity of the products of such genes.

In either situation, detecting expression of these genes in excess of normal expression provides for the diagnosis of cardiovascular disease. Furthermore, in testing the efficacy of compounds during clinical trials, a decrease in the level of the expression of these genes corresponds to a return from a disease condition to a normal state, and thereby indicates a positive effect of the compound. The cardiovascular diseases that may be so diagnosed, monitored in clinical trials, and treated include but are not limited to atherosclerosis, ischemia/reperfusion, hypertension, restenosis, and arterial inflammation.

The characteristic down-regulation of fchd531 and fchd545 can also be used to design cardiovascular disease treatment strategies. For those genes whose down-regulation has a pathogenic effect, treatment methods can be designed to restore or increase their expression, particularly in endothelial cells. Alternatively, treatment methods include increasing the activity of the protein products of these genes. For those genes whose down-regulation has a protective effect, treatment methods can be designed for decreasing the amount or activity of the products of such genes.

In either situation, detecting expression of these genes in below normal expression provides for the diagnosis of cardiovascular disease. Furthermore, in testing the efficacy of compounds during clinical trials, an increase in the level of the expression of these genes corresponds to a return from a disease condition to a normal state, and thereby indicates a positive effect of the compound. The cardiovascular diseases that may be so diagnosed, monitored in clinical trials, and treated include but are not limited to atherosclerosis, ischemia/reperfusion, hypertension, restenosis, and arterial inflammation.

The invention encompasses methods for screening compounds and other substances for treating cardiovascular disease by assaying their ability to modulate the expression of the target genes disclosed herein or activity of the protein products of the target genes. The invention further encompasses methods for screening compounds and other substances for treating fibroproliferative disorders and oncogenic disorders by assaying their ability to modulate the expression of the target genes disclosed herein or activity of the protein products of the target genes. Such screening methods include, but are not limited to, assays for identifying compounds and other substances that interact with (e.g., bind to) the target gene protein products.

In addition, the invention encompasses methods for treating cardiovascular, fibroproliferative and oncogenic related diseases by administering compounds and other substances that modulate the overall activity of the target gene products. Compounds and other substances can effect such modulation either on the level of target gene expression or target protein activity.

The invention is based in part on the identification of novel protein-protein interactions of the rchd534 protein with itself and with the fchd540 protein, as well as interactions of the rchd534 protein or the fchd540 protein with other protein members of the TGF-β signalling pathway. The rchd534 gene was described in Applicant's co-pending application Ser. No. 08/485,573, filed Jun. 7, 1995, which is hereby incorporated by reference in its entirety. Screening methods are provided for identifying compounds and other substances for treating cardiovascular disease by assaying their ability to inhibit these interactions. Furthermore, methods are provided for identifying compounds and other substances that enhance the TGF-β response by modulating the activity or the expression of the rchd534 or fchd540 genes or the activity of their gene products, for the treatment of fibroproliferative and oncogenic disease. For example, an increase in activity or expression of fchd540 can contribute to proliferative and oncogenic disorders by inhibiting the TGF-β response. Therapeutic targets that activate or enhance the TGF-β response as mediated through, e.g., fchd540, rchd534 or other TGF-β signaling protein are of significant use. In addition, methods are provided for treating cardiovascular disease by administering compounds and other substances that inhibit these protein interactions.

The invention is based in part on the identification of the endothelial cell specific expression pattern of two genes, rchd534 and fchd540, whose protein products inhibit the TGF-β response. The fchd540 gene has been mapped to regions of the human genome that have been implicated in the pathogenesis of several human malignancies. The invention is further based on the finding that these genes and mutants thereof may be used to modulate TGF-β induced signalling in endothelial cells. Accordingly, the rchd534 and rchd540 genes may be targets for intervention in a variety of inflammatory and fibroproliferative disorders that involve endothelial cells, including, but not limited to, oncology related disorders, disorders related to vascularization, such as cancer angiogenesis, inflammation, and fibrosis.

Membrane bound target gene products containing extracellular domains can be a particularly useful target for treatment methods as well as diagnostic and clinical monitoring methods. The fchd602 gene, for example, encodes a transmembrane protein, which contains multiple transmembrane domains and, therefore, can be readily contacted by other compounds on the cell surface. Accordingly, natural ligands, derivatives of natural ligands, and antibodies that bind to the fchd602 gene product can be utilized to inhibit its activity, or alternatively, to target the specific destruction of cells that express the gene. Furthermore, the extracellular domains of the fchd602 gene product provide targets which allow for the design of especially efficient screening systems for identifying compounds that bind to the fchd602 gene product.

Such an assay system can also be used to screen and identify antagonists of the interaction between the fchd602 gene product and ligands that bind to the fchd602 gene product. For example, the compounds can act as decoys by binding to the endogenous (i.e., natural) ligand for the fchd602 gene product. The resulting reduction in the amount of ligand-bound fchd602 gene transmembrane protein will modulate the activity of disease state cells, such as monocytes. Soluble proteins or peptides, such as peptides comprising one or more of the extracellular domains, or portions and/or analogs thereof of the fchd602 gene product, including, for example, soluble fusion proteins such as Ig-tailed fusion proteins, can be particularly useful for this purpose.

Similarly, antibodies that are specific to one or more of the extracellular domains of the fchd602 product provide for the ready detection of this target gene product in diagnostic tests or in clinical test monitoring. Accordingly, endothelial cells can be treated, either in vivo or in vitro, with such a labeled antibody to determine the disease state of endothelial cells. Because the fchd602 gene product is up-regulated in monocytes in the disease state, its detection positively corresponds with cardiovascular disease.

Such methods for treatment, diagnosis, and clinical test monitoring which use the fchd602 gene product as described above can also be applied to other target genes that encode transmembrane gene products, including but not limited to the fchd545 gene, which encodes multiple transmembrane domains and extracellular domains.

The examples presented in Sections 6 and 7, below, demonstrate the use of the cardiovascular disease paradigms of the invention to identify cardiovascular disease target genes.

The example presented in Section 8, below, demonstrates the use of fingerprint genes in diagnostics and as surrogate markers for testing the efficacy of candidate drugs in basic research and in clinical trials.

The example presented in Section 9, below, demonstrates the use of fingerprint genes, particularly fchd545, in the imaging of a diseased cardiovascular tissue.

The example presented in Section 11, below, demonstrates the interaction of two target gene products, the rchd534 and fchd540 proteins, and the further characterization of their roles in oncology, angiogenesis, cardiovascular disease and the TGF-β signalling pathway.

The example presented in Section 13, below, demonstrates that fchd540 can be overexpressed in oncorgenic related disorders such as pancreatic cancers, and shows that overexpression of fchd540 constructs in pancreatic cell lines results in completely loss of the TGF-β response.

4. DESCRIPTION OF THE FIGURES

FIGS. 1A–1D. Nucleotide sequence (SEQ ID NO:1) and encoded amino acid sequence (SEQ ID NO:7) of the fchd531 gene.

FIGS. 2A–2E. Nucleotide sequence (SEQ ID NO:2) and encoded amino acid sequence (SEQ ID NO:8) of the fchd540 gene.

FIGS. 3A–3C. Nucleotide sequence (SEQ ID NO:3) and encoded amino acid sequence (SEQ ID NO:9) of the fchd545 gene.

FIGS. 4A–4B. Nucleotide sequence and (SEQ ID NO:4) encoded amino acid sequence (SEQ ID NO:10) from the fchd602 gene.

FIGS. 5A–5B. Nucleotide sequence (SEQ ID NO:5) and encoded amino acid sequence (SEQ ID NO:11) from the fchd605 gene.

FIGS. 6A–6D. Nucleotide sequence and (SEQ ID NO:6) encoded amino acid sequence (SEQ ID NO:12) of the rchd534 gene.

Figure 7B:
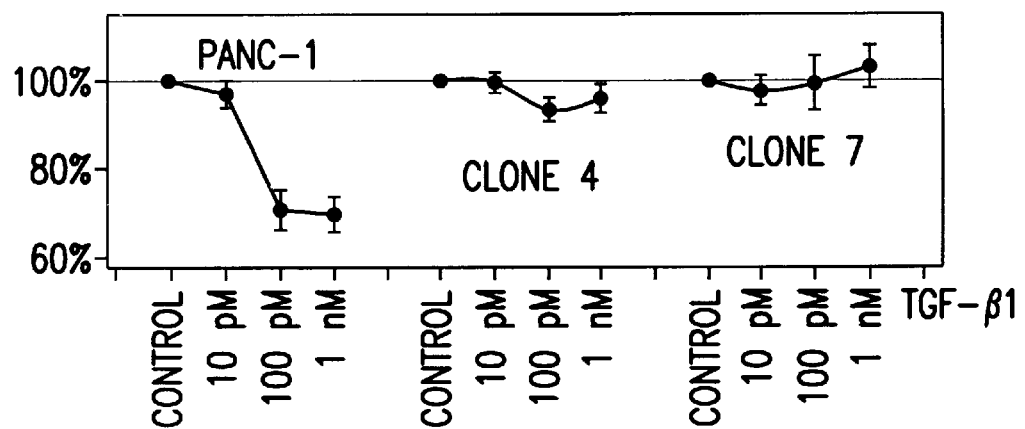

FIGS. 7A–7B. Effects of fchd540 on TGF-β1 mediated growth inhibition.

Figure 8A:
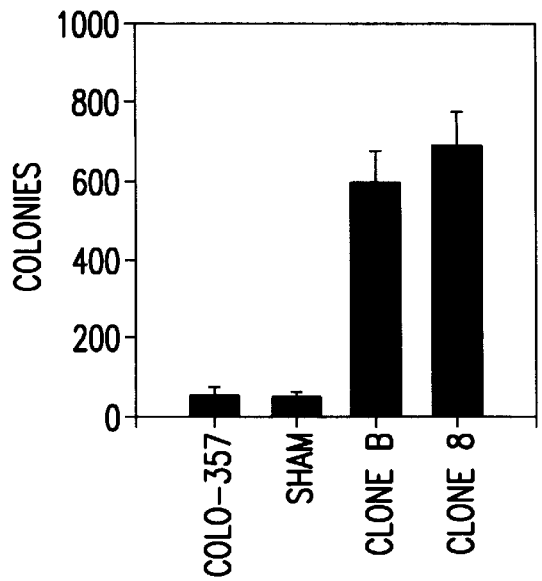
Figure 8B:
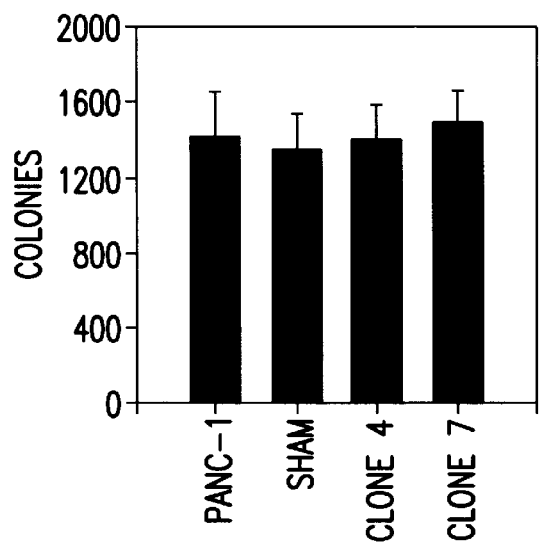
Figure 8C:
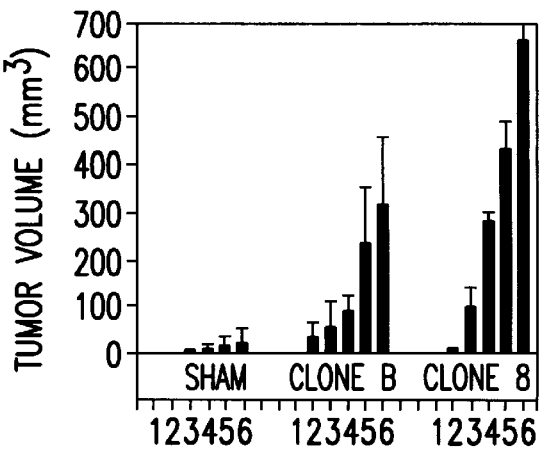

FIGS. 8A–8C. Anchorage independent growth of fchd540 transfected cell lines.

5. DETAILED DESCRIPTION OF THE INVENTION

Methods and compositions for the diagnosis and treatment of cardiovascular disease, including but not limited to atherosclerosis, ischemia/reperfusion, hypertension, restenosis, and arterial inflammation, are described. Methods and compositions for the treatment of oncogenic related disorders, including tumorigenesis and the vascularization of tumors, are also described. The invention is based, in part, on the evaluation of the expression and role of all genes that are differentially expressed in paradigms that are physiologically relevant to the disease condition. This permits the definition of disease pathways and the identification of targets in the pathway that are useful both diagnostically and therapeutically.

Genes, termed "target genes" and/or "fingerprint genes" which are differentially expressed in cardiovascular disease conditions, relative to their expression in normal, or non-cardiovascular disease conditions, are described in Section 5.4. Additionally, genes, termed "pathway genes" whose gene products exhibit an ability to interact with gene products involved in cardiovascular disease are also described in Section 5.4. Pathway genes may additionally have fingerprint and/or target gene characteristics. Methods for the identification of such fingerprint, target, and pathway genes are described in Sections 5.1, 5.2, and 5.3.

Further, the gene products of such fingerprint, target, and pathway genes are described in Section 5.4.2, antibodies to such gene products are described in Section 5.4.3, as are cell- and animal-based models of cardiovascular disease and oncogenic related disorders to which such gene products may contribute, in Section 5.4.4.

Methods for the identification of compounds which modulate the expression of genes or the activity of gene products involved in cardiovascular disease and fibroproliferative and oncogenic related disorders including tumorigenesis are described in Section 5.5. Methods for monitoring the efficacy of compounds during clinical trials are described in Section 5.5.4. Additionally described below, in Section 5.6, are methods for the treatment of cardiovascular disease and oncogenic related disorders.

Also discussed below, in Section 5.8, are methods for prognostic and diagnostic evaluation of cardiovascular disease, including the identification of subjects exhibiting a predisposition to this disease, and the imaging of cardiovascular disease conditions.

5.1. IDENTIFICATION OF DIFFERENTIALLY EXPRESSED GENES

This section describes methods for the identification of genes which are involved in cardiovascular disease, including but not limited to atherosclerosis, ischemia/reperfusion, hypertension, restenosis, and arterial inflammation. Such genes may represent genes which are differentially expressed in cardiovascular disease conditions relative to their expression in normal, or non-cardiovascular disease conditions. Such differentially expressed genes may represent "target" and/or "fingerprint" genes. Methods for the identification of such differentially expressed genes are described, below, in this section. Methods for the further characterization of such differentially expressed genes, and for their identification as target and/or fingerprint genes, are presented, below, in Section 5.3.

"Differential expression" as used herein refers to both quantitative as well as qualitative differences in the genes' temporal and/or tissue expression patterns. Thus, a differentially expressed gene may have its expression activated or completely inactivated in normal versus cardiovascular disease conditions (e.g., treated with oxidized LDL versus untreated), or under control versus experimental conditions. Such a qualitatively regulated gene will exhibit an expression pattern within a given tissue or cell type which is detectable in either control or cardiovascular disease subjects, but is not detectable in both. Alternatively, such a qualitatively regulated gene will exhibit an expression pattern within a given tissue or cell type which is detectable in either control or experimental subjects, but is not detectable in both. "Detectable", as used herein, refers to an RNA expression pattern which is detectable via the standard techniques of differential display, reverse transcriptase-(RT-) PCR and/or Northern analyses, which are well known to those of skill in the art.

Alternatively, a differentially expressed gene may have its expression modulated, i.e., quantitatively increased or decreased, in normal versus cardiovascular disease states, or under control versus experimental conditions. The degree to which expression differs in normal versus cardiovascular disease or control versus experimental states need only be large enough to be visualized via standard characterization techniques, such as, for example, the differential display technique described below. Other such standard characterization techniques by which expression differences may be visualized include but are not limited to quantitative RT-PCR and Northern analyses.

Differentially expressed genes may be further described as target genes and/or fingerprint genes. "Fingerprint gene," as used herein, refers to a differentially expressed gene whose expression pattern may be utilized as part of a prognostic or diagnostic cardiovascular disease evaluation, or which, alternatively, may be used in methods for identifying compounds useful for the treatment of cardiovascular disease. A fingerprint gene may also have the characteristics of a target gene.

"Target gene", as used herein, refers to a differentially expressed gene involved in cardiovascular disease in a manner by which modulation of the level of target gene expression or of target gene product activity may act to ameliorate symptoms of cardiovascular disease. A target gene may also have the characteristics of a fingerprint gene.

A variety of methods may be utilized for the identification of genes which are involved in cardiovascular disease. These methods include but are not limited to the experimental paradigms described, below, in Section 5.1.1. Material from the paradigms may be characterized for the presence of differentially expressed gene sequences as discussed, below, in Section 5.1.2.

5.1.1. PARADIGMS FOR THE IDENTIFICATION OF DIFFERENTIALLY EXPRESSED GENES

One strategy for identifying genes that are involved in cardiovascular disease is to detect genes that are expressed differentially under conditions associated with the disease versus non-disease conditions. The sub-sections below describe a number of experimental systems, called paradigms, which may be used to detect such differentially expressed genes. In general, the paradigms include at least one experimental condition in which subjects or samples are treated in a manner associated with cardiovascular disease, in addition to at least one experimental control condition lacking such disease associated treatment. Differentially expressed genes are detected, as described herein, below, by comparing the pattern of gene expression between the experimental and control conditions.

Once a particular gene has been identified through the use of one such paradigm, its expression pattern may be further characterized by studying its expression in a different paradigm. A gene may, for example, be regulated one way in a given paradigm (e.g., up-regulation), but may be regulated differently in some other paradigm (e.g., down-regulation). Furthermore, while different genes may have similar expression patterns in one paradigm, their respective expression patterns may differ from one another under a different paradigm. Such use of multiple paradigms may be useful in distinguishing the roles and relative importance of particular genes in cardiovascular disease.

5.1.1.1. FOAM CELL PARADIGM—1

Among the paradigms which may be utilized for the identification of differentially expressed genes involved in atherosclerosis, for example, are paradigms designed to analyze those genes which may be involved in foam cell formation. Such paradigms may serve to identify genes involved in the differentiation of this cell type, or their ptake of oxidized LDL.

One embodiment of such a paradigm, hereinafter referred to as Paradigm A, is carried out as follows: First, human blood is drawn and peripheral monocytes are isolated by methods routinely practiced in the art. These human monocytes can then be used immediately or cultured in vitro, using methods routinely practiced in the art, for 5 to 9 days where they develop more macrophage-like characteristics such as the up-regulation of scavenger receptors. These cells are then treated for various lengths of time with agents thought to be involved in foam cell formation. These agents include but are not limited to oxidized LDL, acetylated LDL, lysophosphatidylcholine, and homocysteine. Control monocytes that are untreated or treated with native LDL are grown in parallel. At a certain time after addition of the test agents, the cells are harvested and analyzed for differential expression as described in detail in Section 5.1.2., below. The Example presented in Section 6, below, demonstrates in detail the use of such a foam cell paradigm to identify genes which are differentially expressed in treated versus control cells.

5.1.1.2. FOAM CELL PARADIGM—2

Alternative paradigms involving monocytes for detecting differentially expressed genes associated with atherosclerosis involve the simulation of the phenomenon of transmigration. When monocytes encounter arterial injury, they adhere to the vascular endothelial layer, transmigrate across this layer, and locate between the endothelium and the layer of smooth muscle cells that ring the artery. This phenomenon can be mimicked in vitro by culturing a layer of endothelial cells isolated, for example, from human umbilical cord. Once the endothelial monolayer forms, monocytes drawn from peripheral blood are cultured on top of the endothelium in the presence and absence of LDL. After several hours, the monocytes transmigrate through the endothelium and develop into foam cells after 3 to 5 days when exposed to LDL. In this system, as in vivo, the endothelial cells carry out the oxidation of LDL which is then taken up by the monocytes. As described in sub-section 5.1.2. below, the pattern of gene expression can then be compared between these foam cells and untreated monocytes.

5.1.1.3. FOAM CELL PARADIGM—3

Yet another system includes the third cell type, smooth muscle cell, that plays a critical role in atherogenesis (Navab et al., 1988, J. Clin. Invest., 82: 1853). In this system, a multilayer of human aortic smooth muscle cells was grown on a micropore filter covered with a gel layer of native collagen, and a monolayer of human aortic endothelial cells was grown on top of the collagen layer. Exposure of this coculture to human monocytes in the presence of chemotactic factor rFMLP resulted in monocyte attachment to the endothelial cells followed by migration across the endothelial monolayer into the collagen layer of the subendothelial space. This type of culture can also be treated with LDL to generate foam cells. The foam cells can then be harvested and their pattern of gene expression compared to that of untreated cells as explained below in sub-section 5.1.2.

5.1.1.4. IN VIVO MONOCYTE PARADIGM

An alternative embodiment of such paradigms for the study of monocytes, hereinafter referred to as Paradigm B, involves differential treatment of human subjects through the dietary control of lipid consumption. Such human subjects are held on a low fat/low cholesterol diet for three weeks, at which time blood is drawn, monocytes are isolated according to the methods routinely practiced in the art, and RNA is purified, as described below, in sub-section 5.1.2. These same patients are subsequently switched to a high fat/high cholesterol diet and monocyte RNA is purified again. The patients may also be fed a third, combination diet containing high fat/low cholesterol and monocyte RNA may be purified once again. The order in which patients receive the diets may be varied. The RNA derived from patients maintained on two of the diets, or on all three diets, may then be compared and analyzed for differential gene expression as, explained below in sub-section 5.1.2.

5.1.1.5. ENDOTHELIAL CELL—IL-1 PARADIGM

In addition to the detection of differential gene expression in monocytes, paradigms focusing on endothelial cells may be used to detect genes involved in cardiovascular disease. In one such paradigm, hereinafter referred to as Paradigm C, human umbilical vein endothelial cells (HUVEC's) are grown in vitro. Experimental cultures are treated with human IL-1$\beta$, a factor known to be involved in the inflammatory response, in order to mimic the physiologic conditions involved in the atherosclerotic state. Alternatively experimental HUVEC cultures may be treated with lysophosphatidylcholine, a major phospholipid component of atherogenic lipoproteins or oxidized human LDL. Control cultures are grown in the absence of these compounds.

After a certain period of treatment, experimental and control cells are harvested and analyzed for differential gene expression as described in sub-section 5.1.2, below.

5.1.1.6. ENDOTHELIAL CELL—SHEAR STRESS PARADIGM

In another paradigm involving endothelial cells, hereinafter referred to as Paradigm D, cultures are exposed to fluid shear stress which is thought to be responsible for the prevalence of atherosclerotic lesions in areas of unusual circulatory flow. Unusual blood flow also plays a role in the harmful effects of ischemia/reperfusion, wherein an organ receiving inadequate blood supply is suddenly reperfused with an overabundance of blood when the obstruction is overcome.

Cultured HUVEC monolayers are exposed to laminar shear stress by rotating the culture in a specialized apparatus containing liquid culture medium (Nagel et al., 1994, J. Clin. Invest. 94: 885–891). Static cultures grown in the same medium serve as controls. After a certain period of exposure to shear stress, experimental and control cells are harvested and analyzed for differential gene expression as described in sub-section 5.1.2, below. The Example presented in Section 7, below, demonstrates the use of such a shear stressed endothelial cell paradigm to identify sequences which are differentially expressed in exposed versus control cells.

In all such paradigms designed to identify genes which are involved in cardiovascular disease, including but not limited to those described above in Sections 5.1.1.1 through 5.1.1.6, compounds such as drugs known to have an ameliorative effect on the disease symptoms may be incorporated into the experimental system. Such compounds may include known therapeutics, as well as compounds that are not useful as therapeutics due to their harmful side effects. Test cells that are cultured as explained in the paradigms described in Sections 5.1.1.1 through 5.1.1.6, for example, may be exposed to one of these compounds and analyzed for differential gene expression with respect to untreated cells, according to the methods described below in Section 5.1.2. In principle, according to the particular paradigm, any cell type involved in the disease may be treated at any stage of the disease process by these compounds.

Test cells may also be compared to unrelated cells (e.g., fibroblasts) that are also treated with the compound, in order to screen out generic effects on gene expression that might not be related to the disease. Such generic effects might be manifest by changes in gene expression that are common to the test cells and the unrelated cells upon treatment with the compound.

By these methods, the genes and gene products upon which these compounds act can be identified and used in the assays described below to identify novel therapeutic compounds for the treatment of cardiovascular disease.

5.1.2. ANALYSIS OF PARADIGM MATERIAL

In order to identify differentially expressed genes, RNA, either total or mRNA, may be isolated from one or more tissues of the subjects utilized in paradigms such as those described earlier in this Section. RNA samples are obtained from tissues of experimental subjects and from corresponding tissues of control subjects. Any RNA isolation technique which does not select against the isolation of mRNA may be utilized for the purification of such RNA samples. See, for example, Sambrook et al., 1989, Molecular Cloning, A Laboratory Manual, Cold Spring Harbor Press, N.Y.; and Ausubel, F. M. et al., eds., 1987–1993, Current Protocols in Molecular Biology, John Wiley & Sons, Inc. New York, both of which are incorporated herein by reference in their entirety. Additionally, large numbers of tissue samples may readily be processed using techniques well known to those of skill in the art, such as, for example, the single-step RNA isolation process of Chomczynski, P. (1989, U.S. Pat. No. 4,843,155), which is incorporated herein by reference in its entirety.

Transcripts within the collected RNA samples which represent RNA produced by differentially expressed genes may be identified by utilizing a variety of methods which are well known to those of skill in the art. For example, differential screening (Tedder, T. F. et al., 1988, Proc. Natl. Acad. Sci. USA 85:208–212), subtractive hybridization (Hedrick, S. M. et al., 1984, Nature 308:149–153; Lee, S. W. et al., 1984, Proc. Natl. Acad. Sci. USA 88:2825), and, preferably, differential display (Liang, P., and Pardee, A. B., 1993, U.S. Pat. No. 5,262,311, which is incorporated herein by reference in its entirety), may be utilized to identify nucleic acid sequences derived from genes that are differentially expressed.

Differential screening involves the duplicate screening of a cDNA library in which one copy of the library is screened with a total cell cDNA probe corresponding to the mRNA population of one cell type while a duplicate copy of the cDNA library is screened with a total cDNA probe corresponding to the mRNA population of a second cell type. For example, one cDNA probe may correspond to a total cell cDNA probe of a cell type derived from a control subject, while the second cDNA probe may correspond to a total cell cDNA probe of the same cell type derived from an experimental subject. Those clones which hybridize to one probe but not to the other potentially represent clones derived from genes differentially expressed in the cell type of interest in control versus experimental subjects.

Subtractive hybridization techniques generally involve the isolation of mRNA taken from two different sources, e.g., control and experimental tissue, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two mRNA sources. Such single-stranded cDNAs are then used as the starting material for the construction of a library comprising clones derived from differentially expressed genes.

The differential display technique describes a procedure, utilizing the well known polymerase chain reaction (PCR; the experimental embodiment set forth in Mullis, K. B., 1987, U.S. Pat. No. 4,683,202) which allows for the identification of sequences derived from genes which are differentially expressed. First, isolated RNA is reverse-transcribed into single-stranded cDNA, utilizing standard techniques which are well known to those of skill in the art. Primers for the reverse transcriptase reaction may include, but are not limited to, oligo dT-containing primers, preferably of the reverse primer type of oligonucleotide described below. Next, this technique uses pairs of PCR primers, as described below, which allow for the amplification of clones representing a random subset of the RNA transcripts present within any given cell. Utilizing different pairs of primers allows each of the mRNA transcripts present in a cell to be amplified. Among such amplified transcripts may be identified those which have been produced from differentially expressed genes.

The reverse oligonucleotide primer of the primer pairs may contain an oligo dT stretch of nucleotides, preferably eleven nucleotides long, at its 5' end, which hybridizes to the poly(A) tail of mRNA or to the complement of a cDNA reverse transcribed from an mRNA poly(A) tail. Second, in order to increase the specificity of the reverse primer, the primer may contain one or more, preferably two, additional nucleotides at its 3' end. Because, statistically, only a subset of the mRNA derived sequences present in the sample of interest will hybridize to such primers, the additional nucleotides allow the primers to amplify only a subset of the mRNA derived sequences present in the sample of interest. This is preferred in that it allows more accurate and complete visualization and characterization of each of the bands representing amplified sequences.

The forward primer may contain a nucleotide sequence expected, statistically, to have the ability to hybridize to cDNA sequences derived from the tissues of interest. The nucleotide sequence may be an arbitrary one, and the length of the forward oligonucleotide primer may range from about 9 to about 13 nucleotides, with about 10 nucleotides being preferred. Arbitrary primer sequences cause the lengths of the amplified partial cDNAs produced to be variable, thus allowing different clones to be separated by using standard denaturing sequencing gel electrophoresis. PCR reaction conditions should be chosen which optimize amplified product yield and specificity, and, additionally, produce amplified products of lengths which may be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times.

The pattern of clones resulting from the reverse transcription and amplification of the mRNA of two different cell types is displayed via sequencing gel electrophoresis and compared. Differences in the two banding patterns indicate potentially differentially expressed genes.

Once potentially differentially expressed gene sequences have been identified via bulk techniques such as, for example, those described above, the differential expression of such putatively differentially expressed genes should be corroborated. Corroboration may be accomplished via, for example, such well known techniques as Northern analysis and/or RT-PCR.

Upon corroboration, the differentially expressed genes may be further characterized, and may be identified as target and/or fingerprint genes, as discussed, below, in Section 5.3.

Also, amplified sequences of differentially expressed genes obtained through, for example, differential display may be used to isolate full length clones of the corresponding gene. The full length coding portion of the gene may readily be isolated, without undue experimentation, by molecular biological techniques well known in the art. For example, the isolated differentially expressed amplified fragment may be labeled and used to screen a cDNA library. Alternatively, the labeled fragment may be used to screen a genomic library.

PCR technology may also be utilized to isolate full length cDNA sequences. As described, above, in this Section, the isolated, amplified gene fragments obtained through differential display have 5' terminal ends at some random point within the gene and have 3' terminal ends at a position preferably corresponding to the 3' end of the transcribed portion of the gene. Once nucleotide sequence information from an amplified fragment is obtained, the remainder of the gene (i.e., the 5' end of the gene, when utilizing differential display) may be obtained using, for example, RT-PCR.

In one embodiment of such a procedure for the identification and cloning of full length gene sequences, RNA may be isolated, following standard procedures, from an appropriate tissue or cellular source. A reverse transcription reaction may then be performed on the RNA using an oligonucleotide primer complimentary to the mRNA that corresponds to the amplified fragment, for the priming of first strand synthesis. Because the primer is anti-parallel to the mRNA, extension will proceed toward the 5' end of the mRNA. The resulting RNA/DNA hybrid may then be "tailed" with guanines using a standard terminal transferase reaction, the hybrid may be digested with RNAase H, and second strand synthesis may then be primed with a poly-C primer. Using the two primers, the 5' portion of the gene is amplified using PCR. Sequences obtained may then be isolated and recombined with previously isolated sequences to generate a full-length cDNA of the differentially expressed genes of the invention. For a review of cloning strategies and recombinant DNA techniques, see e.g., Sambrook et al., 1989, supra; and Ausubel et al., 1989, supra.

5.2. IDENTIFICATION OF PATHWAY GENES

This section describes methods for the identification of genes, termed "pathway genes", involved in cardiovascular disease. "Pathway gene", as used herein, refers to a gene whose gene product exhibits the ability to interact with gene products involved in cardiovascular disease. A pathway gene may be differentially expressed and, therefore, may additionally have the characteristics of a target and/or fingerprint gene.

Any method suitable for detecting protein-protein interactions may be employed for identifying pathway gene products by identifying interactions between gene products and gene products known to be involved in cardiovascular disease. Such known gene products may be cellular or extracellular proteins. Those gene products which interact with such known gene products represent pathway gene products and the genes which encode them represent pathway genes.

Among the traditional methods which may be employed are co-immunoprecipitation, crosslinking and co-purification through gradients or chromatographic columns. Utilizing procedures such as these allows for the identification of pathway gene products. Once identified, a pathway gene product may be used, in conjunction with standard techniques, to identify its corresponding pathway gene. For example, at least a portion of the amino acid sequence of the pathway gene product may be ascertained using techniques well known to those of skill in the art, such as via the Edman degradation technique (see, e.g., Creighton, 1983, Proteins: Structures and Molecular Principles, W.H. Freeman & Co., N.Y., pp.34–49). The amino acid sequence obtained may be used as a guide for the generation of oligonucleotide mixtures that can be used to screen for pathway gene sequences. Screening may be accomplished, for example by standard hybridization or PCR techniques. Techniques for the generation of oligonucleotide mixtures and screening are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of pathway genes which encode the protein interacting with a protein involved in cardiovascular disease. These methods include, for example, probing expression libraries with labeled protein known or suggested to be involved in cardiovascular disease, using this protein in a manner similar to the well known technique of antibody probing of $\lambda$gt11 libraries.

One such method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to a known protein, and the other consists of the activator protein's activation domain fused to an unknown protein that is encoded by a cDNA which has been recombined into this plasmid as part of a cDNA library. The plasmids are transformed into a strain of the yeast *Saccharomyces cerevisiae* that contains a reporter gene (e.g., lacZ) whose regulatory region contains the activator's binding sites. Either hybrid protein alone cannot activate transcription of the reporter gene; the DNA-binding domain hybrid, because it does not provide activation function and the activation domain hybrid, because it cannot localize to the activator's binding sites. Interaction of the two proteins reconstitutes the functional activator protein and results in expression of the reporter gene, which is detected by an assay for the reporter gene product.

The two-hybrid system or related methodology may be used to screen activation domain libraries for proteins that interact with a known "bait" gene protein. Total genomic or cDNA sequences may be fused to the DNA encoding an activation domain. Such a library and a plasmid encoding a hybrid of the bait gene protein fused to the DNA-binding domain may be cotransformed into a yeast reporter strain, and the resulting transformants may be screened for those that express the reporter gene. These colonies may be purified and the library plasmids responsible for reporter gene expression may be isolated. DNA sequencing may then be used to identify the proteins encoded by the library plasmids.

For example, and not by way of limitation, the bait gene may be cloned into a vector such that it is translationally fused to the DNA encoding the DNA-binding domain of the GAL4 protein. Also by way of example, for the isolation of genes involved in cardiovascular disease, previously isolated genes known or suggested to play a part in cardiovascular disease may be used as the bait genes. These include but are not limited to the genes for bFGF, IGF-I, VEGF, IL-1, M-CSF, TGF$\beta$, TGF$\alpha$, TNF$\alpha$, HB-EGF, PDGF, IFN-$\gamma$, and GM-CSF, to name a few.

A cDNA library of the cell line from which proteins that interact with bait gene are to be detected can be made using methods routinely practiced in the art. According to the particular system described herein, for example, the cDNA fragments may be inserted into a vector such that they are translationally fused to the activation domain of GAL4. This library may be co-transformed along with the bait gene-GAL4 fusion plasmid into a yeast strain which contains a lacZ gene driven by a promoter which contains the GAL4 activation sequence. A cDNA encoded protein, fused to the GAL4 activation domain, that interacts with bait gene will reconstitute an active GAL4 protein and thereby drive expression of the lacZ gene. Colonies which express lacZ may be detected by their blue color in the presence of X-gal. The cDNA may then be purified from these strains, and used to produce and isolate the bait gene-interacting protein using techniques routinely practiced in the art.

Once a pathway gene has been identified and isolated, it may be further characterized as, for example, discussed below, in Section 5.3.

A preferred embodiment of the use of the yeast two-hybrid system is described in detail in the example in Section 12, below. As described in Section 12, the yeast two-hybrid system was used to detect the interaction between the protein products of two target genes, rchd534 and fchd540.

5.3. CHARACTERIZATION OF DIFFERENTIALLY EXPRESSED AND PATHWAY GENES

Differentially expressed genes, such as those identified via the methods discussed, above, in Section 5.1.1, pathway genes, such as those identified via the methods discussed, above, in Section 5.2, as well as genes identified by alternative means, may be further characterized by utilizing, for example, methods such as those discussed herein. Such genes will be referred to herein as "identified genes".

Analyses such as those described herein will yield information regarding the biological function of the identified genes. An assessment of the biological function of the differentially expressed genes, in addition, will allow for their designation as target and/or fingerprint genes. Specifically, any of the differentially expressed genes whose further characterization indicates that a modulation of the gene's expression or a modulation of the gene product's activity may ameliorate cardiovascular disease will be designated "target genes", as defined, above, in Section 5.1. Such target genes and target gene products, along with those discussed below, will constitute the focus of the compound discovery strategies discussed, below, in Section 5.5.

Any of the differentially expressed genes whose further characterization indicates that such modulations may not positively affect cardiovascular disease, but whose expression pattern contributes to a gene expression "fingerprint pattern" correlative of, for example, a cardiovascular disease condition will be designated a "fingerprint gene". "Fingerprint patterns" will be more fully discussed, below, in Section 5.8. It should be noted that each of the target genes may also function as fingerprint genes, as may all or a subset of the pathway genes.

It should further be noted that the pathway genes may also be characterized according to techniques such as those described herein. Those pathway genes which yield information indicating that they are differentially expressed and that modulation of the gene's expression or a modulation of the gene product's activity may ameliorate cardiovascular disease will be also be designated "target genes". Such target genes and target gene products, along with those discussed above, will constitute the focus of the compound discovery strategies discussed, below, in Section 5.5.

It should be additionally noted that the characterization of one or more of the pathway genes may reveal a lack of differential expression, but evidence that modulation of the gene's activity or expression may, nonetheless, ameliorate cardiovascular disease symptoms. In such cases, these genes and gene products would also be considered a focus of the compound discovery strategies of Section 5.5, below.

In instances wherein a pathway gene's characterization indicates that modulation of gene expression or gene product activity may not positively affect cardiovascular disease, but whose expression is differentially expressed and which contributes to a gene expression fingerprint pattern correlative of, for example, a cardiovascular disease state, such pathway genes may additionally be designated as fingerprint genes.

Among the techniques whereby the identified genes may be further characterized, the nucleotide sequence of the identified genes, which may be obtained by utilizing standard techniques well known to those of skill in the art, may be used to further characterize such genes. For example, the sequence of the identified genes may reveal homologies to one or more known sequence motifs which may yield information regarding the biological function of the identified gene product.

Second, an analysis of the tissue distribution of the mRNA produced by the identified genes may be conducted, utilizing standard techniques well known to those of skill in the art. Such techniques may include, for example, Northern analyses and RT-PCR. Such analyses provide information as to whether the identified genes are expressed in tissues expected to contribute to cardiovascular disease. Such analyses may also provide quantitative information regarding steady state mRNA regulation, yielding data concerning which of the identified genes exhibits a high level of regulation in, preferably, tissues which may be expected to contribute to cardiovascular disease.

Such analyses may also be performed on an isolated cell population of a particular cell type derived from a given tissue. Additionally, standard in situ hybridization techniques may be utilized to provide information regarding which cells within a given tissue express the identified gene. Such analyses may provide information regarding the biological function of an identified gene relative to cardiovascular disease in instances wherein only a subset of the cells within the tissue is thought to be relevant to cardiovascular disease.

Third, the sequences of the identified genes may be used, utilizing standard techniques, to place the genes onto genetic maps, e.g., mouse (Copeland & Jenkins, 1991, Trends in Genetics 7: 113–118) and human genetic maps (Cohen, et al., 1993, Nature 366: 698–701). Such mapping information may yield information regarding the genes' importance to human disease by, for example, identifying genes which map near genetic regions to which known genetic cardiovascular disease tendencies map.

Fourth, the biological function of the identified genes may be more directly assessed by utilizing relevant in vivo and in vitro systems. In vivo systems may include, but are not limited to, animal systems which naturally exhibit cardiovascular disease predisposition, or ones which have been engineered to exhibit such symptoms, including but not limited to the apoE-deficient atherosclerosis mouse model (Plump et al., 1992, Cell 71: 343–353). Such systems are discussed in Section 5.4.4.1, below.

In vitro systems may include, but are not limited to, cell-based systems comprising cell types known or suspected of involvement in cardiovascular disease. Such systems are discussed in detail, below, in Section 5.4.4.2.

In further characterizing the biological function of the identified genes, the expression of these genes may be modulated within the in vivo and/or in vitro systems, i.e., either over- or underexpressed, and the subsequent effect on the system then assayed. Alternatively, the activity of the product of the identified gene may be modulated by either increasing or decreasing the level of activity in the in vivo and/or in vitro system of interest, and its subsequent effect then assayed.

The information obtained through such characterizations may suggest relevant methods for the treatment of cardiovascular disease involving the gene of interest. For example, treatment may include a modulation of gene expression and/or gene product activity. Characterization procedures such as those described herein may indicate where such modulation should involve an increase or a decrease in the expression or activity of the gene or gene product of interest.

For example, genes which are up-regulated under disease conditions may be involved in causing or exacerbating the disease condition. Treatments directed at down-regulating the activity of such harmfully expressed genes will ameliorate the disease condition. On the other hand, the up-regulation of genes under disease conditions may be part of a protective response by affected cells. Treatments directed at increasing or enhancing the activity of such up-regulated gene products, especially in individuals lacking normal up-regulation, will similarly ameliorate disease conditions. Such methods of treatment are discussed, below, in Section 5.6.

5.4. DIFFERENTIALLY EXPRESSED AND PATHWAY GENES

Identified genes, which include but are not limited to differentially expressed genes such as those identified in Section 5.1.1, above, and pathway genes, such as those identified in Section 5.2, above, are described herein. Specifically, the nucleic acid sequences and gene products of such identified genes are described herein. Further, antibodies directed against the identified genes' products, and cell- and animal-based models by which the identified genes may be further characterized and utilized are also discussed in this Section.

5.4.1. DIFFERENTIALLY EXPRESSED AND PATHWAY GENE SEQUENCES

The differentially expressed and pathway genes of the invention are listed below, in Table 1. Differentially expressed and pathway gene nucleotide sequences are shown in FIGS. 1–5.

Table 1 lists differentially expressed genes identified through, for example, the paradigms discussed, above, in Section 5.1.1, and below, in the examples presented in Sections 6 through 9. Table 1 also summarizes information regarding the further characterization of such genes.

First, the paradigm used initially to detect the differentially expressed gene is described under the column headed "Paradigm of Original Detection". The expression patterns of those genes which have been shown to be differentially expressed, for example, under one or more of the paradigm conditions described in Section 5.1.1 are summarized under the column headed "Paradigm Expression Pattern". For each of the tested genes, the paradigm which was used and the difference in the expression of the gene among the samples generated is shown. "↑" indicates that gene expression is up-regulated (i.e., there is an increase in the amount of detectable mRNA) among the samples generated, while "↓" indicates that gene expression is down-regulated (i.e., there is a decrease in the amount of detectable mRNA) among the samples generated. "Detectable" as used herein, refers to levels of mRNA which are detectable via, for example, standard Northern and/or RT-PCR techniques which are well known to those of skill in the art.

Cell types in which differential expression was detected are also summarized in Table 1 under the column headed "Cell Type Detected in". The column headed "Chromosomal Location" provides the human chromosome number on which the gene is located. Additionally, in instances wherein the genes contain nucleotide sequences similar or homologous to sequences found in nucleic acid databases, references to such similarities are listed.

The genes listed in Table 1 may be obtained using cloning methods well known to those skilled in the art, including but not limited to the use of appropriate probes to detect the genes within an appropriate cDNA or gDNA (genomic DNA) library. (See, for example, Sambrook et al., 1989, Molecular Cloning: A Laboratory Manual, Cold Spring Harbor Laboratories, which is incorporated by reference herein in its entirety). Probes for the novel sequences reported herein may be obtained directly from the isolated clones deposited with the ATCC, as indicated in Table 2, below. Alternatively, oligonucleotide probes for the novel genes may be synthesized based on the DNA sequences disclosed herein in FIGS. 1–5.

The sequence obtained from clones containing partial coding sequences or non-coding sequences can be used to obtain the entire coding region by using the RACE method (Chenchik, et al., 1995, CLONTECHniques (X) 1: 5–8; Barnes, 1994, Proc. Natl. Acad. Sci. USA 91: 2216–2220; and Cheng et al., Proc. Natl. Acad. Sci. USA 91: 5695–5699). Oligonucleotides can be designed based on the sequence obtained from the partial clone that can amplify a reverse transcribed mRNA encoding the entire coding sequence.

Alternatively, probes can be used to screen cDNA libraries prepared from an appropriate cell or cell line in which the gene is transcribed. For example, the genes described herein that were detected in monocytes may be cloned from a cDNA library prepared from monocytes isolated as described in Section 6.1.1, below.

The genes described herein that were detected in endothelial cells may also be cloned from a cDNA library constructed from endothelial cells isolated as described in Progress in Hemostasis and Thrombosis, Vol. 3, P. Spaet, editor, Grune & Stratton Inc., New York, 1–28. Alternatively, the genes may be retrieved from a human placenta cDNA library (Clontech Laboratories, Palo Alto, Calif.), according to Takahashi et al., 1990, supra; a HUVEC cDNA library as described in Jones et al. 1993, supra; or an acute lymphoblastic leukemia (SUP-B2) cDNA library as described in Cleary et al., 1986, supra, for example. Genomic DNA libraries can be prepared from any source.

TABLE 1

Differentially Expressed and Pathway Genes

| Gene | Seq. ID # | Paradigm of Original Detection | Paradigm Expr. Pattern | Cell Type Detected in | Ref | Seq. |
|---|---|---|---|---|---|---|
| fchd531 | 1 | D (Section 5.1.1.6) | ↓ | Endothelial | New,1 | FIG. 1A–1D |
| fchd540 | 2 | D | ↑ | Endothelial | New,2 | FIG. 2–2E |
| fchd545 | 3 | D | ↓ | Endothelial | New,3 | FIG. 3A–3C |
| fchd602 | 4 | A (Section 5.1.1.1) | ↑ | Monocytes | New,4 | FIG. 4A–4B |

TABLE 1-continued

Differentially Expressed and Pathway Genes

| Gene | Seq. ID # | Paradigm of Original Detection | Paradigm Expr. Pattern | Cell Type Detected in | Ref | Seq. |
|---|---|---|---|---|---|---|
| fchd605 | 5 | A | ↑ | Monocytes | New,5 | FIG. 5A–5B |

1. GenBank accession number U05343.
2. Drosohila Mothers against dpp (Mad), Sekelsky et al., 1995, Genetics 139: 1347–1358.
3. Human Voltage-dependent Anion channel, Blachly-Dyson, E., et al., 1993, J. Biol. Chem. 268: 1835–1841; and EST T24012
4. Rat Cl-6, Diamond, R. H., et al., 1993, J. Biol Chem. 268: 15185–15192.
5. Mouse gly96, Charles, C. H., et al., 1993, Oncogene 8: 797–801; and EST T49532.

Table 2, below, lists the strains of *E. coli* deposited with the ATCC that contain plasmids bearing the novel genes listed in Table 1.

TABLE 2

| GENE | Strain Deposited with ATCC |
|---|---|
| fchd531 | pFCHD531 |
| fchd540 | pFCHD540 |
| fchd545 | fchd545 |

As used herein, "differentially expressed gene" (i.e. target and fingerprint gene) or "pathway gene" refers to (a) a gene containing at least one of the DNA sequences disclosed herein (as shown in FIGS. 1–5), or contained in the clones listed in Table 2, as deposited with the ATCC; (b) any DNA sequence that encodes the amino acid sequence encoded by the DNA sequences disclosed herein (as shown in FIGS. 1–5), contained in the clones, listed in Table 2, as deposited with the ATCC or contained within the coding region of the gene to which the DNA sequences disclosed herein (as shown in FIGS. 1–5) or contained in the clones listed in Table 2, as deposited with the ATCC, belong; (c) any DNA sequence that hybridizes to the complement of the coding sequences disclosed herein, contained in the clones listed in Table 2, as deposited with the ATCC, or contained within the coding region of the gene to which the DNA sequences disclosed herein (as shown in FIGS. 1–5) or contained in the clones listed in Table 2, as deposited with the ATCC, belong, under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a gene product functionally equivalent to a gene product encoded by sequences contained within the clones listed in Table 2; and/or (d) any DNA sequence that hybridizes to the complement of the coding sequences disclosed herein, (as shown in FIGS. 1–5) contained in the clones listed in Table 2, as deposited with the ATCC or contained within the coding region of the gene to which DNA sequences disclosed herein (as shown in FIGS. 1–5) or contained in the clones, listed in Table 2, as deposited with the ATCC, belong, under less stringent conditions, such as moderately stringent conditions, e.g., washing in 0.2×SSC/0.1% SDS at 42° C. (Ausubel et al., 1989, supra), yet which still encodes a functionally equivalent gene product.

The invention also includes nucleic acid molecules, preferably DNA molecules, that hybridize to, and are therefore the complements of, the DNA sequences (a) through (c), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as target gene antisense molecules, useful, for example, in target gene regulation and/or as antisense primers in amplification reactions of target gene nucleic acid sequences. Further, such sequences may be used as part of ribozyme and/or triple helix sequences, also useful for target gene regulation. Still further, such molecules may be used as components of diagnostic methods whereby the presence of a cardiovascular disease-causing allele, may be detected.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. The invention includes fragments of any of the DNA sequences disclosed herein.

In addition to the gene sequences described above, homologues of such sequences, as may, for example be present in other species, may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

For example, the isolated differentially expressed gene sequence may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Further, a previously unknown differentially expressed or pathway gene-type sequence may be isolated by performing PCR using two degenerate oligonucleotide primer pools designed on the basis of amino acid sequences within the gene of interest. The template for the reaction may be cDNA obtained by reverse transcription of mRNA prepared from human or non-human cell lines or tissue known or suspected to express a differentially expressed or pathway gene allele.

The PCR product may be subcloned and sequenced to insure that the amplified sequences represent the sequences of a differentially expressed or pathway gene-like nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the differentially expressed or pathway gene identified is the normal, or wild type, gene, this gene may be used to isolate mutant alleles of the gene. Such an isolation is preferable in processes and disorders which are known or suspected to have a genetic basis. Mutant alleles may be isolated from individuals either known or suspected to have a genotype which contributes to cardiovascular disease symptoms. Mutant alleles and mutant allele products may then be utilized in the therapeutic and diagnostic assay systems described below.

A cDNA of the mutant gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof may then be labeled and used as a probed to identify the corresponding mutant allele in the library. The clone containing this gene may then be purified through methods routinely practiced in the art, and subjected to sequence analysis as described, above, in this Section.

Additionally, an expression library can be constructed utilizing DNA isolated from or cDNA synthesized from a tissue known to or suspected of expressing the gene of interest in an individual suspected of or known to carry the mutant allele. In this manner, gene products made by the putatively mutant tissue may be expressed and screened using standard antibody screening techniques in conjunction with antibodies raised against the normal gene product, as described, below, in Section 5.4.3. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis as described in this Section, above.

5.4.2. DIFFERENTIALLY EXPRESSED AND PATHWAY GENE PRODUCTS

Differentially expressed and pathway gene products include those proteins encoded by the differentially expressed and pathway gene sequences described in Section 5.4.1, above. Specifically, differentially expressed and pathway gene products may include differentially expressed and pathway gene polypeptides encoded by the differentially expressed and pathway gene sequences contained in the clones listed in Table 2, above, as deposited with the ATCC, or contained in the coding regions of the genes to which DNA sequences disclosed herein (in FIGS. 1–5) or contained in the clones, listed in Table 2, as deposited with the ATCC, belong, for example.

In addition, differentially expressed and pathway gene products may include proteins that represent functionally equivalent gene products. Such an equivalent differentially expressed or pathway gene product may contain deletions, additions or substitutions of amino acid residues within the amino acid sequence encoded by the differentially expressed or pathway gene sequences described, above, in Section 5.4.1, but which result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous differentially expressed or pathway gene products encoded by the differentially expressed or pathway gene sequences described in Section 5.4.1, above. Alternatively, when utilized as part of assays such as those described, below, in Section 5.5, "functionally equivalent" may refer to peptides capable of interacting with other cellular or extracellular molecules in a manner substantially similar to the way in which the corresponding portion of the endogenous differentially expressed or pathway gene product would.

The differentially expressed or pathway gene products may be produced by recombinant DNA technology using techniques well known in the art. Thus, methods for preparing the differentially expressed or pathway gene polypeptides and peptides of the invention by expressing nucleic acid encoding differentially expressed or pathway gene sequences are described herein. Methods which are well known to those skilled in the art can be used to construct expression vectors containing differentially expressed or pathway gene protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding differentially expressed or pathway gene protein sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the differentially expressed or pathway gene coding sequences of the invention. Such host-expression systems represent vehicles by which the coding sequences of interest may be produced and subsequently purified, but also represent cells which may, when transformed or transfected with the appropriate nucleotide coding sequences, exhibit the differentially expressed or pathway gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing differentially expressed or pathway gene protein coding sequences; yeast (e.g. *Saccharomyces, Pichia*) transformed with recombinant yeast expression vectors containing the differentially expressed or pathway gene protein coding sequences; insect cell systems infected with recombinant virus expression vectors (e.g., baculovirus) containing the differentially expressed or pathway gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing differentially expressed or pathway gene protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the differentially expressed or pathway gene protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the differentially expressed or pathway gene protein coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

In a preferred embodiment, full length cDNA sequences are appended with in-frame Bam HI sites at the amino terminus and Eco RI sites at the carboxyl terminus using standard PCR methodologies (Innis et al., 1990, supra) and ligated into the pGEX-2TK vector (Pharmacia, Uppsala, Sweden). The resulting cDNA construct contains a kinase recognition site at the amino terminus for radioactive labelling and glutathione S-transferase sequences at the carboxyl terminus for affinity purification (Nilsson, et al., 1985, EMBO J. 4: 1075; Zabeau and Stanley, 1982, EMBO J. 1: 1217.

In an insect system, *Autographa californica* nuclear polyhedrosis virus (AcNPV) is used as a vector to express foreign genes. The virus grows in *Spodoptera frugiperda* cells. The differentially expressed or pathway gene coding sequence may be cloned individually into non-essential regions (for example the polyhedrin gene) of the virus and placed under control of an AcNPV promoter (for example the polyhedrin promoter). Successful insertion of differentially expressed or pathway gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the differentially expressed or pathway gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing differentially expressed or pathway gene protein in infected hosts. (E.g., See Logan & Shenk, 1984, Proc. Natl. Acad. Sci. USA 81:3655–3659). Specific initiation signals may also be required for efficient translation of inserted differentially expressed or pathway gene coding sequences. These signals include the ATG initiation codon and adjacent sequences. In cases where an entire differentially expressed or pathway gene, including its own initiation codon and adjacent sequences, is inserted into the appropriate expression vector, no additional translational control signals may be needed. However, in cases where only a portion of the differentially expressed or pathway gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In a preferred embodiment, cDNA sequences encoding the full-length open reading frames are ligated into pCNVβ replacing the β-galactosidase gene such that cDNA expression is driven by the CMV promoter (Alam, 1990, Anal. Biochem. 188: 245–254; MacGregor & Caskey, 1989, Nucl. Acids Res. 17: 2365; Norton & Corrin, 1985, Mol. Cell. Biol. 5: 281).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the differentially expressed or pathway gene protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the differentially expressed or pathway gene protein. Such engineered cell lines may be particularly useful in screening and evaluation of compounds that affect the endogenous activity of the differentially expressed or pathway gene protein.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

An alternative fusion protein system allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$·nitriloacetic acid-agarose columns and histidine-tagged proteins are selectively eluted with imidazole-containing buffers.

When used as a component in assay systems such as those described, below, in Section 5.5, the differentially expressed or pathway gene protein may be labeled, either directly or indirectly, to facilitate detection of a complex formed between the differentially expressed or pathway gene protein and a test substance. Any of a variety of suitable labeling systems may be used including but not limited to radioisotopes such as $^{125}I$; enzyme labelling systems that generate a detectable colorimetric signal or light when exposed to substrate; and fluorescent labels.

Where recombinant DNA technology is used to produce the differentially expressed or pathway gene protein for such assay systems, it may be advantageous to engineer fusion proteins that can facilitate labeling, immobilization and/or detection.

Indirect labeling involves the use of a protein, such as a labeled antibody, which specifically binds to either a differentially expressed or pathway gene product. Such antibodies include but are not limited to polyclonal, monoclonal, chimeric, single chain, Fab fragments and fragments produced by an Fab expression library.

5.4.3. DIFFERENTIALLY EXPRESSED OR PATHWAY GENE PRODUCT ANTIBODIES

Described herein are methods for the production of antibodies capable of specifically recognizing one or more differentially expressed or pathway gene epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a fingerprint, target, or pathway gene in a biological sample, or, alternatively, as a method for the inhibition of abnormal target gene activity. Thus, such antibodies may be utilized as part of cardiovascular disease treatment methods, and/or may be used as part of diagnostic techniques whereby patients may be tested for abnormal levels of fingerprint, target, or pathway gene proteins, or for the presence of abnormal forms of the such proteins.

For the production of antibodies to a differentially expressed or pathway gene, various host animals may be immunized by injection with a differentially expressed or pathway gene protein, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

In a preferred embodiment, peptide sequences corresponding to amino sequences of target gene products were selected and submitted to Research Genetics (Huntsville, Ala.) for synthesis and antibody production. Peptides were modified as described (Tam, J. P., 1988, Proc. Natl. Acad. Sci. USA 85: 5409–5413; Tam, J. P., and Zavala, F., 1989, J. Immunol. Methods 124: 53–61; Tam, J. P., and Lu, Y. A., 1989, Proc. Natl. Acad. Sci. USA 86: 9084–9088), emulsified in an equal volume of Freund's adjuvant and injected into rabbits at 3 to 4 subcutaneous dorsal sites for a total volume of 1.0 ml (0.5 mg peptide) per immunization. The animals were boosted after 2 and 6 weeks and bled at weeks 4, 8, and 10. The blood was allowed to clot and serum was collected by centrifugation. The generation of polyclonal antibodies against the fchd545 gene product is described in detail in the example in Section 10, below.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, may be immunized by injection with differentially expressed or pathway gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce differentially expressed or pathway gene-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.4.4. CELL- AND ANIMAL-BASED MODEL SYSTEMS

Described herein are cell- and animal-based systems which act as models for cardiovascular disease. These systems may be used in a variety of applications. For example, the cell- and animal-based model systems may be used to further characterize differentially expressed and pathway genes, as described, above, in Section 5.3. Such further characterization may, for example, indicate that a differentially expressed gene is a target gene. Second, such assays may be utilized as part of screening strategies designed to identify compounds which are capable of ameliorating cardiovascular disease symptoms, as described, below, in Section 5.5.4. Thus, the animal- and cell-based models may be used to identify drugs, pharmaceuticals, therapies and interventions which may be effective in treating cardiovascular disease. In addition, as described in detail, below, in Section 5.7.1, such animal models may be used to determine the $LD_{50}$ and the $ED_{50}$ in animal subjects, and such data can be used to determine the in vivo efficacy of potential cardiovascular disease treatments.

5.4.4.1. ANIMAL-BASED SYSTEMS

Animal-based model systems of cardiovascular disease may include, but are not limited to, non-recombinant and engineered transgenic animals.

Non-recombinant animal models for cardiovascular disease may include, for example, genetic models. Such genetic cardiovascular disease models may include, for example, apoB or apoR deficient pigs (Rapacz, et al., 1986, Science 234:1573–1577) and Watanabe heritable hyperlipidemic (WHHL) rabbits (Kita et al., 1987, Proc. Natl. Acad. Sci USA 84: 5928–5931).

Non-recombinant, non-genetic animal models of atherosclerosis may include, for example, pig, rabbit, or rat models in which the animal has been exposed to either chemical wounding through dietary supplementation of LDL, or mechanical wounding through balloon catheter angioplasty, for example.

Additionally, animal models exhibiting cardiovascular disease symptoms may be engineered by utilizing, for example, target gene sequences such as those described, above, in Section 5.4.1, in conjunction with techniques for producing transgenic animals that are well known to those of skill in the art. For example, target gene sequences may be introduced into, and overexpressed in, the genome of the animal of interest, or, if endogenous target gene sequences are present, they may either be overexpressed or, alternatively, be disrupted in order to underexpress or inactivate target gene expression, such as described for the disruption of apoE in mice (Plump et al., 1992, Cell 71: 343–353).

In order to overexpress a target gene sequence, the coding portion of the target gene sequence may be ligated to a regulatory sequence which is capable of driving gene expression in the animal and cell type of interest. Such regulatory regions will be well known to those of skill in the art, and may be utilized in the absence of undue experimentation.

For underexpression of an endogenous target gene sequence, such a sequence may be isolated and engineered such that when reintroduced into the genome of the animal of interest, the endogenous target gene alleles will be inactivated. Preferably, the engineered target gene sequence is introduced via gene targeting such that the endogenous target sequence is disrupted upon integration of the engineered target gene sequence into the animal's genome. Gene targeting is discussed, below, in this Section.

Animals of any species, including, but not limited to, mice, rats, rabbits, guinea pigs, pigs, micro-pigs, goats, and non-human primates, e.g., baboons, monkeys, and chimpanzees may be used to generate cardiovascular disease animal models.

Any technique known in the art may be used to introduce a target gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the target gene transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of the nucleotide sequence of the endogenous target gene. The transgene may also be selectively introduced into a particular cell type, thus inactivating the endogenous gene of interest in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art. Recombinant methods for expressing target genes are described in Section 5.4.2, above.

Once transgenic animals have been generated, the expression of the recombinant target gene and protein may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of target gene-expressing tissue, may also be evaluated immunocytochemically using antibodies specific for the target gene transgene gene product of interest.

The target gene transgenic animals that express target gene mRNA or target gene transgene peptide (detected immunocytochemically, using antibodies directed against the target gene product's epitopes) at easily detectable levels should then be further evaluated to identify those animals which display characteristic cardiovascular disease symptoms. Such symptoms may include, for example, increased prevalence and size of fatty streaks and/or cardiovascular disease plaques.

Additionally, specific cell types within the transgenic animals may be analyzed and assayed for cellular phenotypes characteristic of cardiovascular disease. In the case of monocytes, such phenotypes may include but are not limited to increases in rates of LDL uptake, adhesion to endothelial cells, transmigration, foam cell formation, fatty streak formation, and production of foam cell specific products. Cellular phenotype assays are discussed in detail in Section 5.4.4.2, below. Further, such cellular phenotypes may include a particular cell type's fingerprint pattern of expression as compared to known fingerprint expression profiles of the particular cell type in animals exhibiting cardiovascular disease symptoms. Fingerprint profiles are described in detail in Section 5.8.1, below. Such transgenic animals serve as suitable model systems for cardiovascular disease.

Once target gene transgenic founder animals are produced, they may be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound target gene transgenics that express the target gene transgene of interest at higher levels because of the effects of additive expression of each target gene transgene; crossing of heterozygous transgenic animals to produce animals homozygous for a given integration site in order both to augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the target gene transgene and the development of cardiovascular disease symptoms. One such approach is to cross the target gene transgenic founder animals with a wild type strain to produce an F1 generation that exhibits cardiovascular disease symptoms. The F1 generation may then be inbred in order to develop a homozygous line, if it is found that homozygous target gene transgenic animals are viable.

5.4.4.2. CELL-BASED ASSAYS

Cells that contain and express target gene sequences which encode target gene protein, and, further, exhibit cellular phenotypes associated with cardiovascular disease, may be utilized to identify compounds that exhibit anti-cardiovascular disease activity.

Such cells may include non-recombinant monocyte cell lines, such as U937 (ATCC# CRL-1593), THP-1 (ATCC# TIB-202), and P388D1 (ATCC# TIB-63); endothelial cells such as HUVEC's and bovine aortic endothelial cells (BAEC's); as well as generic mammalian cell lines such as HeLa cells and COS cells, e.g., COS-7 (ATCC# CRL-1651). Further, such cells may include recombinant, transgenic cell lines. For example, the cardiovascular disease animal models of the invention, discussed, above, in Section 5.4.4.1, may be used to generate cell lines, containing one or more cell types involved in cardiovascular disease, that can be used as cell culture models for this disorder. While primary cultures derived from the cardiovascular disease transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

Alternatively, cells of a cell type known to be involved in cardiovascular disease may be transfected with sequences capable of increasing or decreasing the amount of target gene expression within the cell. For example, target gene sequences may be introduced into, and overexpressed in, the genome of the cell of interest, or, if endogenous target gene sequences are present, they may be either overexpressed or, alternatively disrupted in order to underexpress or inactivate target gene expression.

In order to overexpress a target gene sequence, the coding portion of the target gene sequence may be ligated to a regulatory sequence which is capable of driving gene expression in the cell type of interest. Such regulatory regions will be well known to those of skill in the art, and may be utilized in the absence of undue experimentation. Recombinant methods for expressing target genes are described in Section 5.4.2, above.

For underexpression of an endogenous target gene sequence, such a sequence may be isolated and engineered such that when reintroduced into the genome of the cell type of interest, the endogenous target gene alleles will be inactivated. Preferably, the engineered target gene sequence is introduced via gene targeting such that the endogenous target sequence is disrupted upon integration of the engineered target gene sequence into the cell's genome. Transfection of host cells with target genes is discussed, above, in Section 5.4.4.1.

Cells treated with compounds or transfected with target genes can be examined for phenotypes associated with cardiovascular disease. In the case of monocytes, such phenotypes include but are not limited to increases in rates of LDL uptake, adhesion to endothelial cells, transmigration, foam cell formation, fatty streak formation, and production by foam cells of growth factors such as bFGF, IGF-I, VEGF, IL-1, M-CSF, TGFβ, TGFα, TNFα, HB-EGF, PDGF, IFN-γ, and GM-CSF. Transmigration rates, for example, may be measured using the in vitro system of Navab et al., described in Section 5.1.1.3, above, by quantifying the nubber of monocytes that migrate across the endothelial monolayer and into the collagen layer of the subendothelial space.

Similarly, HUVEC's can be treated with test compounds or transfected with genetically engineered target genes described in Section 5.4.2, above. The HUVEC's can then be examined for phenotypes associated with cardiovascular disease, including, but not limited to changes in cellular morphology, cell proliferation, cell migration, and mononuclear cell adhesion; or for the effects on production of other proteins involved in cardiovascular disease such as ICAM, VCAM, PDGF-β, and E-selectin.

Transfection of target gene sequence nucleic acid may be accomplished by utilizing standard techniques. See, for example, Ausubel, 1989, supra. Transfected cells should be evaluated for the presence of the recombinant target gene sequences, for expression and accumulation of target gene mRNA, and for the presence of recombinant target gene protein production. In instances wherein a decrease in target gene expression is desired, standard techniques may be used to demonstrate whether a decrease in endogenous target gene expression and/or in target gene product production is achieved.

5.5. SCREENING ASSAYS FOR COMPOUNDS THAT INTERACT WITH THE TARGET GENE PRODUCT AND/OR MODULATE TARGET GENE EXPRESSION

The following assays are designed to identify compounds that bind to target gene products, bind to other cellular or extracellular proteins that interact with a target gene product, and interfere with the interaction of the target gene product with other cellular or extracellular proteins. Such compounds can act as the basis for amelioration of such cardiovascular diseases as atherosclerosis, ischemia/reperfusion, hypertension, restenosis, and arterial inflammation by modulating the activity of the protein products of target genes. Such compounds may also act, for example, as activators or enhancers of the TGF-b signalling response, e.g., of the TGF-β cell growth inhibitory response, for the basis for the amelioration of fibroproliferative and oncogenic related disorders, including tumorigenesis and the vascularization of tumors. Such compounds may include, but are not limited to peptides, antibodies, or small organic or inorganic compounds. Methods for the identification of such compounds are described in Section 5.5.1, below. Such compounds may also include other cellular proteins. Methods for the identification of such cellular proteins are described, below, in Section 5.5.2.

Compounds identified via assays such as those described herein may be useful, for example, in elaborating the biological function of the target gene product, and for ameliorating cardiovascular, fibroproliferative and oncogenic related disease. In instances whereby a cardiovascular disease condition results from an overall lower level of target gene expression and/or target gene product in a cell or tissue, compounds that interact with the target gene product may include compounds which accentuate or amplify the activity of the bound target gene protein. Such compounds would bring about an effective increase in the level of target gene product activity, thus ameliorating symptoms.

In some cases, a target gene observed to be up-regulated under disease conditions may be exerting a protective effect. Compounds that enhance the expression of such up-regulated genes, or the activity of their gene products, would also ameliorate disease symptoms, especially in individuals whose target gene is not normally up-regulated.

In other instances mutations within the target gene may cause aberrant types or excessive amounts of target gene proteins to be made which have a deleterious effect that leads to cardiovascular, fibroproliferative and oncogenic related disease. Similarly, physiological conditions may cause an excessive increase in target gene expression leading to cardiovascular, fibroproliferative and oncogenic related disease. In such cases, compounds that bind target gene protein may be identified that inhibit the activity of the bound target gene protein. Assays for testing the effectiveness of compounds, identified by, for example, techniques such as those described in this Section are discussed, below, in Section 5.5.4.

5.5.1. IN VITRO SCREENING ASSAYS FOR COMPOUNDS THAT BIND TO THE TARGET GENE PRODUCT

In vitro systems may be designed to identify compounds capable of binding the target gene of the invention. Such compounds may include, but are not limited to, peptides made of D-and/or L-configuration amino acids (in, for example, the form of random peptide libraries; see e.g., Lam, K. S. et al., 1991, Nature 354:82–84), phosphopeptides (in, for example, the form of random or partially degenerate, directed phosphopeptide libraries; see, e.g., Songyang, Z. et al., 1993, Cell 72:767–778), antibodies, and small organic or inorganic molecules. Compounds identified may be useful, for example, in modulating the activity of target gene proteins, preferably mutant target gene proteins, may be useful in elaborating the biological function of the target gene protein, may be utilized in screens for identifying compounds that disrupt normal target gene interactions, or may in themselves disrupt such interactions. For instance, the example in Section 12, below, describes the interaction between the rchd534 protein and the fchd540 protein. Compounds that disrupt the interaction between these two proteins may be useful in the treatment of cardiovascular disease.

The principle of the assays used to identify compounds that bind to the target gene protein involves preparing a reaction mixture of the target gene protein and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring the target gene or the test substance onto a solid phase and detecting target gene/test substance complexes anchored on the solid phase at the end of the reaction. In one embodiment of such a method, the target gene protein may be anchored onto a solid surface, and the test compound, which is not anchored, may be labeled, either directly or indirectly.

In practice, microtitre plates are conveniently utilized. The anchored component may be immobilized by non-covalent or covalent attachments. Non-covalent attachment may be accomplished simply by coating the solid surface with a solution of the protein and drying. Alternatively, an immobilized antibody, preferably a monoclonal antibody, specific for the protein may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for target gene product or the test compound to anchor any complexes formed in solution, and a labeled antibody specific for the other component of the possible complex to detect anchored complexes.

Compounds that are shown to bind to a particular target gene product through one of the methods described above can be further tested for their ability to elicit a biochemical response from the target gene protein. A particular embodiment is described herein for receptor proteins involved in signal transduction. Compounds that interact with a target gene product receptor domain, can be screened for their ability to function as ligands, i.e., to bind to the receptor protein in a manner that triggers the signal transduction pathway. Useful receptor fragments or analogs in the invention are those which interact with ligand. The receptor component can be assayed functionally, i.e., for its ability to bind ligand and mobilize $Ca^{++}$ (see below). These assays include, as components, ligand and a recombinant target gene product (or a suitable fragment or analog) configured to permit detection of binding.

For example, and not by way of limitation, a recombinant receptor may be used to screen for ligands by its ability to mediate ligand-dependent mobilization of calcium. Cells, preferably myeloma cells or Xenopus oocytes, transfected with a target gene expression vector (constructed according to the methods described in Section 5.4.2, above) are loaded with FURA-2 or INDO-1 by standard techniques. Mobilization of $Ca^{2+}$ induced by ligand is measured by fluorescence spectroscopy as previously described (Grynkiewicz et al., 1985, *J. Biol. Chem.* 260:3440). Ligands that react with the target gene product receptor domain, therefore, can be identified by their ability to produce a fluorescent signal. Their receptor binding activities can be quantified and compared by measuring the level of fluorescence produced over background. Identification of ligand, and measuring the activity of the ligand-receptor complex, leads to the identification of antagonists of this interaction, as described in Section 5.5.3, below. Such antagonists are useful in the treatment of cardiovascular disease.

5.5.2. ASSAYS FOR CELLULAR OR EXTRACELLULAR PROTEINS THAT INTERACT WITH THE TARGET GENE PRODUCT

Any method suitable for detecting protein-protein interactions may be employed for identifying novel target protein-cellular or extracellular protein interactions. These methods are outlined in Section 5.2., supra, for the identification of pathway genes, and may be utilized herein with respect to the identification of proteins which interact with identified target proteins. In such a case, the target gene serves as the known "bait" gene.

The example presented in Section 12, below, demonstrates the use of this method to detect the interaction between the rchd534 protein and the fchd540 protein, which both had been identified as target proteins.

5.5.3. ASSAYS FOR COMPOUNDS THAT INTERFERE WITH INTERACTION BETWEEN TARGET GENE PRODUCT AND OTHER COMPOUNDS

The target gene proteins of the invention may, in vivo, interact with one or more cellular or extracellular proteins. Such proteins may include, but are not limited to, those proteins identified via methods such as those described, above, in Section 5.5.2. For the purposes of this discussion, target gene products and such cellular and extracellular proteins are referred to herein as "binding partners". Compounds that disrupt such interactions may be useful in regulating the activity of the target gene proteins, especially mutant target gene proteins. Such compounds may include, but are not limited to molecules such as antibodies, peptides, and the like described in Section 5.5.1. above.

The basic principle of the assay systems used to identify compounds that interfere with the interaction between the target gene protein, and its cellular or extracellular protein binding partner or partners involves preparing a reaction mixture containing the target gene protein and the binding partner under conditions and for a time sufficient to allow the two proteins to interact and bind, thus forming a complex. In order to test a compound for inhibitory activity, the reaction mixture is prepared in the presence and absence of the test compound. The test compound may be initially included in the reaction mixture or may be added at a time subsequent to the addition of target gene and its cellular or extracellular binding partner. Control reaction mixtures are incubated without the test compound or with a placebo. The formation of any complexes between the target gene protein and the cellular or extracellular binding partner is then detected. The formation of a complex in the control reaction, but not in the reaction mixture containing the test compound, indicates that the compound interferes with the interaction of the target gene protein and the interactive binding partner protein. Additionally, complex formation within reaction mixtures containing the test compound and a normal target gene protein may also be compared to complex formation within reaction mixtures containing the test compound and mutant target gene protein. This comparison may be important in those cases wherein it is desirable to identify compounds that disrupt interactions of mutant but not normal target gene proteins.

The assay for compounds that interfere with the interaction of the binding partners can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the target gene protein and interactive cellular or extracellular protein. Alternatively, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, either the target gene protein or the interactive cellular or extracellular binding partner protein, is anchored onto a solid surface, and its binding partner, which is not anchored, is labeled, either directly or indirectly. In practice, microtitre plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the target gene protein and the interactive cellular or extracellular protein is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background. In this way, test substances which disrupt target gene protein-cellular or extracellular protein interaction can be identified.

In a particular embodiment, the target gene protein can be prepared for immobilization using recombinant DNA techniques described in Section 5.4.2, supra. For example, the target gene coding region can be fused to a glutathione-S-transferase (GST) gene, using a fusion vector such as pGEX-5X-1, in such a manner that its binding activity maintained in the resulting fusion protein. The interactive cellular or extracellular protein can be purified and used to raise a monoclonal antibody, using methods routinely practiced in the art and described above, in Section 5.4.3. This antibody can be labeled with the radioactive isotope $^{125}$I, for example, by methods routinely practiced in the art. In a heterogeneous assay, e.g., the GST-target gene fusion protein can be anchored to glutathione-agarose beads. The interactive cellular or extracellular binding partner protein can then be added in the presence or absence of the test compound in a manner that allows interaction and binding to occur. At the end of the reaction period, unbound material can be washed away, and the labeled monoclonal antibody can be added to the system and allowed to bind to the complexed binding partners. The interaction between the target gene protein and the interactive cellular or extracellular binding partner protein can be detected by measuring the amount of radioactivity that remains associated with the glutathione-agarose beads. A successful inhibition of the interaction by the test compound will result in a decrease in measured radioactivity.

Alternatively, the GST-target gene fusion protein and the interactive cellular or extracellular binding partner protein can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the target gene protein and the interactive cellular or extracellular protein, respectively, in place of one or both of the full length proteins. Any number of methods routinely practiced in the art can be used to identify and isolate the protein's binding site. These methods include, but are not limited to, mutagenesis of one of the genes encoding the proteins and screening for disruption of binding in a co-immunoprecipitation assay. Compensating mutations in the target gene can be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the for the cellular or extracellular protein is obtained, short gene segments can be engineered to express peptide fragments of the protein, which can then be tested for binding activity and purified or synthesized.

For example, and not by way of limitation, target gene can be anchored to a solid material as described above in this Section by making a GST-target gene fusion protein and allowing it to bind to glutathione agarose beads. The interactive cellular or extracellular binding partner protein can be labeled with a radioactive isotope, such as $^{35}S$, and cleaved with a proteolytic enzyme such as trypsin. Cleavage products can then be added to the anchored GST-target gene fusion protein and allowed to bind. After washing away unbound peptides, labeled bound material, representing the cellular or extracellular binding partner protein binding domain, can be eluted, purified, and analyzed for amino acid sequence by techniques well known in the art; e.g., using the Edman degradation procedure (see e.g., Creighton, 1983, Proteins: Structures and Molecular Principles, W.H. Freeman & Co., N.Y., pp. 34–49). Peptides so identified can be produced, using techniques well known in the art, either synthetically (see e.g., Creighton, 1983, supra at pp. 50–60) or, if the gene has already been isolated, by using recombinant DNA technology, as described in Section 5.4.2, supra.

A particular embodiment of the invention features a method of screening candidate compounds for their ability to antagonize the interaction between ligand and the receptor domain of a target gene product. The method involves: a) mixing a candidate antagonist compound with a first compound which includes a recombinant target gene product comprising a receptor domain (or ligand-binding fragment or analog) on the one hand and with a second compound which includes ligand on the other hand; b) determining whether the first and second compounds bind; and c) identifying antagonistic compounds as those which interfere with the binding of the first compound to the second compound and/or which reduce the ligand-mediated release of intracellular $Ca^{++}$.

By an "antagonist" is meant a molecule which inhibits a particular activity, in this case, the ability of ligand to interact with a target gene product receptor domain and/or to trigger the biological events resulting from such an interaction (e.g., release of intracellular $Ca^{++}$). Preferred therapeutics include antagonists, e.g., peptide fragments (particularly, fragments derived from the N-terminal extracellular domain), antibodies (particularly, antibodies which recognize and bind the N-terminal extracellular domain), or drugs, which block ligand or target gene product function by interfering with the ligand-receptor interaction.

Because the receptor component of the target gene product can be produced by recombinant techniques and because candidate antagonists may be screened in vitro, the instant invention provides a simple and rapid approach to the identification of useful therapeutics.

Specific receptor fragments of interest include any portions of the target gene products that are capable of interaction with ligand, for example, all or part of the N-terminal extracellular domain. Such portions include the transmembrane segments and portions of the receptor deduced to be extracellular. Such fragments may be useful as antagonists (as described above), and are also useful as immunogens for producing antibodies which neutralize the activity of the target gene product in vivo (e.g., by interfering with the interaction between the receptor and ligand; see below). Extracellular regions may be identified by comparison with related proteins of similar structure, useful regions are those exhibiting homology to the extracellular domains of well-characterized members of the family.

Alternatively, from the primary amino acid sequence, the secondary protein structure and, therefore, the extracellular domain regions may be deduced semi-empirically using a hydrophobicity/hydrophilicity calculation such as the Chou-Fasman method (see, e.g., Chou and Fasman, *Ann. Rev. Biochem.* 47:251, 1978). Hydrophilic domains, particularly ones surrounded by hydrophobic stretches (e.g., transmembrane domains) present themselves as strong candidates for extracellular domains. Finally, extracellular domains may be identified experimentally using standard enzymatic digest analysis, e.g., tryptic digest analysis.

Candidate fragments (e.g., all or part of the transmembrane segments or any extracellular fragment) are tested for interaction with ligand by the assays described herein (e.g., the assay described above). Such fragments are also tested for their ability to antagonize the interaction between ligand and its endogenous receptor using the assays described herein. Analogs of useful receptor fragments (as described above) may also be produced and tested for efficacy as screening components or antagonists (using the assays described herein); such analogs are also considered to be useful in the invention.

Of particular interest are receptor fragments encompassing the extracellular main-terminal domain (or a ligand binding fragment thereof). Also of interest are the target gene product extracellular loops. Peptide fragments derived from these extracellular loops may also be used as antagonists, particularly if the loops cooperate with the amino-terminal domain to facilitate ligand binding. Alternatively, such loops and extracellular N-terminal domain (as well as the full length target gene product) provide immunogens for producing anti-target gene product antibodies.

Binding of ligand to its receptor may be assayed by any of the methods described above in Section 5.5.1. Preferably, cells expressing recombinant target gene product (or a suitable target gene product fragment or analog) are immobilized on a solid substrate (e.g., the wall of a microtitre plate or a column) and reacted with detectably-labelled ligand (as described above). Binding is assayed by the detection label in association with the receptor component (and, therefore, in association with the solid substrate). Binding of labelled ligand to receptor-bearing cells is used as a "control" against which antagonist assays are measured. The antagonist assays involve incubation of the target gene product-bearing cells with an appropriate amount of candidate antagonist. To this mix, an equivalent amount to labelled ligand is added. An antagonist useful in the invention specifically interferes with labelled ligand binding to the immobilized receptor-expressing cells.

An antagonist is then tested for its ability to interfere with ligand function, i.e., to specifically interfere with labelled ligand binding without resulting in signal transduction normally mediated by the receptor. To test this using a functional assay, stably transfected cell lines containing the target gene product can be produced as described herein and reporter compounds such as the calcium binding agent, FURA-2, loaded into the cytoplasm by standard techniques. Stimulation of the heterologous target gene product with ligand or another agonist leads to intracellular calcium release and the concomitant fluorescence of the calcium-FURA-2 complex. This provides a convenient means for measuring agonist activity. Inclusion of potential antagonists along with ligand allows for the screening and identification of authentic receptor antagonists as those which effectively block ligand binding without producing fluorescence (i.e., without causing the mobilization of intracellular $Ca^{++}$). Such an antagonist may be expected to be a useful therapeutic agent for cardiovascular disorders.

Appropriate candidate antagonists include target gene product fragments, particularly fragments containing a ligand-binding portion adjacent to or including one or more transmembrane segments or an extracellular domain of the receptor (described above); such fragments would preferably including five or more amino acids. Other candidate antagonists include analogs of ligand and other peptides as well as non-peptide compounds and anti-target gene product antibodies designed or derived from analysis of the receptor.

In one embodiment, candidate compounds can be screened for their ability to antagonize the interaction between a target gene product which is a member of the TGF-b signaling pathway and a second member of said pathway. The method involves: a) contacting a candidate antagonist compound with a first compound comprising at least that portion of a target gene product involved in binding to a second compound, and at least that portion of the second compound which is involved in binding to the target gene product; b) determining whether the first and second compounds bind in the presence of the test compound; and c) identifying antagonistic compounds as those which interfere with the binding of the first compound to the second compound relative to the binding observed in the absence of test compound and/or which activate or enchance the TGF-$\beta$ response.

One such target gene product which can be utilized as part of such an embodiment is the fchd540 target gene product. Alternatively, for example, the rchd534 target gene product can be utilized. Second TGF-$\beta$ signalling related compounds can include, for example, fchd540, rchd534 and activated T$\beta$1R.

Binding of ligand to its receptor may be assayed by any of the methods described above in Section 5.5.1. Preferably, downstream signaling events may be monitored as a readout for assay results. For example, many signaling proteins phosphorylate substrate proteins that are "downstream" in a signaling pathway. The phosphorylation state of a substrate protein could therefore be examined in an assay to determine the activity of a signaling pathway, such as the TGF-$\beta$ pathway. Because the receptor component of the target gene product can be produced by recombinant techniques and because candidate antagonists may be screened, for example, in vitro, the instant invention provides a simple and rapid approach to the identification of useful therapeutics.

5.5.3. ASSAYS FOR AMELIORATION OF CARDIOVASCULAR AND CELL PROLIFERATIVE DISEASE SYMPTOMS

Any of the binding compounds, including but not limited to compounds such as those identified in the foregoing assay systems, may be tested for the ability to ameliorate cardiovascular disease symptoms. Cell-based and animal model-based assays for the identification of compounds exhibiting such an ability to ameliorate cardiovascular disease symptoms are described below.

First, cell-based systems such as those described, above, in Section 5.4.4.2., may be used to identify compounds which may act to ameliorate cardiovascular disease symptoms. For example, such cell systems may be exposed to a compound, suspected of exhibiting an ability to ameliorate cardiovascular disease symptoms, at a sufficient concentration and for a time sufficient to elicit such an amelioration of cardiovascular disease symptoms in the exposed cells. After exposure, the cells are examined to determine whether one or more of the cardiovascular disease cellular phenotypes has been altered to resemble a more normal or more wild type, non-cardiovascular disease phenotype. For example, and not by way of limitation, in the case of monocytes, such more normal phenotypes may include but are not limited to decreased rates of LDL uptake, adhesion to endothelial cells, transmigration, foam cell formation, fatty streak formation, and production by foam cells of growth factors such as bFGF, IGF-I, VEGF, IL-1, M-CSF, TGF$\beta$, TGF$\alpha$, TNF$\alpha$, HB-EGF, PDGF, IFN-$\gamma$, and GM-CSF. Transmigration rates, for example, may be measured using the in vitro system of Navab et al., described in Section 5.1.1.3, above, by quantifying the number of monocytes that migrate across the endothelial monolayer and into the collagen layer of the subendothelial space.

In addition, animal-based cardiovascular disease systems, such as those described, above, in Section 5.4.4.1, may be used to identify compounds capable of ameliorating cardiovascular disease symptoms. Such animal models may be used as test substrates for the identification of drugs, pharmaceuticals, therapies, and interventions which may be effective in treating cardiovascular disease. For example, animal models may be exposed to a compound, suspected of exhibiting an ability to ameliorate cardiovascular disease symptoms, at a sufficient concentration and for a time sufficient to elicit such an amelioration of cardiovascular disease symptoms in the exposed animals. The response of the animals to the exposure may be monitored by assessing the reversal of disorders associated with cardiovascular disease, for example, by counting the number of atherosclerotic plaques and/or measuring their size before and after treatment.

Further, both cell-based systems and animal-based systems as described herein may be used to identify compounds which act to ameliorate symptoms of fibroproliferative and oncogenic related disorders, including tumorigenesis and the vascularization of tumors. Such cell-based and animal-based systems may be exposed to a compound, suspected of exhibiting an ability to ameliorate TGF-$\beta$ associated fibroproliferative or oncogenic disease symptoms, at a sufficient concentration and for a time sufficient to elicit such an amelioration of fibroproliferative disease symptoms in the exposed system. The response may be monitored by assessing the reversal of disorders associated with fibroproliferative disease, for example by measuring the size and growth of tumors or vascularization of tumors before and after treatment.

With regard to intervention, any treatments which reverse any aspect of cardiovascular, fibroproliferative and oncogenic related disease symptoms should be considered as candidates for human cardiovascular, fibroproliferative and oncogenic related disease therapeutic intervention. Dosages of test agents may be determined by deriving dose-response curves, as discussed in Section 5.7.1, below.

Additionally, gene expression patterns may be utilized to assess the ability of a compound to ameliorate cardiovascular disease symptoms. For example, the expression pattern of one or more fingerprint genes may form part of a "fingerprint profile" which may be then be used in such an assessment. "Fingerprint profile", as used herein, refers to the pattern of mRNA expression obtained for a given tissue or cell type under a given set of conditions. Such conditions may include, but are not limited to, atherosclerosis, ischemia/reperfusion, hypertension, restenosis, and arterial inflammation, including any of the control or experimental conditions described in the paradigms of Section 5.1.1, above. Fingerprint profiles may be generated, for example, by utilizing a differential display procedure, as discussed, above, in Section 5.1.2, Northern analysis and/or RT-PCR. Any of the gene sequences described, above, in Section 5.4.1. may be used as probes and/or PCR primers for the generation and corroboration of such fingerprint profiles.

Fingerprint profiles may be characterized for known states, either cardiovascular disease or normal, within the cell- and/or animal-based model systems. Subsequently, these known fingerprint profiles may be compared to ascertain the effect a test compound has to modify such fingerprint profiles, and to cause the profile to more closely resemble that of a more desirable fingerprint.

For example, administration of a compound may cause the fingerprint profile of a cardiovascular disease model system to more closely resemble the control system. Administration of a compound may, alternatively, cause the fingerprint profile of a control system to begin to mimic a cardiovascular disease state. Such a compound may, for example, be used in further characterizing the compound of interest, or may be used in the generation of additional animal models.

5.5.4. MONITORING OF EFFECTS DURING CLINICAL TRIALS

Monitoring the influence of compounds on cardiovascular, fibroproliferative and oncogenic related disease states may be applied not only in basic drug screening, but also in clinical trials. In such clinical trials, the expression of a panel of genes that have been discovered in one of the paradigms described in Section 5.1.1.1 through 5.1.1.6 may be used as a "read out" of a particular drug's effect on a cardiovascular, fibroproliferative oncogenic related disease state.

For example, and not by way of limitation, Paradigm A provides for the identification of fingerprint genes that are up-regulated in monocytes treated with oxidized LDL. Thus, to study the effect of anti-oxidant drugs, for example, in a clinical trial, blood may be drawn from patients before and at different stages during treatment with such a drug. Their monocytes may then be isolated and RNA prepared and analyzed by differential display as described in Sections 6.1.1 and 6.1.2. The levels of expression of these fingerprint genes may be quantified by Northern blot analysis or RT-PCR, as described in Section 6.1.2, or by one of the methods described in Section 5.8.1, or alternatively by measuring the amount of protein produced, by one of the methods described in Section 5.8.2. In this way, the fingerprint profiles may serve as surrogate markers indicative of the physiological response of monocytes that have taken up oxidized LDL. Accordingly, this response state may be determined before, and at various points during, drug treatment. This method is described in further detail in the example in Section 8, below. Specifically, the up-regulation of fchd602 and fchd605 under treatment with oxidized LDL provides a fingerprint profile for monocytes under oxidative stress. The fchd602 and fchd605 genes can serve, therefore, as surrogate markers during clinical treatment of cardiovascular disease. Accordingly, the influence of anti-oxidant drugs on oxidative potential is measured by recording the differential display of fchd602 and fchd605 in the monocytes of patients undergoing clinical treatment.

Likewise, the expression of fchd540 and/or rchd534 can be utilized as surrogate markers during clinical treatment of fibroproliferative and oncogenic related disorders. In this instance, a lowering of expression from these genes would be sought.

5.5.5. ASSAYS FOR COMPOUNDS THAT MODULATE EXPRESSION OF TARGET GENES

Compounds and other substances that modulate expression of target genes can be screened using in vitro cellular systems. In a manner analogous to the monitoring of compounds clinical samples described in Section 5.5.5, above, a sample of cells, such as a tissue culture is exposed to a test substance. Appropriate tissue culture cells include, but are not limited to, human umbilical vein endothelial cells (HUVECs), bovine aortic endothelial cells (BAECs), and 293 cells (embryonic human kidney cells). The RNA is then extracted from the cells. The level of transcription of a specific target gene can be detected using, for example, standard RT-PCR amplification techniques and/or Northern analysis (as described in the example in Section 6.1.2, below). Alternatively, the level of target protein production can be assayed by using antibodies that detect the target gene protein, as described in Section 5.5.1, above. The level of expression is compared to a control cell sample which was not exposed to the test substance.

Compounds that can be screened for modulation of expression of the target gene include, but are not limited to, small inorganic or organic molecules, peptides, such as peptide hormones analogs, steroid hormones, analogs of such hormones, and other proteins. Compounds that downregulate expression include, but are not limited to, oligonucleotides that are complementary to the 5'-end of the mRNA of the target gene and inhibit transcription by forming triple helix structures, and ribozymes or antisense molecules which inhibit translation of the target gene mRNA. Techniques and strategies for designing such down-regulating test compounds are described in detail in Section 5.6, below.

5.6. COMPOUNDS AND METHODS FOR ACTIVATION OF TGF-B INHIBITORY RESPONSE AND TREATMENT OF CARDIOVASCULAR AND FIBROPROLIFERATIVE DISEASE

Described below are methods and compositions whereby TGF-β modulated fibroproliferative and oncogenic disease symptoms may be ameliorated by compounds that activate or enchance the TGF-β response, and whereby cardiovascular disease symptoms may be ameliorated. In certain instances, fibroproliferative and oncogenic disease associated with aberrant TGF-β signaling, or instances of cardiovascular disease, are brought about, at least in part, by an excessive level of gene product, or by the presence of a gene product exhibiting an abnormal or excessive activity. As such, the reduction in the level and/or activity of such gene products would bring about the activation or enhancement of the TFG-b response and, therefore, amelioration of disease symptoms. Techniques for the reduction of target gene expression levels or target gene product activity levels are discussed in Section 5.6.1, below.

Alternatively, certain other fibroproliferative and onco-genic disease associated with abarrent TGF-b signaling, or instances of cardiovascular disease, are brought about, at least in part, by the absence or reduction of the level of gene expression, or a reduction in the level of a gene product's activity. As such, an increase in the level of gene expression and/or the activity of such gene products would bring about the amelioration of cardiovascular disease symptoms.

In some cases, the up-regulation of a gene in a disease state reflects a protective role for that gene product in responding to the disease condition. Enhancement of such a target gene's expression, or the activity of the target gene product, will reinforce the protective effect it exerts. Fibro-proliferative and oncogenic disease associated with aberrant TGF-β signaling, or instances of cardiovascular disease, states may result from an abnormally low level of activity of such a protective gene. In these cases also, an increase in the level of gene expression and/or the activity of such gene products would bring about the amelioration of cardiovascular disease symptoms. Techniques for increasing target gene expression levels or target gene product activity levels are discussed in Section 5.6.2, below.

With respect to specific fibroproliferative and oncogenic disease associated with aberrant TGF-β signaling, the diseases that can be treated or prevented by the methods of the present invention include but are not limited to: human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

5.6.1. COMPOUNDS THAT INHIBIT EXPRESSION, SYNTHESIS OR ACTIVITY OF MUTANT TARGET GENE ACTIVITY

As discussed above, target genes involved in cardiovascular disease disorders can cause such disorders via an increased level of target gene activity. As summarized in Table 1, above, and detailed in the examples in Sections 6 and 7, below, a number of genes have been demonstrated to be up-regulated in monocytes and endothelial cells under disease conditions. Specifically, fchd602 and fchd605 are each up-regulated in monocytes treated with oxidized LDL. Furthermore, fchd540 is up-regulated in endothelial cells subjected to shear stress and in some cancer cells. In some cases, such up-regulation may have a causative or exacerbating effect on the disease state. A variety of techniques may be utilized to inhibit the expression, synthesis, or activity of such target genes and/or proteins.

For example, compounds such as those identified through assays described, above, in Section 5.5, which exhibit inhibitory activity, may be used in accordance with the invention to ameliorate cardiovascular disease symptoms. As discussed in Section 5.5, above, such molecules may include, but are not limited to small organic molecules, peptides, antibodies, and the like. Inhibitory antibody techniques are described, below, in Section 5.6.1.2.

For example, compounds can be administered that compete with endogenous ligand for a transmembrane target gene product. The resulting reduction in the amount of ligand-bound target gene transmembrane protein will modulate cell physiology. Compounds that can be particularly useful for this purpose include, for example, soluble proteins or peptides, such as peptides comprising one or more of the extracellular domains, or portions and/or analogs thereof, of the target gene product, including, for example, soluble fusion proteins such as Ig-tailed fusion proteins. (For a discussion of the production of Ig-tailed fusion proteins, see, for example, U.S. Pat. No. 5,116,964.). Alternatively, compounds, such as ligand analogs or antibodies, that bind to the target gene product receptor site, but do not activate the protein, (e.g., receptor-ligand antagonists) can be effective in inhibiting target gene product activity.

Further, antisense and ribozyme molecules which inhibit expression of the target gene may also be used in accordance with the invention to inhibit the aberrant target gene activity. Such techniques are described, below, in Section 5.6.1.1. Still further, also as described, below, in Section 5.6.1.1, triple helix molecules may be utilized in inhibiting the aberrant target gene activity.

5.6.1.1. INHIBITORY ANTISENSE, RIBOZYME, TRIPLE HELIX, AND GENE INACTIVATION APPROACHES

Among the compounds which may exhibit the ability to ameliorate cardiovascular disease symptoms are antisense, ribozyme, and triple helix molecules. Such molecules may be designed to reduce or inhibit mutant target gene activity. Techniques for the production and use of such molecules are well known to those of skill in the art.

Antisense RNA and DNA molecules act to directly block the translation of mRNA by hybridizing to targeted mRNA and preventing protein translation.

Antisense approaches involve the design of oligonucleotides (either DNA or RNA) that are complementary to target gene mRNA. The antisense oligonucleotides will bind to the complementary target gene mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'- non-translated, non-coding regions of the target gene could be used in an antisense approach to inhibit translation of endogenous target gene mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of target gene mRNA, antisense nucleic acids should be at least six nucleotides in length, and are preferably oligonucleotides ranging from 6 to about 50 nucleotides in length.

In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the target gene coding region sequence could be used, those complementary to the transcribed untranslated region are most preferred.

Specific antisense oligonucleotides for the rchd534 gene and fchd540 gene are described in the Example in Section 13, below.

The antisense molecules should be delivered to cells which express the target gene in vivo, e.g., endothelial cells. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A.

78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site; e.g., atherosclerotic vascular tissue. Alternatively, viral vectors can be used which selectively infect the desired tissue, in which case administration may be accomplished by another route (e.g., systemically).

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. Ribozyme molecules designed to catalytically cleave target gene mRNA transcripts can also be used to prevent translation of target gene mRNA and expression of target gene. (See, e.g., PCT International Publication WO90/11364, published Oct. 4, 1990; Sarver et al., 1990, Science 247:1222–1225). While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. For example, there are hundreds of potential hammerhead ribozyme cleavage sites within the nucleotide sequence of rchd534 and fchd540 cDNA. Preferably the ribozyme is engineered so that the cleavage recognition site is located near the 5' end of the target mRNA; i.e., to increase efficiency and minimize the intracellular accumulation of non-functional mRNA transcripts.

Specific hammerhead ribozymes molecules for the rchd534 and fchd540 genes are described in the Example in Section 13, below.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in target gene.

As in the antisense approach, the ribozymes can be composed of modified oligonucleotides (e.g. for improved stability, targeting, etc.) and should be delivered to cells which express the target gene in vivo, e.g., endothelial cells. A preferred method of delivery involves using a DNA construct "encoding" the ribozyme under the control of a strong constitutive pol III or pol II promoter, so that transfected cells will produce sufficient quantities of the ribozyme to destroy endogenous taraet gene messages and inhibit translation. Because ribozymes, unlike antisense molecules, are catalytic, a lower intracellular concentration is required for efficiency.

Nucleic acid molecules to be used in triple helix formation for the inhibition of transcription should be single stranded and composed of deoxyribonucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC paris, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

It is possible that the antisense, ribozyme, and/or triple helix molecules described herein may reduce or inhibit the transcription (triple helix) and/or translation (antisense, ribozyme) of mRNA produced by both normal and mutant target gene alleles. In order to ensure that substantially normal levels of target gene activity are maintained, nucleic acid molecules that encode and express target gene polypeptides exhibiting normal activity may be introduced into cells via gene therapy methods such as those described, below, in Section 5.7. that do not contain sequences susceptible to whatever antisense, ribozyme, or triple helix treatments are being utilized. Alternatively, it may be preferable to coadminister normal target gene protein into the cell or tissue in order to maintain the requisite level of cellular or tissue target gene activity.

Endogenous target gene expression can also be reduced by inactivating or "knocking out" the target gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional target (or a completely unrelated DNA sequence) flanked by DNA homologous to the endogenous target gene (either the coding regions or regulatory regions of the target gene) can be used, with or without a selectable marker and/or a negative selectable marker, to transfect cells that express target in vivo. Insertion of the DNA construct, via targeted homologous recombination, results in inactivation of the target gene. Such approaches can be adapted for use in humans provided the recombinant DNA constructs are directly administered or targeted to the required site in vivo using appropriate viral vectors, e.g., vectors for delivery vascular tissue.

Alternatively, endogenous target gene expression can be reduced by targeting deoxyribonucleotide sequences complementary to the regulatory region of the target gene (i.e., the target promoter and/or enhancers) to form triple helical structures that prevent transcription of the target gene in target cells in the body. (See generally, Helene, C. 1991, Anticancer Drug Des., 6(6):569–84; Helene, C., et al., 1992, Ann, N.Y. Acad. Sci., 660:27–36; and Maher, L. J., 1992, Bioassays 14(12):807–15).

In yet another embodiment of the invention, the activity of a target can be reduced using a "dominant negative" approach to effectuate reduction in cardiovascular disease symptoms. For example, if two gene products interact, such as the rchd534 and fchd540 proteins, then the presence of a mutant version of one or both of these proteins in the cell can reduce the overall pool of complexes consisting of entirely wild-type proteins. In this manner, the overall level of activity resulting from the rchd534/fchd540 protein interaction can be reduced.

5.6.1.2. ANTIBODIES FOR TARGET GENE PRODUCTS

Antibodies that are both specific for target gene protein and interfere with its activity may be used to inhibit target gene function. Such antibodies may be generated using standard techniques described in Section 5.4.3., supra, against the proteins themselves or against peptides corresponding to portions of the proteins. Such antibodies include but are not limited to polyclonal, monoclonal, Fab fragments, single chain antibodies, chimeric antibodies, etc.

In instances where the target gene protein is intracellular and whole antibodies are used, internalizing antibodies may be preferred. However, lipofectin liposomes may be used to deliver the antibody or a fragment of the Fab region which binds to the target gene epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (e.g., see Creighton, 1983, supra; and Sambrook et al., 1989, supra). Alternatively, single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. USA 90:7889–7893).

In some instances, the target gene protein is extracellular, or is a transmembrane protein, such as the fchd545 and fchd602 gene products. Antibodies that are specific for one or more extracellular domains of these gene products, for example, and that interfere with its activity, are particularly useful in treating cardiovascular disease. Such antibodies are especially efficient because they can access the target domains directly from the bloodstream. Any of the administration techniques described, below in Section 5.7 which are appropriate for peptide administration may be utilized to effectively administer inhibitory target gene antibodies to their site of action.

5.6.2. METHODS FOR RESTORING OR ENHANCING TARGET GENE ACTIVITY

Target genes that cause cardiovascular disease may be underexpressed within cardiovascular disease situations. As summarized in Table 1, above, and detailed in the example in Section 7, below, several genes are now known to be down-regulated in endothelial cells under disease conditions. Specifically, fchd531 and fchd545 are down-regulated in endothelial cells subjected to shear stress. Alternatively, the activity of target gene products may be decreased, leading to the development of cardiovascular disease symptoms. Such down-regulation of target gene expression or decrease of target gene product activity might have a causative or exacerbating effect on the disease state.

In some cases, target genes that are up-regulated in the disease state might be exerting a protective effect. As summarized in Table 1, above, and detailed in the examples in Sections 6 and 7, below, a number of genes are now known to be up-regulated in monocytes and endothelial cells under disease conditions. Specifically, fchd602 and fchd605 are each up-regulated in monocytes treated with oxidized LDL. Furthermore, fchd540 is up-regulated in endothelial cells subjected to shear stress. A variety of techniques may be utilized to increase the expression, synthesis, or activity of such target genes and/or proteins, for those genes that exert a protective effect in response to disease conditions.

Described in this Section are methods whereby the level of target gene activity may be increased to levels wherein cardiovascular disease symptoms are ameliorated. The level of gene activity may be increased, for example, by either increasing the level of target gene product present or by increasing the level of active target gene product which is present.

For example, a target gene protein, at a level sufficient to ameliorate cardiovascular disease symptoms may be administered to a patient exhibiting such symptoms. Any of the techniques discussed, below, in Section 5.7, may be utilized for such administration. One of skill in the art will readily know how to determine the concentration of effective, non-toxic doses of the normal target gene protein, utilizing techniques such as those described, below, in Section 5.7.1.

Additionally, RNA sequences encoding target gene protein may be directly administered to a patient exhibiting cardiovascular disease symptoms, at a concentration sufficient to produce a level of target gene protein such that cardiovascular disease symptoms are ameliorated. Any of the techniques discussed, below, in Section 5.7, which achieve intracellular administration of compounds, such as, for example, liposome administration, may be utilized for the administration of such RNA molecules. The RNA molecules may be produced, for example, by recombinant techniques such as those described, above, in Section 5.4.2.

Further, patients may be treated by gene replacement therapy. One or more copies of a normal target gene, or a portion of the gene that directs the production of a normal target gene protein with target gene function, may be inserted into cells using vectors which include, but are not limited to adenovirus, adeno-associated virus, and retrovirus vectors, in addition to other particles that introduce DNA into cells, such as liposomes. Additionally, techniques such as those described above may be utilized for the introduction of normal target gene sequences into human cells.

Cells, preferably, autologous cells, containing normal target gene expressing gene sequences may then be introduced or reintroduced into the patient at positions which allow for the amelioration of cardiovascular disease symptoms. Such cell replacement techniques may be preferred, for example, when the target gene product is a secreted, extracellular gene product.

5.7. PHARMACEUTICAL PREPARATIONS AND METHODS OF ADMINISTRATION

The identified compounds that inhibit target gene expression, synthesis and/or activity can be administered to a patient at therapeutically effective doses to treat or ameliorate cardiovascular disease. A therapeutically effective dose refers to that amount of the compound sufficient to result in amelioration of symptoms of cardiovascular disease.

5.7.1. EFFECTIVE DOSE

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially efrom cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.7.2. FORMULATIONS AND USE

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the fcrm of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.8. DIAGNOSIS OF CARDIOVASCULAR AND FIBROPROLIFERATIVE DISEASE ABNORMALITIES

A variety of methods may be employed, utilizing reagents such as fingerprint gene nucleotide sequences described in Section 5.4.1, and antibodies directed against differentially expressed and pathway gene peptides, as described, above in Sections 5.4.2. (peptides) and 5.4.3. (antibodies). Specifically, such reagents may be used, for example, for the detection of the presence of target gene mutations, or the detection of either over or under expression of target gene mRNA.

The methods described herein may be performed, for example, by utilizing pre-packaged diagnostic kits comprising at least one specific fingerprint gene nucleic acid or anti-fingerprint gene antibody reagent described herein, which may be conveniently used, e.g., in clinical settings, to diagnose patients exhibiting cardiovascular disease symptoms or at risk for developing cardiovascular disease.

Any cell type or tissue, preferably monocytes, endothelial cells, or smooth muscle cells, in which the fingerprint gene is expressed may be utilized in the diagnostics described below.

5.8.1. DETECTION OF FINGERPRINT GENE NUCLEIC ACIDS

DNA or RNA from the cell type or tissue to be analyzed may easily be isolated using procedures which are well known to those in the art. Diagnostic procedures may also be performed "in situ" directly upon tissue sections (fixed and/or frozen) of patient tissue obtained from biopsies or resections, such that no nucleic acid purification is necessary. Nucleic acid reagents such as those described in Section 5.1. may be used as probes and/or primers for such in situ procedures (see, for example, Nuovo, G. J., 1992, PCR in situ hybridization: protocols and applications, Raven Press, N.Y.).

Fingerprint gene nucleotide sequences, either RNA or DNA, may, for example, be used in hybridization or amplification assays of biological samples to detect cardiovascular disease-related gene structures and expression. Such assays may include, but are not limited to, Southern or Northern analyses, single stranded conformational polymorphism analyses, in situ hybridization assays, and polymerase chain reaction analyses. Such analyses may reveal both quantitative aspects of the expression pattern of the fingerprint gene, and qualitative aspects of the fingerprint gene expression and/or gene composition. That is, such aspects may include, for example, point mutations, insertions, deletions, chromosomal rearrangements, and/or activation or inactivation of gene expression.

Preferred diagnostic methods for the detection of fingerprint gene-specific nucleic acid molecules may involve for example, contacting and incubating nucleic acids, derived from the cell type or tissue being analyzed, with one or more labeled nucleic acid reagents as are described in Section 5.1, under conditions favorable for the specific annealing of these reagents to their complementary sequences within the nucleic acid molecule of interest. Preferably, the lengths of these nucleic acid reagents are at least 9 to 30 nucleotides. After incubation, all non-annealed nucleic acids are removed from the nucleic acid:fingerprint molecule hybrid. The presence of nucleic acids from the fingerprint tissue which have hybridized, if any such molecules exist, is then detected. Using such a detection scheme, the nucleic acid from the tissue or cell type of interest may be immobilized, for example, to a solid support such as a membrane, or a plastic surface such as that on a microtitre plate or polystyrene beads. In this case, after incubation, non-annealed, labeled fingerprint nucleic acid reagents of the type described in Section 5.1. are easily removed. Detection of the remaining, annealed, labeled nucleic acid reagents is accomplished using standard techniques well-known to those in the art.

Alternative diagnostic methods for the detection of fingerprint gene specific nucleic acid molecules may involve their amplification, e.g., by PCR (the experimental embodiment set forth in Mullis, K. B., 1987, U.S. Pat. No. 4,683, 202), ligase chain reaction (Barany, F., 1991, Proc. Natl. Acad. Sci. USA 88:189–193), self sustained sequence replication (Guatelli, J. C. et al., 1990, Proc. Natl. Acad. Sci. USA 87:1874–1878), transcriptional amplification system (Kwoh, D. Y et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA may be isolated include any tissue in which wild type fingerprint gene is known to be expressed, including, but not limited, to monocytes, endothelium, and/or smooth muscle. A fingerprint sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the fingerprint gene nucleic acid reagents described in Section 5.1. The preferred lengths of such nucleic acid reagents are at least 15–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

With respect to mutations or polymorphisms in gene structure, the methods described below can be used in addition to, or in cunjuction with those those discussed above. In this context, mutations or polymorphisms within any of target genes of the invention, e.g., fchd540 or a related gene, can be detected by utilizing a number of techniques. Nucleic acid from any nucleated cell can be used as the starting point for such assay techniques, and may be isolated according to standard nucleic acid preparation procedures which are well known to those of skill in the art.

Genomic DNA may be used in hybridization or amplification assays of biological samples to detect abnormalities involving a target gene structure including point mutations, insertions, deletions and chromosomal rearrangements. Such assays may include, but are not limited to, Southern analyses, single stranded conformation polymorphism analyses (SSCP), and PCR analyses.

Further, well-known genotyping techniques can be performed to type polymorphisms that are in close proximity to mutations in the target gene itself, including mutations associated with fibroproliferative, oncogenic or cardiovascular disorders. Such polymorphisms can be used to identify individuals of a population likely to carry mutations in the target gene e.g., fchd540 or a related gene. If a polymorphism exhibits linkage disequilibrium with mutations in the target gene e.g., fchd540, the polymorphism can also be used to identify individuals in the general population who are likely to carry such mutations. Polymorphisms that can be used in this way include restriction fragment length polymorphisms (RFLPs), which involve sequence variations in restriction enzyme target sequences, single-base polymorphisms, and simple sequence length polymorphisms (SSLPs).

For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the fchd540 or a related gene, and the diagnosis of diseases and disorders related to mutations in the target gene.

Also, Caskey et al. (U.S. Pat. No. 5,364,759) describe a DNA profiling assay for detecting short tri and tetra nucleotide repeat sequences. The process includes extracting the DNA of interest, such as the target gene, e.g., fchd540 or a related gene, amplifying the extracted DNA, and labelling the repeat sequences to form a genotypic map of the individual's DNA.

A target gene, e.g., fchd540 or a related probe could additionally be used to directly identify RFLPS. Further, a target gene or a related probe or primers derived from the target gene sequence could be used to isolate genomic clones such as YACs, BACs, PACs, cosmids, phage, or plasmids. The DNA contained in these clones can be screened for single-base polymorphisms or SSLPs using standard hybridization or sequencing procedures.

Further, transgenic animals developed from of the invention include animals that express a mutant variant or polymorphism of a target gene, e.g., fchd540 or a related gene, particularly a mutant variant or polymorphism of a fchd540 or a related gene that is associated with fibroproliferative, oncogenic or cardiovascular disorders is of use in diagnosis and treament of such diseases.

In addition to methods which focus primarily on the detection of one nucleic acid sequence, fingerprint profiles, as discussed in Section 5.5.4, may also be assessed in such detection schemes. Fingerprint profiles may be generated, for example, by utilizing a differential display procedure, as discussed, above, in Section 5.1.2, Northern analysis and/or RT-PCR. Any of the gene sequences described, above, in Section 5.4.1. may be used as probes and/or PCR primers for the generation and corroboration of such fingerprint profiles.

5.8.2. DETECTION OF FINGERPRINT GENE PEPTIDES

Antibodies directed against wild type or mutant fingerprint gene peptides, which are discussed, above, in Section 5.4.3, may also be used as cardiovascular disease diagnostics and prognostics, as described, for example, herein. Such diagnostic methods, may be used to detect abnormalities in the level of fingerprint gene protein expression, or abnormalities in the structure and/or tissue, cellular, or subcellular location of fingerprint gene protein. Structural differences may include, for example, differences in the size, electronegativity, or antigenicity of the mutant fingerprint gene protein relative to the normal fingerprint gene protein.

Protein from the tissue or cell type to be analyzed may easily be detected or isolated using techniques which are well known to those of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

Preferred diagnostic methods for the detection of wild type or mutant fingerprint gene peptide molecules may involve, for example, immunoassays wherein fingerprint gene peptides are detected by their interaction with an anti-fingerprint gene specific peptide antibody.

For example, antibodies, or fragments of antibodies, such as those described, above, in Section 5.4.3, useful in the present invention may be used to quantitatively or qualitatively detect the presence of wild type or mutant fingerprint gene peptides. This can be accomplished, for example, by immunofluorescence techniques employing a fluorescently labeled antibody (see below) coupled with light microscopic, flow cytometric, or fluorimetric detection. Such techniques are especially preferred if the fingerprint gene peptides are expressed on the cell surface.

The antibodies (or fragments thereof) useful in the present invention may, additionally, be employed histologically, as in immunofluorescence or immunoelectron microscopy, for in situ detection of fingerprint gene peptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified in order to achieve such in situ detection.

Immunoassays for wild type or mutant fingerprint gene peptides typically comprise incubating a biological sample, such as a biological fluid, a tissue extract, freshly harvested cells, or cells which have been incubated in tissue culture, in the presence of a detectably labeled antibody capable of identifying fingerprint gene peptides, and detecting the bound antibody by any of a number of techniques well known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled fingerprint gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or mutant fingerprint gene peptide antibody may be determined according to well known methods. Those skilled in the art will be able to determine operative and optimal assay conditions for each determination by employing routine experimentation.

One of the ways in which the fingerprint gene peptide-specific antibody can be detectably labeled is by linking the same to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.8.3. IMAGING CARDIOVASCULAR DISEASE CONDITIONS

In some cases, differentially expressed gene products identified herein may be up-regulated under cardiovascular disease conditions and expressed on the surface of the affected tissue. Such target gene products allow for the non-invasive imaging of damaged or diseased cardiovascular tissue for the purposed of diagnosis and directing of treatment of the disease. For example, such differentially expressed gene products may include but are not limited to atherosclerosis specific adhesion molecules responsible for atherogenesis, or monocyte scavenger receptors that are up-regulated in response to oxidized LDL, which are discussed in Section 2, above. Alternatively, other such surface proteins may be specifically up-regulated in tissues suffering from ischemia/reperfusion or other tissues with atherosclerotic or restenotic lesions.

As described in the example in Section 6, below, fchd602 is a gene that is up-regulated in monocytes under disease conditions. Furthermore, the fchd602 gene encodes a novel protein containing multiple transmembrane domains. Not only is the fchd602 gene expressed in monocytes, which play a role in the initiation and progression of atherosclerotic lesions, it is also upregulated in monocytes under such disease conditions. The fchd602 gene product, therefore, provides and excellent tool for imaging cardiovascular disease conditions.

This method can be applied in a similar manner to other transmembrane target gene products, such as the fchd545 gene product. As described in the example in Section 7, below, the fchd545 gene encodes a novel anion channel, containing multiple transmembrane domains. Because the fchd545 gene product might be more readily detected in normal tissue, as opposed to tissue in the disease state, it also provides an excellent tool for imaging cardiovascular disease conditions.

An example illustrating the use of this method in accordance with the invention is provided in Section 9, below. Monoclonal and polyclonal antibodies, as described in Section 5.6.1.2, above, which specifically bind to such surface proteins, such as the fchd602 and fchd545 gene products, can be used for the diagnosis of cardiovascular disease by in vivo tissue imaging techniques. Such antibodies raised against the fchd545 gene product are described in detail in the example in Section 10, below. An antibody specific for a target gene product, or preferably an antigen binding fragment thereof, is conjugated to a label (e.g., a gamma emitting radioisotope) which generates a etectable signal and administered to a subject (human or animal) suspected of having cardiovascular disease. After sufficient time to allow the detectably-labeled antibody to localize at the diseased or damaged tissue site (or sites), the signal generated by the label is detected by a photoscanning device. The detected signal is then converted to an image of the tissue. This image makes it possible to localize the tissue in vivo. This data can then be used to develop an appropriate therapeutic strategy.

Antibody fragments, rather than whole antibody molecules, are generally preferred for use in tissue imaging. Antibody fragments accumulate at the tissue(s) more rapidly because they are distributed more readily than are entire antibody molecules. Thus an image can be obtained in less time than is possible using whole antibody. These fragments are also cleared more rapidly from tissues, resulting in a lower background signal. See, e.g., Haber et al., U.S. Pat. No. 4,036,945; Goldenberg et al., U.S. Pat. No. 4,331,647. The divalent antigen binding fragment (Fab')$_2$ and the monovalent Fab are especially preferred. Such fragments can be prepared by digestion of the whole immunoglobulin molecule with the enzymes pepsin or papain according to any of several well known protocols. The types of labels that are suitable for conjugation to a monoclonal antibody for diseased or damaged tissue localization include, but are not limited to radiolabels (i.e., radioisotopes), fluorescent labels and biotin labels.

Among the radioisotopes that can be used to label antibodies or antibody fragments, gamma-emitters, positronemitters, X-ray-emitters and fluorescence-emitters are suitable for localization. Suitable radioisotopes for labeling antibodies include Iodine-131, Iodine-123, Iodine-125, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18. The halogens can be used more or less interchangeably as labels since halogen-labeled antibodies and/or normal immunoglobulins would have substantially the same kinetics and distribution and similar metabolism.

The gamma-emitters Indium-111 and Technetium-99m are preferred because these radiometals are detectable with a gamma camera and have favorable half lives for imaging in vivo. Antibody can be labelled with Indium-111 or Technetium-99m via a conjugated metal chelator, such as DTPA (diethlenetriaminepentaacetic acid). See Krejcarek et al., 1977, Biochem. Biophys. Res. Comm. 77:581; Khaw et al., 1980, Science 209:295; Gansow et al., U.S. Pat. No. 4,472,509; Hnatowich, U.S. Pat. No. 4,479,930, the teachings of which are incorporated herein by reference.

Fluorescent compounds that are suitable for conjugation to a monoclonal antibody include fluorescein sodium, fluorescein isothiocyanate, and Texas Red sulfonyl chloride. See, DeBelder & Wik, 1975, Carbohydrate Research 44:254–257. Those skilled in the art will know, or will be able to ascertain with no more than routine experimentation, other fluorescent compounds that are suitable for labeling monoclonal antibodies.

6. EXAMPLE: IDENTIFICATION OF GENES DIFFERENTIALLY EXPRESSED IN RESPONSE TO PARADIGM A: IN VITRO FOAM CELL PARADIGM

According to the invention, differential display may be used to detect genes that are differentially expressed in monocytes that were treated so as to simulate the conditions under which foam cells develop during atherogenesis. By use of Paradigm A, the novel genes fchd602 and fchd605 were identified. Both fchd602 and fchd605 are up-regulated under the disease condition of treatment with oxidized LDL.

The fchd602 gene product contains multiple transmembrane domains, and has sequence similarity to the rat Cl-6 gene, hich is induced in regenerating rat liver, is insulin inducible, and also contains multiple transmembrane domains (Diamond, R. H., et al., 1993, J. Biol. Chem. 268: 15185–15192). The fchd605 gene product has sequence similarity to the mouse gly96 gene (Charles, C. H., et al., 1993, Oncogene 8: 797–801), and to EST T49532.

The discovery of the up-regulation of these two genes provides a fingerprint profile, e.g., markers, for monocytes in the process of foam cell formation. This profile can be used in the treatment and diagnosis of cardiovascular disease, including but not limited to atherosclerosis, ischemia/reperfusion, hypertension, restenosis, and arterial inflammation.

Furthermore, as a transmembrane protein, the fchd602 gene product can be readily accessed or detected on the monocyte cell surface by other compounds. It provides, therefore, an excellent target for detection of cardiovascular disease states in diagnostic systems, as well as in the monitoring of the efficacy of compounds in clinical trials. Furthermore, the extracellular domains of this gene product provide targets which allow for the design of especially efficient screening systems for identifying compounds that bind to them. Such compounds can be useful in treating cardiovascular disease by modulating the activity of the transmembrane gene product.

6.1. MATERIALS AND METHODS

6.1.1. CELL ISOLATION AND CULTURING

Blood (~200 ml) was drawn into chilled 20 ml vacutainer tubes to which 3 ml of citrate phosphate dextrose (Sigma) was added. Blood was then pooled into 50 ml tubes and spun in the Beckman GS-6R at 1250 RPM for 15 minutes at 4° C. The upper clear layer (~25 ml) was then removed with a pipette and discarded and replaced with the same volume of 4° C. PBS. The blood was then mixed, and spun again at 2680 RPM for 15 minutes at 4° C. The upper layer was then removed and discarded, and the buffy coat at the interface was removed in ~5 ml and placed in a separate 50 ml tube, and the pipette was washed with 20 ml PBS. Cells were added to a T flask and stored at 4° C. for 16 hours. A small aliquot of the cells were then removed and counted using a hemacytometer. The final red blood cell concentration in the buffy coat population was then adjusted to $1.5 \times 10^9$/ml with PBS, the cells were added to Leucoprep tubes (Becton Dickinson) after being allowed to come to room temperature, and spun at 2300 RPM for 25 minutes at 25° C. The upper clear layer was removed and discarded and the turbid layer over the gel was removed and pooled in 50 ml tubes. Samples were then diluted to 50 ml with PBS (25° C.) and spun at 1000 RPM for 10 minutes. The supernatant was then removed, and the pellet was resuspended in 50 ml PBS. This procedure was repeated 3 more times. After the last spin, the cells were resuspended in a small volume of PBS and counted.

Tissue culture dishes were coated with bovine collagen before monocytes were plated out. ⅙ volume of 7×RPMI (JRH Biosciences) was added to Vitrogen 100 collagen (Celtrix) which was then diluted 1:10 with RPMI to a final concentration of 0.35 mg/ml. Collagen mixture was then added to plates (2.5 ml/100 mm dish) and placed at 37° C. for at least one hour to allow for gel formation. After gel formation has taken place, the RPMI was removed and cells were added in RPMI/10% plasma derived serum (PDS). PDS was prepared by drawing blood into chilled evacuated tubes containing ¹⁄₁₀th volume 3.8% sodium citrate. Blood was then transferred into new Sorvall tubes and spun at 14,000–16,000 RPM for 20 minutes at 4° C. Plasma layer was removed and pooled in new tubes to which ¹⁄₅₀th volume 1M $CaCl_2$ was added. Plasma was mixed and aliquoted into new Sorvall tubes and incubated at 37% for 2 hours to allow for fibrin clot formation. The clot was then disturbed with a pipette to allow it to contract and tubes were spun at 14,500 RPM for 20 minutes at 25° C. Supernatant was collected, pooled, and heat inactivated at 56° C. prior to sterile filtration and freezing.

Purified human monocytes were cultured in 10% PDS/RPMI containing 5 units/ml of Genzyme recombinant human MCSF for 5 days before being treated with LDL, oxidized LDL, acetylated LDL (all LDL at 50 μg/ml), lysophosphatidylcholine (Sigma, 37.5 μM), or homocysteine (Sigma, 1 mM). After incubation with these reagents for periods ranging from 2 hours up to 3 days, the media was withdrawn and the cells were dissolved in RNA lysis buffer and RNA was prepared as described, above, in Section 6.1.

Lipoproteins For oxidation, human LDL (Sigma) was first diluted to 1 mg/ml with PBS and then dialyzed against PBS at 4° C. overnight. LDL was then diluted to 0.3 mg/ml with PBS. $CuSO_4.5H_2O$ was then added to 5 uM final concentration, and the solution was incubated in a T flask in a 37° C. incubator for 24 hr. LDL solution was then dialyzed at 4° C. against 0.15M NaCl/0.3 mM EDTA for 2 days with several changes, before being removed and concentrated using an Amicon spin column by spinning for 1 hr. 4000 RPM at 4° C.

For acetylation, 1 ml of 5 mg/ml LDL was added to 1 ml of a saturated solution of NaOAc in a 15 ml tube on ice on a shaker at 4° C. 8 μl of acetic anhydride was added 2 μl at a time over 1 hr. LDL was then dialyzed for 48 hr. against 0.15M NaCl/0.3 mM EDTA at 4° C. for 48 hr. with several changes. Final concentrations of derivatized LDL's were determined by comparing to a dilution curve of native LDL analyzed at $OD_{280}$, with 0.15M NaCl/0.3 mM EDTA used as diluent in all cases.

6.1.2. ANALYSIS OF PARADIGM MATERIAL

Differential Display:

Removal of DNA: The RNA pellet was resuspended in $H_2O$ and quantified by spectrophotometry at $OD_{260}$. Approximately half of the sample was then treated with DNAse I to remove contaminating chromosomal DNA. RNA was amplified by PCR using the following procedure. 50 ul RNA sample (10–20 μg), 5.7 μl 10×PCR buffer (Perkin-Elmer/Cetus), 1 μl RNAse inhibitor (40 units/μl) (Boehringer Mannheim, Germany) were mixed together, vortexed, and briefly spun. 2 μl DNAse I (10 units/μl) (Boehringer Mannheim) was added to the reaction which was incubated for 30 min. at 37° C. The total volume was brought to 200 μl with DEPC $H_2O$, extracted once with phenol/chloroform, once with chloroform, and precipitated by adding 20 μl 3M NaOAc, pH 4.8, (DEPC-treated), 500 μl absolute ETOH and incubating for 1 hour on dry ice or −20° C. overnight. The precipitated sample was centrifuged for 15 min., and the pellet was washed with 70% ETOH. The sample was re-centrifuged, the remaining liquid was aspirated, and the pellet was resuspended in 100 μl $H_2O$. The concentration of RNA was measured by reading the $OD_{260}$.

First strand cDNA synthesis: For each RNA sample duplicate reactions were carried out in parallel. 400 ng RNA plus DEPC $H_2O$ in a total volume of 10 μl were added to 4 μl $T_{11}XX$ reverse primer (10 μM) (Operon). The specific primers used in each experiment are provided in the Description of the Figures in Section 4, above. The mixture was incubated at 70° C. for 5 min. to denature the RNA and then placed at r.t. 26 μl of reaction mix containing the following components was added to each denatured RNA/primer sample: 8 μl 5×First Strand Buffer (Gibco/BRL, Gaithersburg, Md.), 4 μl 0.1M DTT (Gibco/BRL), 2 μl RNAse inhibitor (40 units/μl) (Boehringer Mannheim), 4 μl 200 μM dNTP mix, 6 μl $H_2O$, 2 μl Superscript reverse transcriptase (200 units/μl) (Gibco/BRL). The reactions were mixed gently and incubated for 30 min. at 42° C. 60 μl of $H_2O$ (final volume=100 μl) were then added and the samples were denatured for 5 min. at 85° C. and stored at −20° C.

PCR reactions: 13 μl of reaction mix was added to each tube of a 96 well plate on ice. The reaction mix contained 6.4 μl $H_2O$, 2 μl 10×PCR Buffer (Perkin-Elmer), 2 μl 20 μM dNTP's, 0.4 μl $^{35}S$ dATP (12.5 μCi/μl; 50 μCi total) (Dupont/NEN), 2 μl forward (for-) primer (10 μM) (Operon), and 0.2 μl AmpliTaq Polymerase (5 units/μl) (Perkin-Elmer). Next, 2 μl of reverse (rev-) primer ($T_{11}XX$, 10 μM) were added to the side of each tube followed by 5 μl of cDNA also to the sides of the tubes, which were still on ice. The specific primers used in each experiment were as follows:

fchd602: rev-$T_{11}XC$ (SEQ ID NO:13) and for-GTGAGGCGTC (SEQ ID NO:14)

fchd605: rev-$T_{11}XC$ (SEQ ID NO:13) and for-TGGACCGGTG (SEQ ID NO:15)

Tubes were capped and mixed, and brought up to 1000 RPM in a centrifuge then returned immediately to ice. The PCR machine (Perkin-Elmer 9600) was programmed for differential display as follows:

| | |
|---|---|
| 94° C. | 2 min. |
| *94° C. | 15 sec. |
| *40° C. | 2 min. |
| *ramp 72° C. | 1 min. |
| *72° C. | 30 sec. |
| 72° C. | 5 min. |
| 4° C. | hold |

*= X40

When the PCR machine reached 94° C., the plate was removed from ice and placed directly into the Perkin-Elmer 9600 PCR machine. Following PCR, 15 μl of loading dye, containing 80% formamide, 10 mM EDTA, 1 mg/ml xylene cyanol, 1 mg/ml bromphenol blue were added. The loading dye and reaction were mixed, incubated at 85° C. for 5 min., cooled on ice, centrifuged, and placed on ice. Approximately 4 μl from each tube were loaded onto a prerun (60 V) 6% acrylamide gel. The gel was run at approximately 80 V until top dye front was about 1 inch from bottom. The gel was transferred to 3 MM paper (Whatman Paper, England) and dried under vacuum. Bands were visualized by autoradiography.

Band isolation and amplification: Differentially expressed bands were excised from the dried gel with a razor blade and placed into a microfuge tube with 100 μl $H_2O$ and heated at 100° C. for 5 min., vortexed, heated again to 100° C. for 5 min., and vortex again. After cooling, 100 μl $H_2O$, 20 μl 3M NaOAc, 1 μl glycogen (20 mg/ml), and 500 μl ethanol were added and chilled. After centrifugation, the pellet was washed and resuspended in 10 μl $H_2O$.

The isolated differentially expressed bands were then amplified by PCR using the following reaction conditions:

| | |
|---|---|
| 58 μl | $H_2O$ |
| 10 μl | 10x PCR Buffer |
| 10 μl | 200 μm dNTP's |
| 10 μl | 10 μM reverse primer |
| 10 μl | 10 μM forward primer |
| 1.5 μl | amplified band |
| 0.5 μl | AmpliTaq polymerase (5 units/μl) (Perkin Elmer) |

PCR was performed using the program described in this Section, above, for differential display. After PCR, glycerol loading dyes were added and samples were loaded onto a 2% preparative TAE/Biogel (Bio101, La Jolla, Calif.) agarose gel and eluted. Bands were then excised from the gel with a razor blade and vortexed for 15 min. at r.t., and purified using the Mermaid kit from Bio101 by adding 3 volumes of Mermaid high salt binding solution and 8 μl of resuspended glassfog in a microfuge tube. Glassfog was then pelleted, washed 3 times with ethanol wash solution, and then DNA was eluted twice in 10 μl at 50° C.

Subcloning: The TA cloning kit (Invitrogen, San Diego, Calif.) was used to subclone the amplified bands. The ligation reaction typically consisted of 4 μl sterile $H_2O$, 1 μl ligation buffer, 2 μl TA cloning vector, 2 μl PCR product, and 1 μl T4 DNA ligase. The volume of PCR product can vary, but the total volume of PCR product plus $H_2O$ was always 6 μl. Ligations (including vector alone) were incubated overnight at 12° C. before bacterial transformation. TA cloning kit competent bacteria (INVαF': enda1, recA1, hsdR17(r-k, m+k), supE44, λ-, thi-1, gyrA, relA1, φ80lacZαΔM15Δ(lacZYA-argF), deoR+, F') were thawed on ice and 2 μl of 0.5 M β-mercaptoethanol were added to each tube. 2 μl from each ligation were added to each tube of competent cells (50 μl), mixed without vortexing, and incubated on ice for 30 min. Tubes were then placed in 42° C. bath for exactly 30 sec., before being returned to ice for 2 min. 450 μl of SOC media (Sambrook et al., 1989, supra) were then added to each tube which were then shaken at 37° C. for 1 hr. Bacteria were then pelleted, resuspended in ~200 μl SOC and plated on Luria broth agar plates containing X-gal and 60 μg/ml ampicillin and incubated overnight at 37° C. White colonies were then picked and screened for inserts using PCR.

A master mix containing 2 μl 10×PCR buffer, 1.6 μl 2.5 mM dNTP's, 0.1 μl 25 mM MgCl$_2$, 0.2 μl M13 reverse primer (100 ng/μl), 0.2 μl M13 forward primer (100 ng/μl), 0.1 μl AmpliTaq (Perkin-Elmer), and 15.8 μl H$_2$O was made. 40 μl of the master mix were aliquoted into tubes of a 96 well plate, and whole bacteria were added with a pipette tip prior to PCR. The PCR machine (Perkin-Elmer 9600) was programmed for insert screening as follows:

|  |  |
|---|---|
| 94° C. | 2 min. |
| *94° C. | 15 sec. |
| *40° C. | 2 min. |
| *ramp 72° C. | 30 sec. |
| *72° C. | 30 sec. |
| 72° C. | 10 min. |
| 4° C. | hold |

*= X35

Reaction products were eluted on a 2% agarose gel and compared to vector control. Colonies with vectors containing inserts were purified by streaking onto LB/Amp plates. Vectors were isolated from such strains and subjected to sequence analysis, using an Applied Biosystems Automated Sequencer (Applied Biosystems, Inc. Seattle, Wash.).

Northern analysis: Northern analysis was performed to confirm the differential expression of the genes corresponding to the amplified bands. The probes used to detect mRNA were synthesized as follows: typically 2 μl amplified band (~30 ng), 7 μl H$_2$O, and 2 μl 10×Hexanucleotide mix (Boehringer-Mannheim) were mixed and heated to 95° C. for 5 min., and then allowed to cool on ice. The volume of the amplified band can vary, but the total volume of the band plus H$_2$O was always 9 μl. 3 μl dATP/dGTP/dTTP mix (1:1:1 of 0.5 mM each), 5 μl α$^{32}$P dCTP 3000 Ci/mM (50 μCi total) (Amersham, Arlington Heights, Ill.), and 1 μl Klenow (2 units) (Boehringer-Mannheim) were mixed and incubated at 37° C. After 1 hr., 30 μl TE were added and the reaction was loaded onto a Biospin-6™ column (Biorad, Hercules, Calif.), and centrifuged. 1 μl aliquot of eluate was used to measure incorporation in a scintillation counter with scintillant to ensure that 10$^6$cpm/μl of incorporation was achieved.

The samples were loaded onto a denaturing agarose gel. A 300 ml 1% gel was made by adding 3 g of agarose (SeaKem™ LE, FMC BioProducts, Rockland, Me.) and 60 ml of 5×MOPS buffer to 210 ml sterile H2O. 5×MOPS buffer (0.1M MOPS (pH 7.0), 40 mM NaOAc, 5 mM EDTA (pH 8.0)) was made by adding 20.6 g of MOPS to 800 ml of 50 mM NaOAc (13.3 ml of 3M NaOAc pH 4.8 in 800 ml sterile H$_2$O); then adjusting the pH to 7.0 with 10M NaOH; adding 10 ml of 0.5M EDTA (pH8.0); and adding H$_2$O to a final volume of 1 L. The mixture was heated until melted, then cooled to 50° C., at which time 5 μl ethidium bromide (5 mg/ml) and 30 ml of 37% formaldehyde of gel were added. The gel was swirled quickly to mix, and then poured immediately.

2 μg RNA sample, 1×final 1.5×RNA loading dyes (60% formamide, 9% formaldehyde, 1.5×MOPS, 0.075% XC/BPB dyes) and H$_2$O were mixed to a final volume of 40 μl. The tubes were heated at 65° C. for 5 min. and then cooled on ice. 10 μg of RNA MW standards (New England Biolabs, Beverly, Mass.) were also denatured with dye and loaded onto the gel. The gel was run overnight at 32 V in MOPS running buffer.

The gel was then soaked in 0.5 μg/ml Ethidium Bromide for 45 min., 50 mM NaOH/0.1 M NaCl for 30 min., 0.1 M Tris pH 8.0 for 30 min., and 20×SSC for 20 min. Each soaking step was done at r.t. with shaking. The gel was then photographed along with a fluorescent ruler before blotting with Hybond-N embrane (Amersham), according to the methods of Sambrook et al., 1989, supra, in 20×SSC overnight.

Northern blot hybridizations were carried out as follows: for pre-hybridization, the blot was placed into roller bottle containing 10 ml of rapid-hyb solution (Amersham), and placed into 65° C. incubator for at least 1 hr. For hybridization, 1×10$^7$ cpm of the probe was then heated to 95° C., chilled on ice, and added to 10 ml of rapid-hyb solution. The prehybridization solution was then replaced with probe solution and incubated for 3 hr at 65° C. The following day, the blot was washed once for 20 min. at r.t. in 2×SSC/0.1% SDS and twice for 15 min. at 65° C. in 0.1×SSC/0.1% SDS before being covered in plastic wrap and put down for exposure.

RT-PCR Analysis: RT-PCR was performed to detect differentially expressed levels of mRNA from the genes corresponding to amplified bands. First strand synthesis was conducted by mixing 20 μl DNased RNA (~2 μg), 1 μl oligo dT (Operon) (1 μg), and 9.75 μl H$_2$O. The samples were heated at 70° C. for 10 min., and then allowed to cool on ice. 10 μl first strand buffer (Gibco/BRL), 5 μl 0.1M DTT, 1.25 μl 20 mM dNTP's (500 μM final), 1 μl RNAsin (40 units/μl) (Boehringer Mannheim), and 2 μl Superscript Reverse Transcriptase (200 units/μl) (Gibco/BRL) were added to the reaction, incubated at 42° C. for 1 hr., and then placed at 85° C. for 5 min., and stored at −20° C.

PCR was performed on the reverse transcribed samples. Each reaction contained 2 μl 10×PCR buffer, 14.5 μl H$_2$O, 0.2 μl 20 mM dNTP's (200 μM final), 0.5 μl 20 μM forward primer (0.4 μM final), 0.5 μl 20 μM reverse primer (0.4 μM final), 0.3 μl AmpliTaq polymerase (Perkin-Elmer/Cetus), 2 μl cDNA dilution or positive control (~40 pg). The specific primers used in each experiment are provided in the Description of the Figures in Section 4, above. Samples were placed in the PCR 9600 machine at 94° C. (hot start), which was programmed as follows:

|  |  |  |
|---|---|---|
| 94° C. | 2 min. | (samples loaded) |
| *94° C. | 45 sec. |  |
| *55° C. | 45 sec. |  |
| *72° C. | 2 min. |  |
| 72° C. | 5 min. |  |
| 4° C. | hold |  |

*= 35x

Reactions were carried out on cDNA dilution series and tubes were removed at various cycles from the machine during 72° C. step. Reaction products were eluted on a 1.8% agarose gel and visualized with ethidium bromide.

Gene Retrieval: Amplified sequences, which contained portions of the genes, were subcloned and then used individually to retrieve a cDNA encoding the corresponding gene. Probes were prepared by isolating the subcloned insert DNA from vector DNA, and labeling with $^{32}$P as described above in Section 6.1.2. Labeled insert DNA containing fchd602 sequences was used to probe a cDNA library prepared from human macrophage cell line U937. Labeled insert DNA containing fchd605 sequences was used to probe a cDNA library prepared from human primary blood monocytes. The cDNA libraries were prepared and screened according to methods routinely practiced in the art (see Sambrook et al., 1989, supra). Plaques from the libraries that were detected by the probes were isolated and the cDNA insert within the phage vector was sequenced.

The RACE procedure kit was used either as an alternative to cDNA library screening, or, when the cDNA library did not yield a clone encoding the full-length gene, to obtain adjacent sequences of the gene. The procedure was carried out according to the manufacturer's instructions (Clontech, Palo Alto, Calif.; see also: Chenchik, et al., 1995, CLONTECHniques (X) 1: 5–8; Barnes, 1994, Proc. Natl. Acad. Sci. USA 91: 2216–2220; and Cheng et al., Proc. Natl. Acad. Sci. USA 91: 5695–5699). Primers were designed based either on amplified sequences, or on sequences obtained from isolates from the cDNA libraries. Template mRNA for fchd605 was isolated from human primary blood monocytes.

6.1.3. CHROMOSOMAL LOCALIZATION OF TARGET GENES

Once the nucleotide sequence has been determined, the presence of the gene on a particular chromosome is detected. Oligonucleotide primers based on the nucleotide sequence of the target gene are used in PCR reactions using individual human chromosomes as templates. Individual samples of each the twenty-three human chromosomes are commercially available (Coriel Institute for Medical Research, Camden, N.J.). The chromosomal DNA is amplified according to the following conditions: long chromosomal DNA, 2 µl 10×PCR buffer, 1.6 µl 2.5 mM dNTP's, 0.1 µl 25 mM MgCl$_2$, 0.2 µl reverse primer (100 ng/µl), 0.2 µl forward primer (100 ng/µl), 0.1 µl Taq polymerase, and 15.8 µl H$_2$O. Samples are placed in the PCR 9600 machine at 94° C. (hot start), which is programmed as follows:

| | | |
|---|---|---|
| 94° C. | 2 min. | (samples loaded) |
| *94° C. | 20 sec. | |
| *55° C. | 30 sec. | |
| *72° C. | 30 min. | |
| 72° C. | 5 min. | |
| 4° C. | hold | |

*= 35x

6.2. RESULTS

Differential display was performed on monocytes treated with oxidized LDL and untreated monocytes. Bands corresponding to fchd602 and fchd605 were detected as up-regulated by oxidized LDL, as compared with the untreated monocytes. The up-regulation was confirmed by northern blot analysis.

The fchd602 gene produced a 2.5 kb mRNA that was up-regulated after 5 hours of treatment with oxidized LDL, minimally oxidized LDL, and lysophosphatidylcholine. No message was detected in untreated or native LDL treated control monocytes. The amplified DNA sequence was used to recover a cDNA of approximately 875 bp comprising an open reading frame encoding approximately 182 amino acids. The DNA sequence and encoded amino acid sequence of this cDNA from the fchd602 gene is shown in FIGS. 4A–4B. The open reading frame has 88% sequence similarity to the rat Cl-6 gene, which is induced in regenerating rat liver, is insulin inducible, and also contains multiple transmembrane domains (Diamond, R. H., et al., 1993, J. Biol. Chem. 268: 15185–15192).

The fchd605 gene produced a 1.5 kb mRNA that is up-regulated after 5 hours treatment with oxidized LDL, and to a lesser degree with native LDL, as compared to untreated monocytes. The amplified DNA was sequenced and used to recover a cDNA of approximately 2.2 kb, which was sequenced to reveal a partial open reading frame of approximately 258 bp, encoding approximately 86 amino acids. The DNA sequence and encoded amino acid sequence from the fchd605 gene is shown in FIGS. 5A–5B. The sequence has similarity to the mouse gly96 gene, which encodes a cytokine inducible glycosylated protein expressed in mouse lung, testes, and uterus.

7. EXAMPLE: IDENTIFICATION OF GENES DIFFERENTIALLY EXPRESSED IN RESPONSE TO PARADIGM D: ENDOTHELIAL CELL SHEAR STRESS

According to the invention, differential display was used to detect genes that are differentially expressed in endothelial cells that were subjected to fluid shear stress in vitro. Shear stress is thought to be responsible for the prevalence of atherosclerotic lesions in areas of unusual circulatory flow. Using the method of Paradigm D, three novel DNA sequences were identified.

The fchd531 gene is down-regulated in endothelial cells under both turbulent and laminar shear stress, as compared to the static control. The fchd531 gene encodes a novel 570 amino acid polypeptide, and has 94% sequence similarity to the mouse penta zinc finger gene (Pzf), which has not been published, but is contained in the GenBank sequence data base under accession no U05343.

The fchd540 gene is up-regulated in endothelial cells under laminar shear stress, but is not up-regulated by IL-1 treatment. The fchd540 gene encodes a novel intracellular protein which has sequence similarity to the Drosophila Mad protein (Sekelsky et al., 1995, Genetics 139: 1347–1358).

The fchd545 gene is down-regulated in endothelial cells under laminar shear stress as compared to endothelial cells under turbulent shear stress and static control endothelial cells. The fchd545 gene encodes an 848 amino acid polypeptide which has 73% sequence similarity to the human Voltage-dependent Anion Channel protein (Blachly-Dyson, E., et al., 1993, J. Biol. Chem. 268: 1835–1841.). The fchd545 gene is also expressed in the human heart, smooth muscles, and testes.

The up-regulation of the fchd540 gene and down-regulation of the fchd531 and fchd545 genes in shear stressed endothelial cells provides a fingerprint for the study of cardiovascular diseases, including but not limited to atherosclerosis, ischemia/reperfusion, hypertension, and restenosis. The fact that one of these genes, fchd540, is not up-regulated under Paradigm C (IL-1 induction) provides an extremely useful means of distinguishing and targeting physiological phenomena specific to shear stress.

Furthermore, as a transmembrane protein, the fchd545 gene product can be readily accessed or detected on the endothelial cell surface by other compounds. It provides, therefore, an excellent target for detection of cardiovascular disease states in diagnostic systems, as well as in the monitoring of the efficacy of compounds in clinical trials. Furthermore, the extracellular domains of this gene product provide targets which allow for designing especially efficient screening systems for identifying compounds that bind to them. Such compounds can be useful in treating cardiovascular disease by modulating the activity of the transmembrane gene product.

7.1. MATERIALS AND METHODS

Primary cultures of HUVEC's were established from normal term umbilical cords as described (In Progress in Hemostasis and Thrombosis, Vol. 3, P. Spaet, editor, Grune & Stratton Inc., New York, 1–28). Cells were grown in 20% fetal calf serum complete media (1989, J. Immunol. 142: 2257–2263) and passaged 1–3 times before shear stress induction.

For induction, second passage HUVEC's were plated on tissue culture-treated polystyrene and subjected to 10 dyn/cm$^2$ laminar flow for 1 and 6 hr. as described (1994, J. Clin. Invest. 94: 885–891) or 3–10 dyn/cm$^2$ turbulent flow as previously described (1986 Proc. Natl. Acad. Sci. U.S.A. 83: 2114–2117). RNA was isolated as described, above, in Section 6.1. Differential display, Northern analysis, RT-PCR, subcloning, and DNA sequencing were carried out as described, above, in Section 6.1.2. Specific primers used in differential display were as follows:

fchd531: for-T$_{11}$XA (SEQ ID NO:16) and rev-AGACGTCCAC (SEQ ID NO:17)

fchd540: for-T$_{11}$XA (SEQ ID NO:16) and rev-ACTTCGCCAC (SEQ ID NO:18)

fchd545: for-T$_{11}$XC (SEQ ID NO:13) and rev-TCGGACGTGA (SEQ ID NO:19)

Amplified sequences, which contained portions of the genes, were subcloned and then used individually to retrieve a cDNA encoding the corresponding gene. Probes were prepared by isolating the subcloned insert DNA from vector DNA, and labeling with $^{32}$p as described above in Section 6.1.2. Labeled insert DNA was used to probe cDNA library prepared from shear stress induced endothelial cells. The library was prepared and probed using methods routinely practiced in the art (see Sambrook et al., 1989, supra). Plaques from the libraries that were detected by the probes were isolated and the cDNA insert within the phage vector was sequenced.

The RACE procedure kit was used either as an alternative to cDNA library screening, or, when the cDNA library did not yield a clone encoding the full-length gene, to obtain adjacent sequences of the gene. The procedure was carried out according to the manufacturer's instructions (Clontech, Palo Alto, Calif.; see also: Chenchik, et al., 1995, CLONTECHniques (X) 1: 5–8; Barnes, 1994, Proc. Natl. Acad. Sci. USA 91: 2216–2220; and Cheng et al., Proc. Natl. Acad. Sci. USA 91: 5695–5699). Primers were designed based either on amplified sequences, or on sequences obtained from isolates from the cDNA libraries. Template mRNA was isolated from shear stressed HUVEC's.

Northern blot analysis of RNA extracted from various human organs and tissues was performed using commercially available pre-blotted filters (Clontech, Palo Alto, Calif.).

7.2. RESULTS

An amplified fchd531 fragment obtained from differential display was subcloned and sequenced, and used to obtain a 1.9 kb cDNA containing the entire fchd531 coding region. The DNA sequence and encoded amino acid sequence of the novel fchd531 gene is shown in FIGS. 1A–1D. The fchd531 gene encodes a 570 amino acid polypeptide, and has 94% sequence similarity to the mouse penta zinc finger gene (Pzf) (GenBank accession number U05343). Northern analysis of HUVEC's which were subjected turbulent and laminar shear stress demonstrated that the fchd531 gene produces an approximately 5 kb message which is down-regulated under laminar shear stress, but not turbulent shear stress, compared with the static control.

The fchd540 gene was detected as an up-regulated message under shear stress. The amplified fragment was used to probe a Northern blot containing samples from HUVECs treated with laminar shear stress. A 4.4 kb fchd540 mRNA is up-regulated after 6 hours treatment with laminar shear stress. The fchd540 gene is not induced by IL-1 by the method of Paradigm C, (Section 5.1.1.5, above). The amplified fragment was sequenced and used to obtain a 2.7 kb cDNA containing the entire fchd540 coding region. The DNA sequence and encoded amino acid sequence from the fchd540 gene is shown in FIGS. 2A–2E. The fchd540 gene encodes a 426 amino acid polypeptide and has sequence similarity to the Drosophila Mad gene (Sekelsky et al., 1995, Genetics 139: 1347–1358).

The fchd545 gene was detected as a down-regulated message under shear stress. Northern analysis revealed that the fchd545 gene produces a 1.4 kb message which is down regulated by turbulent shear stress, but not by laminar shear stress, as compared with static control. The amplified fragment was sequenced and used to isolate a 1.4 kb cDNA containing the complete fchd545 coding sequence. The DNA sequence and encoded amino acid sequence of the fchd545 gene is shown in FIGS. 3A–3C. The fchd545 gene encodes a 283 amino acid polypeptide which has 73% sequence similarity to the human Voltage-dependent Anion Channel (Blachly-Dyson, E., et al., 1993, J. Biol. Chem. 268: 1835–1841). Northern analysis of a commercially available (Clontech, Palo Alto, Calif.) northern blot revealed that the fchd545 gene is expressed in human heart, smooth muscle, and testes.

8. EXAMPLE: USE OF GENES UNDER PARADIGM A AS SURROGATE MARKERS IN CLINICAL TRIALS

According to the invention, the fingerprint profile derived from any of the paradigms described in Sections 5.1.1.1 through 5.1.1.6 may be used to monitor clinical trials of drugs in human patients. The fingerprint profile, described generally in Section 5.5.4, above, indicates the characteristic pattern of differential gene regulation corresponding to a particular disease state. Paradigm A, described in Section 5.1.1.1, and illustrated in the example in Section 6, above, for example, provides the fingerprint profile of monocytes under oxidative stress. The target genes, therefore, serve as surrogate markers by giving an indicative reading of the physiological response of monocytes to the uptake of oxidized LDL. Accordingly, the influence of anti-oxidant drugs on the oxidative potential may be measured by performing differential display on the monocytes of patients undergoing clinical tests.

8.1. TREATMENT OF PATIENTS AND CELL ISOLATION

Test patients may be administered compounds suspected of having anti-oxidant activity. Control patients may be given a placebo.

Blood may be drawn from each patient after a 12 hour period of fasting and monocytes may be purified as described, above, in Section 7.1.1. RNA may be isolated as described in Section 6.1.1, above. Primers may then be designed for amplification based on the DNA sequence of target genes identified as up-regulated, such as fchd602 and fchd605, or down-regulated under Paradigm A.

8.2. ANALYSIS OF SAMPLES

RNA may be subjected to differential display analysis as described in Section 6.1.2, above. A decrease in the physiological response state of the monocytes is indicated by a decreased intensity of those bands corresponding to fchd602 and fchd605, which were up-regulated by oxidized LDL under Paradigm A, as described in Section 6.2, above.

dorsal sites for a total volume of 1.0 ml (0.5 mg peptide) per immunization. The animals were boosted after 2 and 6 weeks and bled at weeks 4, 8, and 10. The blood was allowed to clot and serum was collected by centrifugation.

The peptides used are summarized below:

fchd545 Peptide Antigens

| fchd545 Peptide Antigens | | | |
|---|---|---|---|
| Name | Position | Sequence | |
| fchd545.1 | 48–63 | YTDTGKASGNLETKYK | (SEQ ID NO: 43) |
| fchd545.2 | 107–121 | TGKKSGKLKASYKRD | (SEQ ID NO: 44) |

9. EXAMPLE: IMAGING OF A CARDIOVASCULAR DISEASE CONDITION

According to the invention, differentially expressed gene products which are localized on the surface of affected tissue may be used as markers for imaging the diseased or damaged tissue. Conjugated antibodies that are specific to the differentially expressed gene product may be administered to a patient or a test animal intravenously. This method provides the advantage of allowing the diseased or damaged tissue to be visualized non-invasively.

For the purposes of illustration, this method is described in detail for the fchd602 gene product. The principles and techniques can be applied to any transmembrane target gene product, including, for example, the fchd545 gene product.

9.1. MONOCLONAL CONJUGATED ANTIBODIES

The differentially expressed surface gene product, such as the fchd602 gene product, is expressed in a recombinant host and purified using methods described in Section 5.4.2, above. Preferably, a protein fragment comprising one or more of the extracellular domains of the fchd602 product is produced. Once purified, it is be used to produce $F(ab')_2$ or Fab fragments, as described in Section 5.4.3, above. These fragments are then labelled with technetium-99 m ($^{99m}Tc$) using a conjugated metal chelator, such as DTPA as described in section 5.8.3, above.

9.2. ADMINISTRATION AND DETECTION OF IMAGING AGENTS

Labeled MAb may be administered intravenously to a patient being diagnosed for atherosclerosis, restenosis, or ischemia/reperfusion. Sufficient time is allowed for the detectably-labeled antibody to localize at the diseased or damaged tissue site (or sites), and bind to the fchd602 gene product. The signal generated by the label is detected by a photoscanning device. The detected signal is then converted to an image of the tissue, revealing cells, such as monocytes, in which fchd602 gene expression is up-regulated.

10. POLYCLONAL ANTIBODIES TO TARGET GENE PEPTIDE SEQUENCES

Peptide sequences corresponding to the indicated amino sequences of cDNAs were selected and submitted to Research Genetics (Huntsville, Ala.) for synthesis and antibody production. Peptides were modified as described (Tam, J. P., 1988, Proc. Natl. Acad. Sci. USA 85: 5409–5413; Tam, J. P., and Zavala, F., 1989, J. Immunol. Methods 124: 53–61; Tam, J. P., and Lu, Y. A., 1989, Proc. Natl. Acad. Sci. USA 86: 9084–9088), emulsified in an equal volume of Freund's adjuvant and injected into rabbits at 3 to 4 subcutaneous

11. EXAMPLE: THE RCHD534 AND FCHD540 GENE PRODUCTS INTERACT

The novel fchd540 gene and its nucleotide sequence is described in Section 7, above. The fchd540 gene shares homology with the Drosophila Mad gene. The rchd534 gene (described in Applicant's co-pending Application Ser. No. 08/485,573, filed Jun. 7, 1995, which is incorporated by reference in its entirety herein) is another gene that is up-regulated in endothelial cells by shear stress. The DNA and encoded amino acid sequence of the rchd534 gene is shown in FIGS. 6A–6D. The rchd534 gene was deposited in the Agricultural Research Service Culture Collection (NRRL) in microorganism FCHD534 on Jun. 6, 1995 and assigned the NRRL Accession No. B-21459. The rchd534 gene also shares homology with the Drosophila Mad gene. Mad genes have been shown to play a role in the TGF-β signalling pathway (Sekelsky et al., 1995, Genetics 139: 1347–1358; Chen et al., 1996, Nature 383: 691–696; Serra, et al., 1996, Nature Medicine 2: 390–391). TGF-β signalling is considered to be beneficial to atherosclerosis and restenosis (Border et al., 1995, Nature Medicine 1: 1000; Grainger, et al., 1995, Nature Medicine 1: 1067–1073; Kojima, et al., 1991, J. Cell Biol. 113: 1439–1445; Nikol, et al., 1992, J. Clin. Invest. 90: 1582–1592).

The data described below demonstrate that the rchd534 and fchd540 proteins interact with one another; and this interaction may lead to the inhibition of TGF-β signalling. Furthermore, the expression of these two genes, as described below, is specific to endothelial cells. Because these two genes 1) are both expressed specifically in endothelial cells, 2) are both up-regulated in endothelial cells under certain conditions, 3) encode MAD proteins that interact with one another in endothelial cells, and 4) inhibit TGF-β signalling (which is considered to be beneficial to atherosclerosis), rchd534 and fchd540 proteins are attractive targets for therapeutic intervention in cardiovascular disease. In particular, treatment regimens that inhibit the interaction or activity of the rchd534 and fchd540 proteins can be beneficial for the treatment cardiovascular disease.

Further analyses demonstrated that the rchd534 protein interacts with itself to form a homodimer. Thus, treatment regimens that inhibit the interaction of the rchd534 protein with itself can be beneficial for the treatment cardiovascular disease.

In addition, the analyses described below demonstrated novel interactions of both the rchd534 and fchd540 proteins with other proteins known to be involved in the TGF-β signalling pathway. The protein members of the TGF-β signalling pathway tested included MADR1 (Hoodless et al., 1996, Cell 85:489–500), MADR2 (Eppert et al., 1996, Cell 86: 543–552), DPC4 (Raftery et al., 1988, Genetics 139: 241–254), TβRI, TSR1, ActRIb, ALK3, and ALK6 (Wieser et al., 1995, EMBO J. 14: 2199–2208). For example, the rchd534 protein interacts strongly in endothelial cells with MADR1, MADR2, DPC4, and weakly in 293 (human embryonic kidney) cells with activated forms of receptors TβRI and ActRI. The fchd540 protein interacts strongly in 293 cells with activated forms of receptors TβRI and ALK6.

In the absence of transfected rchd543 and fchd540 genes, transfected MADR1 or transfected MADR2 mediated a 20-fold induction of a TGF-β inducible promoter in BAECs. Co-expression of either transfected rchd534 or transfected rchd540 in this system eliminated the induction, and also prevented the localization of MADR2 in the nucleus in response to TGF-β signalling. Therefore, treatment regimens that inhibit the interaction of the rchd534 and fchd540 proteins with other proteins involved in the TGF-β pathway also can be beneficial for the treatment cardiovascular of disease. As described above, the expression of rchd534 and fchd540 is specific, within arterial tissue, to endothelial cells. Accordingly, the rchd534 and rchd540 genes may be targets for intervention in a variety of inflammatory and fibroproliferative disorders that involve endothelial cells, including, but not limited to, cancer, angiogenesis, inflammation, and fibrosis.

11.1. MATERIALS AND METHODS 11.1.1. YEAST STRAINS, MEDIA, AND MICROBIOLOGICAL TECHNIQUES

Standard yeast media including synthetic complete medium lacking L-leucine, L-tryptophan, and L-histidine were prepared and yeast genetic manipulations were performed as described (Sherman, 1991, Meth. Enzymol., 194:3–21). Yeast transformations were performed using standard protocols (Gietz et al., 1992, Nucleic Acids Res., 20:1425. Ito et al., 1983, J. Bacteriol., 153:163–168). Plasmid DNAs were isolated from yeast strains by a standard method (Hoffman and Winston, 1987, Gene, 57:267–272).

11.1.2. PLASMID AND YEAST STRAIN CONSTRUCTION

The coding region of human fchd540 was amplified by PCR and cloned in frame into pGBT9 (Bartel et al., 1993, Cellular Interactions in Development. pp. 153–159) resulting in plasmid pGBT9-fchd540. pGBT9-fchd540 was transformed into two-hybrid screening strain HF7c and one resulting transformant was designated TB35.

11.1.3. TWO-HYBRID SCREENING

Two-hybrid screening was carried out essentially as described (Bartel et al., 1993, supra) using TB35 as the recipient strain and a human breast two-hybrid library.

11.1.4. PAPER FILTER BETA-GALACTOSIDASE ASSAYS

The paper filter beta-galactosidase (beta-gal) assay was performed essentially as previously described (Brill et al., 1994, Mol. Biol. Cell 5: 297–312).

11.2. RESULTS 11.2.1. STRONG PHYSICAL INTERACTION OF RCHD534 AND FCHD540 MEASURED BY TWO-HYBRID ASSAY

The fchd540 coding sequence was amplified by PCR and cloned into pGBT9 creating a GAL4 DNA-binding domain-fchd540 fusion gene. The screening strain HF7c was transformed with this construct. The rchd534 coding sequence was cloned into pGAD424 (Bartel et al., 1993, supra) creating a GAL4 transcriptional activation domain-rchd534 fusion gene, which was then used to transform strain Y187.

Yeast expression plasmids encoding the GAL4 DNA-binding domain either alone or fused in frame to fchd540, rchd534, Drosophilia MAD, DPC4, or p53 were transformed into MATa two-hybrid screening strain HF7c. Yeast expression plasmids encoding the GAL4 transcriptional activation domain alone and GAL4 activation domain fusions to rchd534 and SV40 were transformed into MATα two-hybrid screening strain Y187. p53 and SV40 interact with each other and should not interact with the experimental proteins. The HF7c transformants were propagated as stripes on semisolid synthetic complete medium lacking L-tryptophan and the Y187 transformants were grown as stripes on semisolid synthetic complete medium lacking L-leucine. Both sets of stripes were replica plated in the form of a grid onto a single rich YPAD plate and the haploid strains of opposite mating types were allowed to mate overnight at 30° C. The yeast strains on the mating plate were then replica plated to a synthetic complete plate lacking L-leucine and L-tryptophan to select for diploids and incubated at 30° C. overnight. Diploid strains on the synthetic complete plate lacking L-leucine and L-tryptophan were replica plated to a synthetic complete plate lacking L-leucine, L-tryptophan, and L-histidine to assay HIS3 expression and a paper filter on a synthetic complete plate lacking L-leucine and L-tryptophan. The next day the paper filter was subjected to the paper filter beta-galactosidase assay to measure expression of the lacZ reporter gene. HIS3 expression was scored after 3 days of growth at 30° C. The results are shown in Table 3.

The rchd534 fish protein was found to interact strongly with the fchd540 bait protein and not to interact with the rchd534, MAD, DPC4, p53, and GAL4 DNA binding domain bait proteins. This result demonstrated that rchd534 and fchd540 strongly physically interact with each other with significant specificity.

11.2.2. IDENTIFICATION OF PROTEINS THAT PHYSICALLY INTERACT WITH FCHD540

The fchd540 coding sequence was amplified by PCR and cloned into pGBT9 (Bartel et al., 1993, supra) creating a GAL4 DNA-binding domain-fchd540 fusion gene. HF7c was transformed with this construct resulting in strain TB35. TB35 grew on synthetic complete medium lacking L-tryptophan but not on synthetic complete medium lacking L-tryptophan and L-histidine demonstrating that the GAL4 DNA-binding domain-fchd540 fusion does not have intrinsic transcriptional activation activity.

TB35 was transformed with the human breast two-hybrid library and 5 million transformants were obtained. The transformants were plated on synthetic complete medium lacking L-leucine, L-tryptophan, and L-histidine and yeast colonies that both grew on synthetic complete medium lacking L-leucine, L-tryptophan, and L-histidine and expressed the beta-galactosidase reporter gene were identified. The 30 strains with the strongest beta-galactosidase induction were characterized. Library plasmids were isolated from these strains, and the 5' ends of all of the cDNA inserts were sequenced.

11.2.3. RETRANSFORMATION AND SPECIFICITY TESTING OF TCHV03A AND TCHVR4A

Two of the plasmids that encoded the strongest interactors were found to contain rchd534 cDNAs. Plasmid tchv03A was found to encode amino acids 17–235 of rchd534 and plasmid tchvR4A was found to encode amino acids 25–235 of rchd534.

It was confirmed that these rchd534 cDNAs encode proteins that physically interact specifically with fchd540. Yeast expression plasmids encoding the GAL4 DNA-binding domain either alone or fused in frame to fchd540, rchd534, Drosophila MAD, DPC4, and p53 were transformed into MATa two-hybrid screening strain HF7c. Yeast expression plasmids encoding the GAL4 transcriptional activation domain (GAL4 AD) alone and GAL4 activation domain fusions to tchv03a, tchvR4A and SV40 were transformed into MATα two-hybrid screening strain Y187. p53 and SV40 interact with each other and should not interact with the experimental proteins. The HF7c transformants were propagated as stripes on semi-solid synthetic complete medium lacking L-leucine. Both sets of stripes were replica plated in the form of a grid onto a single rich YPAD plate and the haploid strains of opposite mating types were allowed to mate overnight at 30° C. The yeast strains on the mating plate were then replica plated to a synthetic complete plate lacking L-leucine and L-tryptophan to select for diploids and incubated at 30° C. overnight. Diploid strains on the synthetic complete plate lacking L-leucine and L-tryptophan were replica plated to a synthetic complete plate lacking L-leucine, L-tryptophan, and L-histidine to assay HIS3 expression and a paper filter on a synthetic complete plate lacking L-leucine and L-tryptophan. The next day the paper filter was subjected to the paper filter beta-galactosidase-assay to measure expression of the lacZ reporter gene. HIS3 expression was scored after 3 days of growth at 30° C. The results are shown in the table below. The strength or absence of physical interaction between each combination of test proteins is listed. Strong interactions are defined as interactions that cause the activation of both the HIS3 and lacZ reporter genes.

TABLE 3

| GAL4 DNA-Binding Domain Fusions | cDNA-GAL4 Activation Domain Fusion Tested | | | | GAL4 AD alone |
|---|---|---|---|---|---|
| | rchd534 | tchv03A | tchvR4A | SV40 | |
| fchd540 | Strong | Strong | Strong | None | None |
| rchd534 | None | None | None | None | None |
| Dros. MAD | None | None | None | None | None |
| DPC4 | None | None | None | None | None |
| p53 | None | None | None | Strong | None |
| GAL4 DNA-Binding Domain alone | None | None | None | None | None |

The tchv03A and tchvR4A fish proteins were found to interact strongly with the fchd540 bait protein and to not interact with the rchd534, MAD, DPC4, p53, and GAL4 DNA binding domain bait proteins. These results confirm the result that the rchd534 and fchd540 proteins interact strongly with each other.

11.3. FURTHER ANALYSIS OF RCHD534 AND FCHD540 FUNCTION

The significance of the rchd534/fchd540 protein interaction was confirmed by examination of their expression and activity in human cells and animal models.

11.3.1. CHROMOSOMAL LOCALIZATION

The rchd534 gene was localized to chromosome 15 and the fchd540 gene was localized to chromosome 18, regions of the human genome that contain other MAD homologues. These regions of the human genome have also been implicated in the pathogenesis of several human malignancies.

11.3.2. TISSUE EXPRESSION PATTERNS

The expression patterns were examined using in situ hybridization techniques. Fluorescently labeled DNA probes of both the rchd534 and fchd540 genes were used to probe human carotid endartectomy samples. The expression of rchd534 and fchd540 was specific to endothelial cells lining the luminal surface of the carotid artery. In addition, a rabbit polyclonal antiserum generated against the rchd534 gene product prominently and selectively stained the endothelium present in large vessels such as human coronary arteries as well as smaller vessels present within human myocardium. Neither gene showed expression in any other cell type present in the arterial tissue sample, including smooth muscle cells and macrophages.

Expression patterns of both genes were also examined in response to certain stimulus. Both genes are selectively upregulated under the steady laminar shear stress (LSS) paradigm, but not under the turbulent shear stress paradigm or in response to stimulus by the cytokines rhIL-1β, TNFα, IFNγ or active TGFβ as measured in HUVEC cells. Thus, the rchd534 and the fchd540 genes appear to be selectively responsive to a LSS stimulus, manifesting no response to a non-laminar fluid mechanical stimulus, nor any other humoral stimuli tested. Thus, given that these two genes are: (1) localized to a region of the human genome that has been implicated in the pathogenesis of several human malignancies; (2) specifically expressed in a cell-type that is found only in vascular tissue, including atherosclerotic plaques; (3) up-regulated under the steady laminar shear stress cardiovascular disease paradigm; and (4) specifically inhibit TGF-β signalling indicate that rchd534 and fchd540 are excellent and specific targets for therapeutic intervention in the treatment of fibroproliferative and oncogenic disorders including tumor growth and vascularization.

11.3.3. CELLULAR LOCALIZATION

The cellular localization of the rchd534 and fchd540 proteins in bovine aortic endothelial cells (BAECs) was examined in relationship to other proteins involved in the TGF-β signalling pathway. In all experiments, the rchd534 and fchd540 proteins were located in the cytoplasm. MADR2 was located in the cytoplasm when transfected alone and in the nucleus when co-transfected with activated TβRI or when TGF-β was added to the culture medium. Co-transfection of rchd534 or fchd540 with MADR2 prevented the localization of MADR2 in the nucleus in response to TGF-β signalling.

11.3.4. PROTEIN INTERACTIONS IN HUMAN CELLS

The Interaction of the rchd534 and fchd540 proteins, observed in yeast cells as described above, was tested in mammalian endothelial cell tissue culture. Either bovine aortic endothelial cells (BAECs) or 293 cells (human embryonic kidney cells, ATCC Accession No. CRL-1573) were transfected with constructs encoding both the rchd534 and fchd540 proteins, each fused to a different flag peptide allowing for specific immunoprecipitation. The rchd534 and fchd540 proteins were found to co-immunoprecipitate as heterodimers in extracts produced from both 293 cells and BAECs. The co-immunoprecipitation of rchd534 and fchd540 further supports that these proteins interact in human cells that are physiologically relevant to cardiovascular disease.

The ability of the rchd534 and fchd540 proteins to interact with themselves and with other protein members of the TGF-β signalling pathway (MADR1, MADR2, DPC4, TbR1, TSR1, ActR1b, ALK3, ALK6), was tested using this co-immunoprecipitation method. Each gene was transfected alone and in various combinations with other TGF-β pathway genes in either 293 cells or BAECs. The rchd534 protein formed homodimers in 293 cells and BAECs. The fchd540 protein did not form homodimers in 293 cells or BAECs. As mentioned above, the rchd534 and fchd540 proteins formed heterodimers in 293 cells and BAECs. This interaction is about 50 fold stronger in BAECs than 293 cells based on equal amounts of protein. However, the rchd534-fchd540 protein interaction was significantly less avid than the rchd534 protein's interaction with itself.

The rchd534 protein interacted with MADR1, MADR2, and DPC4 in 293 cells and BAECs. The strength of MADR1 and MADR2 interactions was about the same between 293 cells and BAECs and much greater in BAECs for DPC4. The fchd540 protein interacted very weakly with MADR1, MADR2, and DPC4 in 293 cells. The rchd534 protein interacted strongly with activated forms of TβRI and ActRI and weakly with activated ALK6 in 293 cells. The fchd540 protein interacted strongly with activated TβRI and ALK6 receptors, and weakly with activated forms of TSRI, ALK3, and ActRIb in 293 cells. Thus, in addition to the interaction of the rchd534 and fchd540 proteins, the interaction of the rchd534 protein with itself, as well as the interaction of the rchd534 protein and the fchd540 protein with the other proteins in the TGF-β pathway described above are excellent targets for therapeutic intervention.

11.3.5. EFFECT OF EXPRESSION ON TGF-B SIGNALLING

The effect of both rchd534 and fchd540 on the TGF-β signalling pathway was tested in vitro. Primary BAECs were transfected with a construct called p3TP-Lux, containing a TGF-β responsive promoter fused to a reporter gene (Wrana et al., 19944, Nature 370: 341–347). The rchd534 gene or the fchd540 gene in pCI expression vectors (Promega) was transfected with and without MADR1 (pCMV5MADR1-Flag, Hoodless et al. 1996 Cell 85: 489–500) or MADR2 (pCMV5MADR2-Flag, Eppert et al. 1996 Cell 86: 543–552). The TGF-β response was induced 20-fold by either MADR1 or MADR2. Co-expression of either rchd534 or fchd540 completely eliminated this induction. Thus, the rchd534 and fchd540 proteins inhibited MADR1- and MADR2-mediated TGF-β signalling in endothelial cells. To confirm the specificity of this inhibitory effect, site specific mutants of both rchd534 or fchd540 were constructed, based on known mutations identified in Drosophila homologues, that would be predicted to disrupt MAD-like signaling functions (Sekelsky et al., 1995, Genetics 139:1347–58; Raftery, 1995, Genetics 139:241–54; Newfeld et al., 1996, Development 122:2099–108; Wiersdorff et al., 1996, Development 122:2153–62). Unlike wild type rchd534 and fchd540, these mutant proteins were unable to inhibit the activation of the p3TP promoter in response to TGF-β. The expression levels of the mutant and wild-type proteins were comparable indicating the loss of function was not due to secondary instability.

Interestingly, Smad3, the *C. elegans* homolog to MAD3 which also functions in TGFβ signalling is over 90% identical to Smad2, the *C. elegans* MAD2 homolog, in the MH2 domain. Although this has not yet been directly investigated, it is likely that Smad7, the *C. elegans* homolog of the fchd540 gene, may function similarly to its inhibition to prevent association and activation of Smad3 by the TGFβ receptor, that is, to inhibit the phosphorylation of Smad3 and its association with protein components of the TGF-β signalling pathway.

These results further demonstrate that the interactions of either the rchd534 protein or the fchd540 protein with MADR2 or with activated TβR1 are excellent targets for therapeutic intervention. As described above, the expression of rchd534 and fchd540 is specific, within arterial tissue, to endothelial cells. Accordingly, the rchd534 and rchd540 genes may be targets for intervention in a variety of inflammatory and fibroproliferative disorders that involve endothelial cells, including, but not limited to, cancer angiogenesis, inflammation, and fibrosis.

12. EXAMPLE: ANTISENSE AND RIBOZYME MOLECULES FOR INHIBITION OF RCHD534 AND FCHD540 EXPRESSION

The principles presented in Section 5.6.1.1, above, can be used to design oligonucleotides for use in inhibiting the expression of target genes, such as the rchd534 or fchd540 genes.

The following antisense molecules can be used to inhibit the expression of the rchd534 gene:

Antisense:
a) 5'-CATTTCATTTCATACAA-3' (SEQ ID NO:20) which is complementary to nucleotides −14 to +3 of rchd534 in FIGS. 6A–6D.
b) 5'-CATTTCATTTCATACAATATATG-3' (SEQ ID NO:21) which is complementary to nucleotides −20 to +3 of rchd534 in FIGS. 6A–6D.
c) 5'-CATTTCATTTCATACAATATATGGCCTTT-3' (SEQ ID NO:22) which is complementary to nucleotides −26 to +3 of rchd534 in FIGS. 6A–6D.
d) 5'-CATTTCATTTCATACAATATATGGCCTTTTGTGGC-3' (SEQ ID NO:23) which is complementary to nucleotides −32 to +3 of rchd534 in FIGS. 6A–6D.
e) 5'-GGACATTTCATTTCATACAATATATGGCCTTTTGT-3' (SEQ ID NO:24) which is complementary to nucleotides −29 to +6 of rchd534 in FIGS. 6A–6D.
f) 5'-TTCATTTCATACAATATATGGCCTTTTGT-3' (SEQ ID NO:25) which is complementary to nucleotides −29 to −1 of rchd534 in FIGS. 6A–6D.
g) 5'-TCATACAATATATGGCCTTTTGT-3' (SEQ ID NO:26) which is complementary to nucleotides −29 to −7 of rchd534 in FIGS. 6A–6D.
h) 5'-AATATATGGCCTTTTGT-3' (SEQ ID NO:27) which is complementary to nucleotides −29 to −13 of rchd534 in FIGS. 6A–6D.

The following antisense molecules can be used to inhibit the expression of the fchd540 gene:
a) 5'-CATGCGGGGCGAGGAGG-3' (SEQ ID NO:28) which is complementary to nucleotides −14 to +3 of fchd540 in FIGS. 2A–2E.
b) 5'-CATGCGGGGCGAGGAGGCGAGGA-3' (SEQ ID NO:29) which is complementary to nucleotides −20 to +3 of fchd540 in FIGS. 2A–2E.
c) 5'-CATGCGGGGCGAGGAGGCGAGGAGAAAAG-3' (SEQ ID NO:30) which is complementary to nucleotides −26 to +3 of fchd540 in FIGS. 2A–2E.
d) 5'-CATGCGGGGCGAGGAGGCGAGGAGAAAAGTCGTTT-3' (SEQ ID NO:31) which is complementary to nucleotides −32 to +3 of fchd540 in FIGS. 2A–2E.
e) 5'-GAACATGCGGGGCGAGGAGGCGAGGAGAAAAGTCG-3' (SEQ ID NO:32) which is complementary to nucleotides −29 to +6 of fchd540 in FIGS. 2A–2E.
f) 5'-GCGGGGCGAGGAGGCGAGGAGAAAAGTCG-3' (SEQ ID NO:33) which is complementary to nucleotides −29 to −1 of fchd540 in FIGS. 2A–2E.
g) 5'-CGAGGAGGCGAGGAGAAAAGTCG-3' (SEQ ID NO:34) which is complementary to nucleotides −29 to −7 of fchd540 in FIGS. 2A–2F.

h) 5'-GGCGAGGAGAAAAGTCG-3' (SEQ ID NO:35) which is complementary to nucleotides −29 to −13 of fchd540 in FIGS. 2A–2E.

Ribozymes:

The central, catalytic portion of a hammerhead ribozyme olecule consist of the following sequence:

5'-CAAAG<u>CNGN</u>XXXX<u>NCNG</u>AGNAGUC-3' (SEQ ID NO:36);

wherein the 5'-proximal CA bases hybridize to a complementary 5'-UG-3' in the target mRNA. The first four underlined bases form a stem by base pairing with the second set of underlined bases, with the intervening bases, shown as X's, forming a non-pairing loop. In order to hybridize to a target mRNA, a hammerhead ribozyme contains additional bases flanking each end of the central segment shown above. The 5' ribozyme flanking segment is complementary to the respective flanking sequences immediately 3' to the target UG; and the 3' flanking segment is complementary to the respective flanking sequence beginning two bases upstream of the target U, and extending 5'-ward (in effect, skipping the first base upstream of the target U). Cleavage occurs between first and second bases upstream of (i.e., 5' to) the U in the target 5'-UG-3' site.

The following ribozyme molecules can be used to inhibit the expression of the rchd534 gene:

a) 5'-GGUGGAGCCCCAGGGCAUUACCUCAAAG CNGNXXXXNCNGAGNAGUCGUGG GCAAGGUGGGCACUCAGGUGGG-3' (SEQ ID NO:37) which will cleave the rchd534 mRNA between nucleotides 716 and 717 in FIGS. 6A–6D.

b) 5'-GUGUCUCUAUGGGUUUGCCCAAAGCNGN XXXXNCNGAGNAGUCUCUGGACA UUUCAUUUCAUAC-3' (SEQ ID NO:38) which will cleave the rchd534 mRNA between nucleotides 1040 and 1041 in FIGS. 6A–6D.

c) 5'-GGCCCUCUCGCCGUCGGGCUCCUUGCUG AGCAAAGCNGNXXXXNCNGAGNA GUCGAUGCCGAAGCCGAUCUUGCUGCGCG-3' (SEQ ID NO:39) which will cleave between nucleotides 1421 and 1422 in FIGS. 6A–6D.

The following ribozyme molecules can be used to inhibit the expression of the fchd540 gene:

a) 5'-CGUUUGCCUGCUAAGGAGCGAACAAAGC NGNXXXXNCNGAGNAGUCGAUGU UUCUUUGUGAGUCGGGCGCCG-3' (SEQ ID NO:40), which will cleave the fchd540 mRNA between nucleotides −53 and −52 in FIGS. 2A–2E.

b) 5'-CGCCGGACGAGCGCAGAUCGUUUGGUCC UGAACAAAGCNGNXXXXNCNGAG NAGUC-CGGGGCGAGGAGGCGAGGAGAAA AGUCG-3' (SEQ ID NO:41), which will cleave the fchd540 mRNA between nucleotides −1 and +1 in FIGS. 2A–2E.

c) 5'-GGAGUAAGGAGGGGGGGAGACUCUAG UUCGCAAAGCNGNXXXXNCNGAGN AGU-CAGUCGGCUAAGGUGAUGGGGGUUGC AGCACACC-3' (SEQ ID NO:42) which will cleave the fchd540 mRNA between nucleotides +602 and +603 in FIGS. 2A–2E.

13. EXAMPLE: EXPRESSION OF FCHD540 ENHANCES TUMORIGENICITY IN PANCREATIC CANCER

The results presented below demonstrate that the fchd540 protein inhibits the TGFβ response and leads to increased cell proliferation. Inhibition of activity or expression of negative regulatory proteins such as fchd540 or rchd534, are, therefore, useful in activating or enhancing the TGFβ response and therefore, controlling fibroproliferative and oncogenic disease.

Results below demonstrate that fchd540 mRNA levels are increased in human pancreatic cancer by comparison with the normal pancreas. Additionally, in situ hybridization experiments demonstrate that fchd540 is overexpressed in the pancreatic cancer cells within the tumor mass. Stable transfection of COLO-357 and PANC-1 human pancreatic cancer cell lines with a full-length fchd540 expression construct leads to complete loss of the TGFβ response. Unlike untransfected cells, those overexpressing fchd540 continued to proliferate in the presence of TGFβ.

13.1. MATERIALS AND METHODS

13.1.1. MATERIALS

The following materials were purchased: FBS, DMEM and RPMI medium, trypsin solution, penicillin-streptomycin solution, and Geneticin (G418) from Irvine Scientific (Santa Ana, Calif.); Genescreen membranes from New England Nuclear (Boston, Mass.); restriction enzymes, random primed labeling kits, Genius 3 non-radioactive nucleic acid detection kits, and Genius 4 RNA labeling kits from Boebringer Mannheim (Indianapolis, Ill.); Immobilon P membranes from Millipore (Bedford, Mass.); and p21$^{Cip1}$ (AB-3) antibodies from NeoMarkers (Fremont, Calif.); Sequenase Version 2.0 DNA Sequencing from USB (Cleveland, Ohio); [α-$^{32}$P]dCTP, [α-$^{35}$s]dATP, and Hybond N+membranes from Amersham (Arlington Heights, Ill.); Lipofectamine from Gibco BRL (Gaithersburg, Md.). All other reagents were from Sigma (St. Louis, Mo.). PANC-1, MIA PaCa-2, ASPC-1, CAPAN-1 human pancreatic cell lines were obtained from ATCC (Rockville, Md.).

13.1.2. TISSUE SAMPLES

Normal human pancreatic tissue samples (N=12; 7 male, 5 female donors; median age 41.8 years; range 14–68 years) and human pancreatic cancer tissues (N=16; 10 male, 6 female; median age 62.6 years; range 53–83 years) were obtained through an organ donor program and from pancreatic cancer patients undergoing surgery. According to the TNM classification of the Union Intenationale Contre le Cancer (UICC) 6 tumors were stage 1, 1 stage 2, and 9 stage 3 ductal adenocarcinoma. Freshly removed tissue samples were fixed in 10% formaldehyde solution for 12–24 hr and paraffin-embedded for histological analysis. In addition, tissue samples were frozen in liquid nitrogen immediately upon surgical removal and maintained at −80° C. until use for RNA extraction.

13.1.3. RNA EXTRACTION AND NORTHERN BLOT ANALYSIS

Total RNA was extracted by the single step acid guadinium thiocyanate phenol chloroform method and poly (A)+RNA was prepared by affinity chromatography on oligo-dT cellulose (Baldwin, et al., 1996, Int. J. Cancer 6:283–288) Size fractioned RNA was electrotransferred onto nylon membranes. Blots were hybridized with a $^{32}$P labeled fchd540 cDNA probe and exposed at −80° C. to Kodak Biomax MS films. A 190 bp 7S cDNA probe, and a 150 bp β-actin cDNA probe were used to confirm equivalent loading of total, and poly(A)+RNA loading, respectively (Baldwin, et al., 1996, Int. J. Cancer6:283–288; Korc, et al., 1992, J. Clin. Invest. 90: 1352–1360). Specifically, total RNA (20 µg/lane) from 6 normal pancreatic tissues, and 8 pancreatic cancers was subjected to Northern blot analysis using a labeled fchd540 cDNA probe (500,000 cpm/ml). A 7S ribosomal cDNA probe (50,000 cpm/ml) was used as a loading and transfer control. Exposure times were 2 days for fchd540 and 6 hr for 7S. For cell line analysis, poly(A)+

RNA (2 μg/lane) was isolated from ASPC-1, CAPAN-1, COLO-357, MIA-PaCa-2, PANC-1, and T3M4 pancreatic cancer cell lines and from human placenta were analyzed by Northern blotting using a $^{32}$P-labeled fchd540 cDNA probe (500,000 cpm/ml). A human β-actin cDNA probe (50,000 cpm/ml) was used as a loading and transfer control. Exposure times were 1 day for fchd540 and 2 hours for β-actin. Total RNA (20 μg/lane) from parental, sham-transfected, and 4 fchd540 transfected clones as indicated of COLO-357 and PANC-1 pancreatic cancer cells was subjected to Northern blot analysis using a $^{32}$P-labeled fchd540 cDNA probe (500,000 cpm/ml). Exposure time was 2 days. Equal loading of lanes was confirmed by ethidium bromide staining of the RNA.

13.1.4. IN SITU HYBRIDIZATION

Tissue sections (4 μm thick) were placed on 3-aminopropyl-methoxysilane-coated slides, deparaffinized and incubated at 23° C. for 20 minutes with 0.2N HCl and at 37° C. for 15 min with 40 μg/ml proteinase K. The sections were then post-fixed for 5 min in phosphate buffered saline (PBS) containing 4% paraformaldehyde, incubated briefly twice with PBS containing 2 mg/ml glycine and once in 50% (V/V) fomamide/2×SSC for 1 hour prior to initiation of the hybridization with 100 μl hybridization buffer, containing digoxigenin-labeled fchd540 riboprobe.

The probes were labeled with digoxigenin-UTP by 17 or 5P6 RNA polymerase using the Genius 4 RNA labeling kit. Hybridization was performed in a moist chamber for 16 hr at 42C. The sections were then incubated for 60 minutes at 23° C. with 1% (w/v) blocking reagents, and for 30 minutes at 23° C. with a 1:2000 dilution of an alkaline phosphatase conjugated polyclonal sheep anti-digoxigenin Fab fragment antibody using the Genius 3 nonradioactive nucleic acid detection kit. Following a 2–3 hours incubation with color solution containing nitroblue tetrazolium and X-phosphate in a dark box, the sections were mounted in aqueous mounting medium.

13.1.5. CELL CULTURE

Human pancreatic cancer cells were routinely grown in DMEM (COLO-357, MIA-PaCa-2, PANC-1) or RPMI (ASPC-1, CAPAN-1, T3M4) supplemented with 10% FES, 100 U/ml penicillin, and 100 p.g/ml streptomycin (complete medium). Growth assays were performed by incubating cells in serum-free medium (DMEM containing 0.1% BSA, 5 μg/ml transferrin, 5 ng/ml sodium selenite, and antibiotics) in the absence or presence of TGFβ1, followed by addition of 3-(4,5-methylthiazol-2-yl)-2,5-diphenyl-tetrazolium bromide (MTT, 62.5 μg/well) for 4 hours (Raitano, et al., 1993, *J. Biol. Chem.* 265: 10466–10472). In pancreatic cancer cells the results of the MTT assay correlate with results obtained by cell counting with a hemocymeter and by monitoring [$^3$H]-thymidine incorporation (Raitano, et al., 1993, *J. Biol. Chem.* 265: 10466–10472; Baldwin et al., 1993, *Growth Factors*, 8: 23–34). Basal anchorage-independent growth was assessed by a double soft agar assay (Kornmann et al., 1998, *J. Clin. Invest.* 101, 344–352). After 14 days colonies were counted by microscopy and stained with MTT solution for 12 hours.

13.1.6. GROWTH IN NUDE MICE

Sham transfected or fchd540 transfected COLO-357 cells ($2\times10^6$) were injected subcutaneously into 2 sides of 4–6 weeks old, female, athymic (nude) mice. The animals were monitored for tumor formation every week for 6 to 12 weeks. Tumor volume was calculated as $\pi/4 \times \text{width} \times \text{height} \times \text{length}$ of the tumor (Kornmann et al., 1998, *J. Clin. Invest.* 101, 344–352).

13.1.7. STABLE AND TRANSIENT TRANSFECTIONS

Transfection of fchd540.pCI.neo into COLO-357 and PANC-1cells was carried out by the lipofectarmine method. After reaching confluence, cells were split 1:10 in selection medium (complete medium supplemented with 0.4 mg/ml and 1 mg/ml G418 for COLO-357 and PANC-1 cells, respectively). Single clones were isolated after 2–4 weeks. After clonal expansion, cells from each individual clone were screened for expression of fchd540 by Northern blot analysis. Parental COLO-357 and PANC-I cells were also transfected with a control expression vector containing the neomycin resistant gene (pRSVneo), and the resultant clones termed sham transfected. Positive clones were routinely grown in selection medium.

For transient transfection, cells were plated overnight at a density of 25,000 cells/well in 24-well plates and transiently transfected with the p3TP-Lux plasmid using 1.5 μl/well lipofectamine and 0.5 μg plasmid/well in 500 μl serum free medium. Following a 5 hours incubation, equal volumes of medium containing 20% FBS were added for 12 hours. Cells were then incubated for 24 hours in complete medium and subsequently incubated for 12 hours in serum free medium prior to the addition of TGFβ1. Cells were solubilized in lysis buffer containing 25 mM Tris HCl (pH 7.8), 2 mM DTT, 2 mM EGTA, 10% glycerol and 1% Triton X-100. Luciferase was assayed with a luminometer (Monolight 2010B: Analytical Luminescence Laboratory, San Diego, Calif.) for 10 seconds after addition of the substrate solution containing 20 mM tricine, 1.07 mm magnesium-bicarbonate, 2.67 mM magnesium-sulfate, 0.1 mM EDTA, 530 μM ATP, 470 μM luciferin, 270 μM Coenzyme A (sodium salt), and 33.3 mM DTT.

13.1.8. IMMUNOBLOTTING

Cells were solubilized in lysis buffer containing 50 mM TRIS, 150 mM NaCl, 1 mM EDTA, 1 μg/ml pepstatin A, 1 mM phenylmethylsulfonyl fluoride (PMSF), and 1% Triton X-100. Proteins were subjected to SDS polyacrylamide gel electrophoresis (SDS-PAGE), transferred to Immobilon P embranes, incubated for 90 minutes with the indicated antibody, and for 60 minutes with a secondary antibody against mouse or rabbit IgG. Visualization was performed by enhanced chemiluminescence.

13.1.9. STATISTICS

Student's t-test was used for statistical analysis, $P<0.05$ was taken as the level of significance. Results of MTT cell growth assays and luciferase reporter gene assays are expressed as mean ± standard error of mean (SEM) of at least 3 separate experiments.

13.2. RESULTS

13.2.1. fchd540 EXPRESSION IN HUMAN PANCREATIC TISSUES AND PANCREATIC CANCER CELL LINES In order to examine the expression patterns of fchd540, Northern blot analysis was performed to compare normal tissue with pancreatic cancer tissue. Northern bolt analysis revealed a faint 4.4 kb fchd540 mRNA transcript in 3 of 12 normal pancreatic tissue samples, and moderate to high levels of this mRNA moiety in 7 of 16 pancreatic cancer samples.

Two approaches were taken next to determine whether pancreatic cancer cell lines express fchd540 mRNA. First, Northern blot analysis of poly(A)+RNA isolated from 6 pancreatic cancer cell lines revealed moderate levels of this mRNA moiety in ASPC-1, CAPAN-I, COLO-357, and PANC-1 cells, and relatively low levels in MIA-PaCa-2 and T3M4 pancreatic cancer cells. In order to further examine the localization of fchd540 in these tissues, in situ hybridization was carried out in those cancer samples that overexpressed fchd540 by Northern blot analysis. fchd540 mRNA was abundant in the cancer cells within the tumor mass, and was also present in the endothelial lining of the associated blood vessels. In situ hybridization with sense probes did not produce any specific signal.

13.2.2. EFFECTS OF OVEREXPRESSING fchd540 IN COLO-357 AND PANC-1 PANCREATIC CANCER CELLS To investigate the functional effects of fchd540 overexpression in pancreatic cancer cell lines, COLO-357 and PANC-1were stably transfected with a full length fchd540 construct. Overall, 20 independent COLO-357 and 10 PANC-1 clones were selected after 4 weeks of growth in selection medium. Subsequent experiments were carried out in 4 clones from each cell line. These clones were selected because they displayed increased fchd540 mRNA levels by Northern blot analysis of total RNA.

TGFβ1 inhibited the growth of wild-type and sham (control) transfected COLO-357 cells after 72 hours of incubation, with maximal effects occurring at a concentration of 1 nM TGFβ1 (−41%; p<0.01). In contrast, under the same conditions, TGFβ1 did not inhibit the growth of fchd540 overexpressing COLO-357 clones (FIG. 7A).

TGF-β1 inhibited the growth of wild-type and sham transfected PANC-1 cells, maximal effects occurring at a concentration of 1 nM TGFβ1 (−29%; p<0.01). In contrast, under the same conditions TGFβ1 did not inhibit the growth of fchd540 overexpressing PANC-1 clones (FIG. 7B).

Wild-type and sham transfected COLO-357 cells displayed exponential doubling times of 29 to 31 hours. The fchd540 overexpressing COLO-357 clones exhibited similar doubling times (30 to 38 hours). No significant difference in the doubling times was observed between parental, sham transfected, and fchd540 transfected PANC-1 clones (24 to 26 h). However, wild-type and sham transfected COLO-357 cells displayed colony forming efficiencies of −1.0%, whereas fchd540 transfected clones displayed significantly (p<0.001) higher colony forming efficiencies of 12%–14% (FIG. 8A). Parental and wild- type PANC-1 cells exhibited relatively high colony forming efficiencies of −28%, which did not significantly differ from those observed in the fchd540 transfected PANC-1 clones (FIG. 8B).

To determine whether the enhanced anchorage-independent growth of fchd540 expressing COLO-357 clones resulted in enhanced tumorigenicity in vivo, 2×10$^6$ sham transfected or fchd540 transfected COLO-357 cells were injected subcutaneously in athymic (nude) mice at each site and tumor growth was measured weekly. fchd540 expressing COLO-357 clones exhibited earlier and more rapid tumor growth in comparison to sham transfected cells (FIG. 8C).

Taken together, results presented in this Example demonstrate that fchd540 mRNA levels were elevated in a significant percentage of human pancreatic cancers in comparison with the normal pancreas. Expression of fchd540 was detected in the cancer cells within the tumor mass. Additionally, cultured human pancreatic cancer cell lines demonstrated fchd540 expressed at low levels.

Finally overexpression of fchd540 in two TGFβ-sensitive cell lines resulted in complete loss of TGFβ response. This observation indicates that enhanced expression of fchd540 can abrogate the TGFβ response in TGFβ-related oncogenic disorders, such as pancreatic cancer, thus demonstrating a specific target for therapeutic intervention for fibroproliferative and oncogenic disease states involving aberrant TGFβ signaling.

13. DEPOSIT OF MICROORGANISMS

The following microorganisms were deposited with the American Type Culture Collection (ATCC), Manassas, Va., on the indicated dates and assigned the indicated accession numbers:

| Microorganism | ATCC Accession No. | Date of Deposit |
| --- | --- | --- |
| pFCHD531 | 69983 | February 7, 1996 |
| pFCHD540 | 69984 | February 7, 1996 |
| fchd545 | 69974 | January 5, 1996 |

The following microorganism was deposited with the Agricultural Research Service Culture Collection (NRRL), Peoria, Ill., on the indicated date and assigned the indicated accession number:

| Microorganism | NRRL Accession No. | Date of Deposit |
| --- | --- | --- |
| FCHD534 | B-21459 | June 6, 1995 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for identifying a substance to be tested for an ability to ameliorate symptoms of a fibroproliferative disease or oncogenic related disorder comprising, assaying the ability of the substance to modulate the expression level of, or the activity of the encoded protein product of, the rchd534 gene or the fchd540 gene by:
   a) exposing a subject or cell to a test substance;
   b) assaying the expression level of, or the activity of the encoded protein product of, the rchd534 gene or the fchd540 gene in both the subject or cell exposed to said test substance and in a control sample of cells not exposed to said test substance; and
   c) comparing the expression level of the gene, or the activity of the encoded protein product of, the rchd534 gene or the fchd540 gene in both subjects or cells, wherein a test substance which modulates the expression level of, or the activity of the encoded protein product of the rchd534 gene or the fchd540 gene, as compared to a control subject or cell, indicates that said test substance is a substance to be tested for an ability to ameliorate symptoms of a fibroproliferative disease or oncogenic related disorder.

2. The method of claim 1 in which the fibroproliferative disease is diabetic retinopathy.

3. The method of claim 1 in which the oncogenic related disorder is a tumor growth.

4. The method of claim 1 in which the oncogenic related disorder is angiogenesis.

5. The method of claim 1, wherein the oncogenic related disorder is pancreatic cancer.

6. The method of claim 1, wherein the expression of, or the activity of the encoded protein product of, the rchd534 gene or the fchd540 is reduced.

7. The method of claim 1 in which the substance is an oligonucleotide complementary to the 5' region of the gene and blocks transcription via triple helix formation.

8. The method of claim 1 in which the substance is an antisense or ribozyme molecule that blocks translation of the gene.

9. The method of claim 1 in which the substance is a small organic or inorganic molecule that modulates the activity of the protein product by binding to the protein product.

10. The method of claim 9 in which the substance reduces the activity of the protein product by binding to the protein product.

11. The method of claim 1 in which the substance is an antibody that modulates the activity of the protein product by binding to the protein product.

12. The method of claim 11 in which the substance reduces the activity of the protein product by binding to the protein product.

13. A method for diagnosing a fibroproliferative disease or an oncogenic related disorder comprising:
   a) detecting the level of fchd540 transcript or rchd534 transcript present in a patient or patient sample and in a corresponding control sample; and
   b) comparing the level of fchd540 or rchd534 transcript in both samples, wherein if the level of transcript detected differs in the patient sample relative to the corresponding control sample, a fibroproliferative disease or an oncogenic related disorder is diagnosed.

14. The method of claim 13, wherein the fchd540 or the rchd534 transcript level detected is higher than that of a corresponding control sample.

15. The method of claim 13 wherein the oncogenic related disorder is pancreatic cancer.

16. A method for diagnosing a fibroproliferative disease or an oncogenic related disorder comprising:
   (a) detecting fchd540 or rchd534 protein level or protein activity present in a patient or patient sample and in a corresponding control sample; and
   (b) comparing the fchd540 or rchd534 protein level or protein activity in both samples, wherein if the level of protein or protein activity detected differs in the patient or patient sample relative to the corresponding control sample, a fibroproliferative disease or an oncogenic related disorder is diagnosed.

17. The method of claim 16, wherein the fchd540 or the rchd534 protein level or activity detected is higher than that of a corresponding control sample.

18. The method of claim 16 wherein the oncogenic related disorder is pancreatic cancer.

19. A method for characterizing a fibroproliferative disease or oncogenic related disorder comprising, assaying, in a patient or sample, overexpression of a gene encoding the fchd531 protein, the fchd540 protein or the rchd534 protein relative to expression in a control sample.

20. The method of claiim 19, wherein the oncogenic related disorder is pancreatic cancer.

21. A method for monitoring the efficacy of a compound in clinical trials for the treatment of a fibroproliferative disease or oncogenic related disorder comprising, assaying, in a patient or sample, overexpression of a gene encoding the fchd540 protein or the rchd534 protein relative to expression in a control patient or sample.

22. The method of claim 21, wherein the oncogenic related disorder is pancreatic cancer.

* * * * *